(12) United States Patent
Gellett et al.

(10) Patent No.: US 7,998,714 B2
(45) Date of Patent: Aug. 16, 2011

(54) PROCESS FOR ACCELERATED CAPTURE OF CARBON DIOXIDE

(75) Inventors: Wayne L. Gellett, Ballwin, MO (US); Tracy L. Bucholz, St. Louis, MO (US); Richard T. Zvosec, Edina, MN (US); Joshua Schumacher, St. Charles, MO (US); Robert A. Clayton, Foristell, MO (US); Robert P. Shirtum, Sonora, TX (US)

(73) Assignee: Akermin, Inc., St. Louis, MO (US)

( * ) Notice: Subject to any disclaimer, the term of this patent is extended or adjusted under 35 U.S.C. 154(b) by 0 days.

(21) Appl. No.: 12/569,850

(22) Filed: Sep. 29, 2009

(65) Prior Publication Data

US 2010/0086983 A1    Apr. 8, 2010

Related U.S. Application Data

(60) Provisional application No. 61/147,462, filed on Jan. 26, 2009, provisional application No. 61/101,052, filed on Sep. 29, 2008.

(51) Int. Cl.
  *C12P 3/00*   (2006.01)
  *C12N 11/04*  (2006.01)
  *C12M 1/00*   (2006.01)

(52) U.S. Cl. ..... 435/168; 435/182; 435/174; 435/229.1; 435/266

(58) Field of Classification Search ............... 435/299.1, 435/174, 182, 266, 438, 168
See application file for complete search history.

(56) References Cited

U.S. PATENT DOCUMENTS

| | | | |
|---|---|---|---|
| 6,143,556 A | 11/2000 | Trachtenberg |
| 6,475,382 B2 | 11/2002 | Parent |
| 6,524,843 B1 | 2/2003 | Blais et al. |
| 6,602,703 B2 | 8/2003 | Dutil |
| 6,846,584 B2 | 1/2005 | Dutil et al. |
| 6,890,497 B2 | 5/2005 | Rau et al. |
| 6,908,507 B2 | 6/2005 | Lalande et al. |
| 6,946,288 B2 | 9/2005 | Blais et al. |
| 7,132,090 B2 | 11/2006 | Dziedzic et al. |
| 7,176,017 B2 | 2/2007 | Parent et al. |
| 7,514,056 B2 | 4/2009 | Fradette et al. |
| 7,521,217 B2 | 4/2009 | Daigle et al. |
| 7,527,770 B2 | 5/2009 | Monzyk et al. |
| 7,579,185 B2 | 8/2009 | Parent et al. |
| 7,596,952 B2 | 10/2009 | Fradette et al. |
| 7,638,228 B2 | 12/2009 | Minteer et al. |
| 7,642,076 B2 * | 1/2010 | Dziedzic et al. .............. 435/174 |
| 7,655,193 B1 | 2/2010 | Rau et al. |
| 7,709,134 B2 | 5/2010 | Minteer et al. |
| 2004/0029257 A1 | 2/2004 | Dutil et al. |
| 2004/0259231 A1 | 12/2004 | Bhattacharya |
| 2005/0095466 A1 | 5/2005 | Minteer et al. |
| 2006/0128004 A1 | 6/2006 | Anctil et al. |
| 2006/0246564 A1 | 11/2006 | Parent et al. |
| 2007/0048856 A1 | 3/2007 | Parent et al. |
| 2008/0003662 A1 | 1/2008 | Trachtenberg |
| 2008/0014622 A1 | 1/2008 | Federspiel et al. |
| 2008/0148939 A1 | 6/2008 | Fradette et al. |
| 2008/0245660 A1 | 10/2008 | Little et al. |
| 2008/0245672 A1 | 10/2008 | Little et al. |
| 2008/0248350 A1 | 10/2008 | Little et al. |
| 2009/0007779 A1 | 1/2009 | Coignet et al. |
| 2009/0104098 A1 | 4/2009 | Singh |
| 2009/0136827 A1 | 5/2009 | Minteer et al. |
| 2009/0155889 A1 | 6/2009 | Handagama et al. |
| 2009/0227010 A1 | 9/2009 | Daigle et al. |
| 2009/0305113 A1 | 12/2009 | Minteer et al. |
| 2009/0305391 A1 | 12/2009 | Parent et al. |
| 2010/0005959 A1 | 1/2010 | Littau et al. |
| 2010/0047866 A1 | 2/2010 | Borchert et al. |
| 2010/0074828 A1 | 3/2010 | Singh |
| 2010/0092359 A1 | 4/2010 | Svendsen et al. |

FOREIGN PATENT DOCUMENTS

| | | |
|---|---|---|
| CA | 2 352 626 A1 | 1/2003 |
| CA | 2 554 395 A1 | 1/2007 |
| EP | 0 948 390 B1 | 3/2001 |
| EP | 0 991 462 B1 | 4/2003 |
| EP | 0 649 385 B1 | 5/2003 |
| EP | 1 521 629 B1 | 2/2007 |
| EP | 1 377 531 B1 | 7/2007 |
| EP | 2 145 668 A1 | 1/2010 |
| WO | 96/40414 A1 | 12/1996 |
| WO | 2004/056455 A1 | 7/2004 |
| WO | 2006/089423 A1 | 8/2006 |
| WO | 2006/108532 A1 | 10/2006 |
| WO | 2008/072979 A1 | 6/2008 |
| WO | 2008/082694 A2 | 7/2008 |
| WO | 2008/137846 A2 | 11/2008 |
| WO | 2009/000025 A1 | 12/2008 |
| WO | 2010/037138 A2 | 4/2010 |
| WO | 2010/045689 A1 | 4/2010 |

* cited by examiner

*Primary Examiner* — Chih-Min Kam
(74) *Attorney, Agent, or Firm* — Senniger Powers LLP

(57) ABSTRACT

The present invention generally relates to the removal of carbon dioxide from a gas stream, particularly a flue gas, hydrogen gas from a reformer, natural gas, or gas from a cement kiln. Immobilized enzymes for use in carbon capture and other systems are also disclosed.

20 Claims, 15 Drawing Sheets

PROCESS FOR ACCELERATED CAPTURE OF CARBON DIOXIDE

CROSS-REFERENCE TO RELATED APPLICATIONS

This application is a Non-Provisional patent application of U.S. Provisional Patent Application Ser. No. 61/147,462, filed Jan. 26, 2009, and U.S. Provisional Patent Application Ser. No. 61/101,052, filed Sep. 29, 2008, the entirety of which are herein incorporated by reference.

FIELD OF THE INVENTION

The present invention generally relates to the removal of carbon dioxide from a gas stream, particularly a flue gas, hydrogen gas from a reformer, natural gas, or gas from a cement kiln.

BACKGROUND OF THE INVENTION

Technologies are being developed for capturing carbon dioxide ($CO_2$) from industrial gas streams to reduce energy costs and the environmental impact of $CO_2$ in the atmosphere. Major sources of $CO_2$ output include power plants, cement kilns, natural gas processing facilities, ammonia plants, and hydrogen plants. The captured $CO_2$ may have multiple uses, including sequestration, enhanced oil recovery, or accelerated algae growth. In the cases of hydrogen, ammonia, and natural gas, removal of $CO_2$ is necessary to increase the value of the gas stream.

Currently several alternate $CO_2$ capture technologies are in various stages of commercial practice and development. These include chemical absorption with amines (particularly monoethanolamine—MEA), physical adsorption, membrane separation, and cryogenic distillation. In addition, technologies such as oxycombustion and Integrated Gasification Combined Cycle, which remove the carbon or non-oxygen gas components prior to combustion, are being considered as ways to eliminate flue gas removal. Chemical absorption with amines is currently the lowest cost method of $CO_2$ removal for the majority of gas streams, particularly for the clean-up of low levels of $CO_2$ in natural gas. MEA systems are more reactive, and therefore preferred, but the energy load to remove the absorbed $CO_2$ from the MEA, at about 4 million BTU/tonne of $CO_2$ is very high and can require up to about one-third of a power plant's boiler output.

SUMMARY OF THE INVENTION

Among the various aspects of the invention is a system comprising an immobilized carbonic anhydrase for removing carbon dioxide from a gas stream, particularly, a flue gas, hydrogen gas from a reformer, natural gas, or gas from a cement kiln.

Another aspect is a process for removing $CO_2$ from a $CO_2$-containing gas, the process comprising contacting an aqueous liquid with a $CO_2$-containing gas to promote diffusion of the $CO_2$ into the aqueous liquid; and contacting the $CO_2$ in the aqueous liquid with immobilized carbonic anhydrase entrapped in a polymeric immobilization material to catalyze hydration of the $CO_2$ and form a treated liquid containing hydrogen ions and bicarbonate ions, wherein the polymeric immobilization material either (i) stabilizes the carbonic anhydrase or (ii) comprises a micellar or inverted micellar material.

Yet another aspect is the process described above wherein the process is performed in a reaction vessel which comprises a bottom portion including a gas inlet and a liquid outlet, a top portion including a liquid inlet and a gas outlet, and a middle portion containing a plurality of particles coated with immobilized carbonic anhydrase entrapped in a polymeric immobilization material wherein the polymeric immobilization material either (i) stabilizes the carbonic anhydrase or (ii) comprises a micellar or inverted micellar material. The process comprises contacting an aqueous liquid which enters the liquid inlet and flows downward in the reaction vessel with a $CO_2$-containing gas which enters the gas inlet and flows upward in the reaction vessel to promote diffusion of the $CO_2$ into the aqueous liquid and catalyze hydration of the $CO_2$ in the aqueous liquid in the presence of the immobilized carbonic anhydrase to form a treated liquid containing hydrogen ions and bicarbonate ions and a treated gas; and evacuating the treated liquid from the liquid outlet and evacuating the treated gas from the gas outlet.

A further aspect of the invention is a reaction vessel for removing $CO_2$ from a $CO_2$-containing gas comprising a bottom portion containing a gas inlet and a liquid outlet, a top portion containing a liquid inlet and a gas outlet, and a middle portion containing a plurality of particles coated with carbonic anhydrase entrapped in a polymeric immobilization material wherein the polymeric immobilization material either (i) stabilizes the carbonic anhydrase or (ii) comprises a micellar or inverted micellar material. The carbonic anhydrase is capable of catalyzing hydration of $CO_2$ into hydrogen ions and bicarbonate ions.

Yet another aspect is an enzyme immobilized by entrapment in a polymeric immobilization material, the material being permeable to a compound smaller than the enzyme and the enzyme being modified ionically or covalently by a hydrophilic, hydrophobic, or amphiphilic moiety.

An enzyme immobilized by entrapment in a polymeric immobilization material, the immobilization material being permeable to a compound smaller than the enzyme and having the structure of either Formulae 5, 6, 7, or 8:

Formula 5

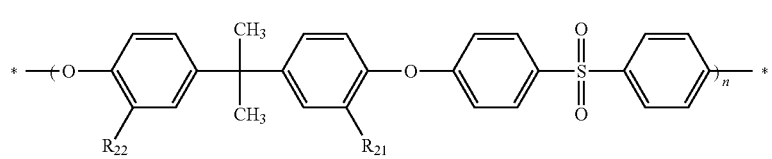

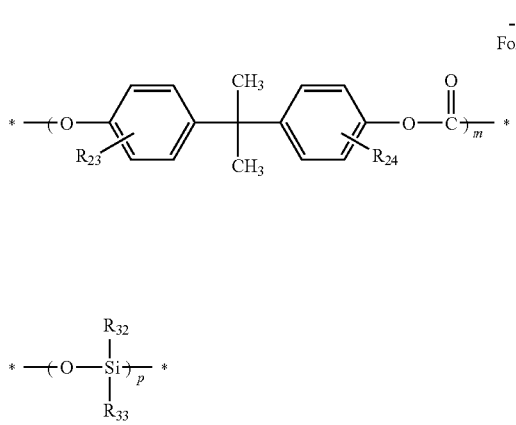

Formula 6

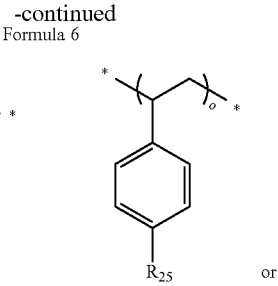

Formula 7 or

Formula 8 wherein $R_{21}$ and $R_{22}$ are independently hydrogen, alkyl, or substituted alkyl, provided that the average number of alkyl or substituted alkyl groups per repeat unit is at least 0.1; $R_{23}$ and $R_{24}$ are independently hydrogen, alkyl, or substituted alkyl, provided that the average number of alkyl or substituted alkyl groups per repeat unit is at least 0.1; $R_{25}$ is hydrogen, alkyl, or substituted alkyl, provided that the average number of alkyl or substituted alkyl groups per repeat unit is at least 0.1; $R_{32}$ and $R_{33}$ are independently hydrogen, alkyl, aryl, or substituted alkyl, provided that the average number of alkyl or substituted alkyl groups per repeat unit is at least 0.1 and m, n, o, and p are an integer of at least 10.

Another aspect is a system for removing $CO_2$ from a $CO_2$-containing gas comprising first and second reaction vessels, the first reaction vessel being the reaction vessel described above and the second reaction vessel containing particles coated with carbonic anhydrase entrapped in a polymeric immobilization material wherein the carbonic anhydrase is capable of catalyzing conversion of the hydrogen ions and the bicarbonate ions into concentrated $CO_2$ and water.

A further aspect is a process for removing $CO_2$ from a $CO_2$-containing gas comprising contacting an aqueous liquid with a $CO_2$-containing gas to promote diffusion of the $CO_2$ into the aqueous liquid; and contacting the $CO_2$ in the aqueous liquid with immobilized carbonic anhydrase to catalyze hydration of the $CO_2$ and form a treated liquid containing hydrogen ions and bicarbonate ions. The aqueous liquid comprises methylamine, ethylamine, propylamine, iso-propylamine, butylamine, iso-butylamine, sec-butylamine, tert-butylamine, pentylamine, iso-pentylamine, sec-pentylamine, tert-pentylamine, hexylamine, iso-hexylamine, sec-hexylamine, tert-hexylamine, ethylenediamine, (2-methylbutyl)amine, 2-aminopentane, 3-(tert-butoxy)propylamine, 2-amino-6-methylheptane, 1-ethylpropylamine dimethylamine, diethylamine, dipropylamine, dibutylamine, dipentylamine, dihexylamine, N-ethylmethylamine, N-isopropylmethylamine, N-butylmethylamine, N-ethylisopropylamine, N-tert-butylmethylamine, N-ethylbutylamine, 3-isopropoxypropylamine, chloro(diethylamino)dimethylsilane, 2,2'-(ethylenedioxy)bis(ethylamine), 1,3-bis(chloromethyl)-1,1,3,3-tetramethyldisilazane, N-tert-butylisopropylamine, N,N-diethyltrimethylsilylamine, di-sec-butylamine, trimethylamine, triethylamine, tripropylamine, tributylamine, dimethylpropylamine, diethylpropylamine, N,N-diisopropylmethylamine, N-ethyldiisopropylamine, N,N-dimethylethylamine, N,N-diethylbutylamine, 1,2-dimethylpropylamine, N,N-diethylmethylamine, N,N-dimethylisopropylamine, 1,3-dimethylbutylamine, 3,3-dimethylbutylamine, N,N-dimethylbutylamine, or a combination thereof.

Yet another aspect is the process, reaction vessel, or system described above wherein the carbonic anhydrase is a bovine carbonic anhydrase or a human carbonic anhydrase. Particularly, the carbonic anhydrase is a bovine carbonic anhydrase II, a human carbonic anhydrase IV, or a modified human carbonic anhydrase IV.

Other objects and features will be in part apparent and in part pointed out hereinafter.

DESCRIPTION OF THE INVENTION

The system of the invention accelerates the rate of absorption and reaction of $CO_2$ into the aqueous phase of a carbonate ($CO_3^{2-}$) solution to form bicarbonate ($HCO_3^-$). The overall chemistry is as follows:

$$CO_3^{2-} + H_2O + CO_2 \rightarrow 2HCO_3^-$$

Without enzyme, the reaction occurs in a two-step sequence:

$$CO_3^{2-} + H_2O \rightarrow OH^- + HCO_3^- \qquad (1)$$

$$CO_2 + OH^- \rightarrow HCO_3^- \qquad (2)$$

At a pH of greater than 10.5, the reaction rate may be diffusion limited by the low solubility of $CO_2$ in water. At a pH of less than 10.5, the reaction rate is very slow due to the low concentration of $OH^-$.

Another way to effect the hydration of $CO_2$ is to use carbonic anhydrase (CA) to catalyze the reaction; the enzyme catalyzed reaction has a different two-step sequence:

$$CO_2 + H_2O \rightarrow H^+ + HCO_3^- \qquad (3)$$

$$CO_3^{2-} + H^+ \rightarrow HCO_3^- \qquad (4)$$

Figure 1:
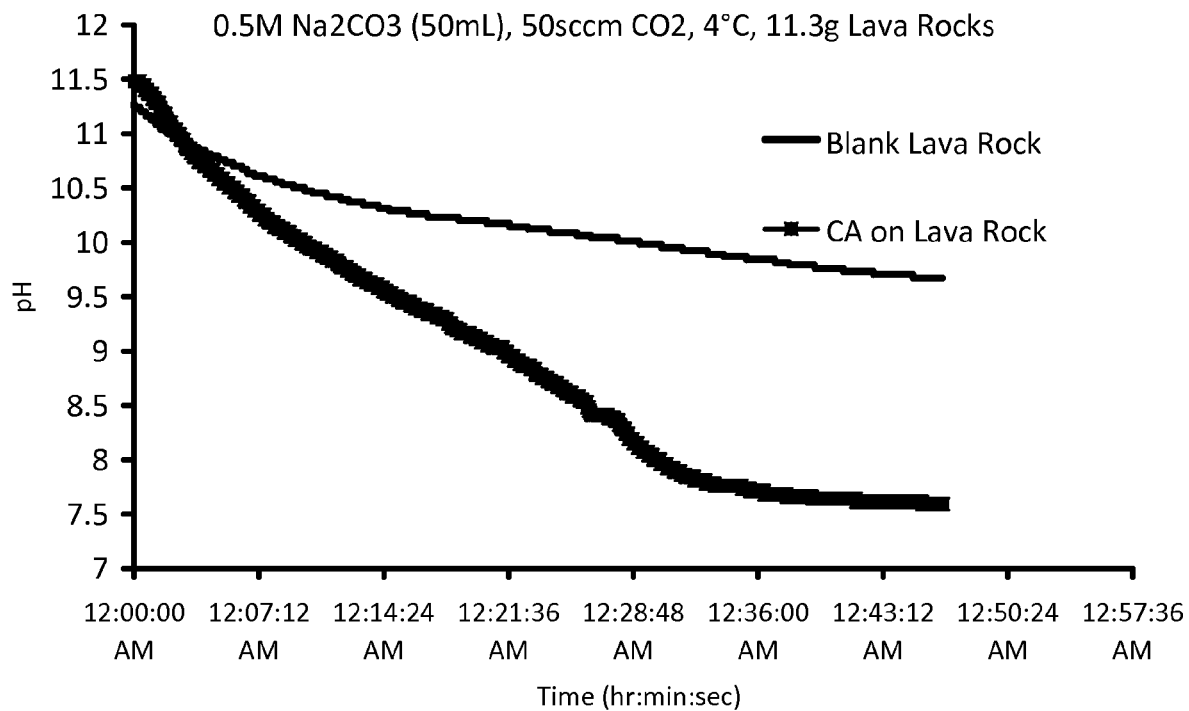
FIG. 1 is a graph of pH versus time for a reaction of carbon dioxide conversion to carbonic acid for a reaction catalyzed by carbonic anhydrase and a reaction with no carbonic anhydrase catalysis wherein the experiment was performed in 0.5M $Na_2CO_3$, 50 sccm $CO_2$, at 4° C., and using 25 mg (0.5 mg/mL) carbonic anhydrase.

By using CA to catalyze $CO_2$ hydration [reaction (3)], the rate of conversion of $CO_2$ into the bicarbonate form is accelerated, particularly at pH less than 10.5. The $K_{eq}$ for the hydration reaction at 25° C. is $1.7 \times 10^{-3}$; the reaction at equilibrium favors the $CO_2/H_2O$ side of the equation. In the presence of CA, the reaction rate of the approach to equilibrium increases by six to eight orders of magnitude. In reaction (4), the carbonate captures the proton produced in reaction (3) and creates a driving force to produce more bicarbonate and protons. Data showing the increased reaction rate for $CO_2$ hydration as evidenced by the faster decrease in the pH of the reaction mixture is shown in FIG. 1.

Similarly in a second reactor, CA catalyzes the dehydration of the bicarbonate back into $CO_3^{2-}$, $CO_2$, and water. The carbonate can be recycled back to the first reactor where the dehydration of $CO_2$ occurs. For example, the chemistry for dehydration of $CO_2$ is as follows:

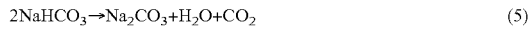
$$2NaHCO_3 \rightarrow Na_2CO_3 + H_2O + CO_2 \qquad (5)$$

Upon heating, bicarbonate releases the $CO_2$ and water and forms carbonate ions that can be recycled to the hydration reaction. The CA in the dehydration reactor is similar to that in the $CO_2$ hydration unit and should increase the rate of this reaction. When the sodium is replaced by another cation (e.g., alkali metal, alkaline earth metal, etc.), the metal is selected so that the resulting carbonate is preferably soluble in the aqueous solution. At standard temperature and pressure, $CO_2$ has a solubility of about 1.8 grams/liter; thus a system allowing for rapid transfer of $CO_2$ to the aqueous phase is desired.

System Design

The system used to hydrate carbon dioxide gas in a gas stream to form bicarbonate ions can use a variety of reactors, including a packed bed, a fluidized bed, or a continuous stirred tank. When a packed or fluidized bed reactor is used, the gas and liquid streams entering the reactor can be in a co-current or counter current configuration. For example, in a co-current system, the gas and liquid streams could enter the reactor in the form of microbubbles of gas in the liquid stream. Further, the packing of the reactors could be packing material comprising immobilized carbonic anhydrase; for example, the immobilized carbonic anhydrase could be coated on the packing material. In some of these embodiments the packing material has a high surface area. Further, the configuration in the reactor could be similar to a tray style distillation column wherein the packing material includes a membrane comprising the immobilized carbonic anhydrase is oriented to maximize the surface contact with the gas and liquid streams (e.g., by folding the membrane back on itself in a serpentine configuration).

Figure 2A:
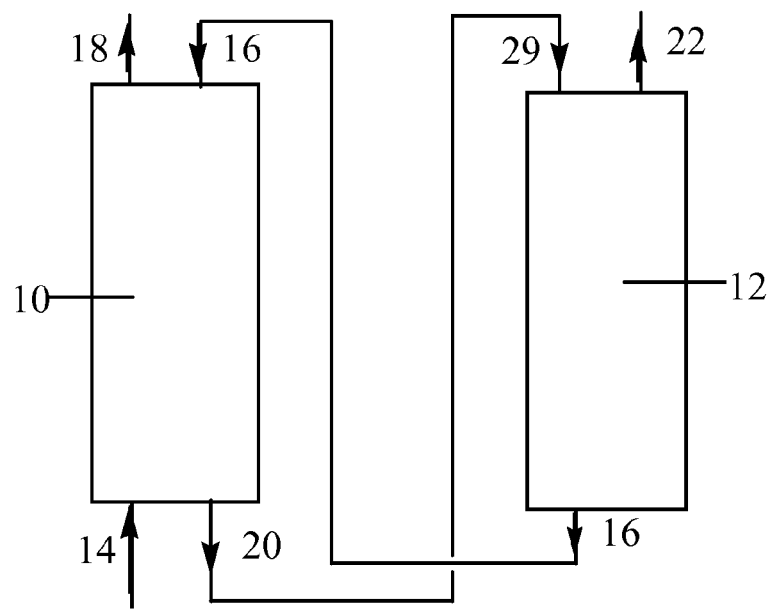
FIG. 2A is a schematic of a $CO_2$ absorber and FIG. 2B is a schematic of a $CO_2$ desorber.

In one particular system, a two unit continuous flow system can be used to hydrate $CO_2$ gas to form bicarbonate ions in a $CO_2$ absorber and dehydrate the bicarbonate ions to $CO_2$, water, and carbonate ions in a $CO_2$ desorber. In some instances, the units have a packed tower design. A schematic diagram of this two unit system including an absorber 10 and a desorber 12 is depicted in FIG. 2. A $CO_2$ gas stream 14 enters the bottom of the absorber 10, and a liquid stream 16 enters the top portion of the absorber 10. The liquid stream 16 is distributed over the top of the packing (not shown) in the middle portion of the absorber 10 by a distributor (not shown). The liquid stream 16 wets the surfaces of the packing and flows downward through the absorber 10 while the $CO_2$ gas stream 14 flows upward through the interstices in the packing countercurrent to the flow of the liquid. The packing provides an area of contact between the liquid and gas phases, and includes carbonic anhydrase immobilized on its outer surface. The $CO_2$ in the gas stream is absorbed by the liquid, and the treated gas stream 18 leaves the top of the absorber. The liquid is enriched in $CO_2$ as it flows down the column, bicarbonate is formed, and the treated liquid stream 20 leaves the bottom of the absorber. The treated liquid stream 20 is pumped to a top portion of the desorber 12, and is distributed by a distributor (not shown) over packing having carbonic anhydrase immobilized thereon. The bicarbonate within the liquid stream 20 is converted to carbon dioxide, water and carbonate. Reaction rates of this reaction to produce $CO_2$ can be increased by adding heat and by increasing the rate of removal of $CO_2$ from the desorber 12 by operating at below atmospheric pressure. The water and carbonate can be recycled and combined with the liquid stream 16 entering the absorber 10, and the carbon dioxide leaves the top of the desorber as gas stream 22 and can be further processed as desired.

Alternatively, the absorber can have carbonic anhydrase immobilized on standard reactor packing materials (such as Berl saddle, Intalox saddle, Raschig ring or Pall ring packings commonly used in packed towers) and can be contacted with a microbubble $CO_2$ gas and an aqueous carbonate solution to allow for increased surface area between the gas and liquid for transport of the $CO_2$ gas into the aqueous carbonate solution.

Figure 2B:
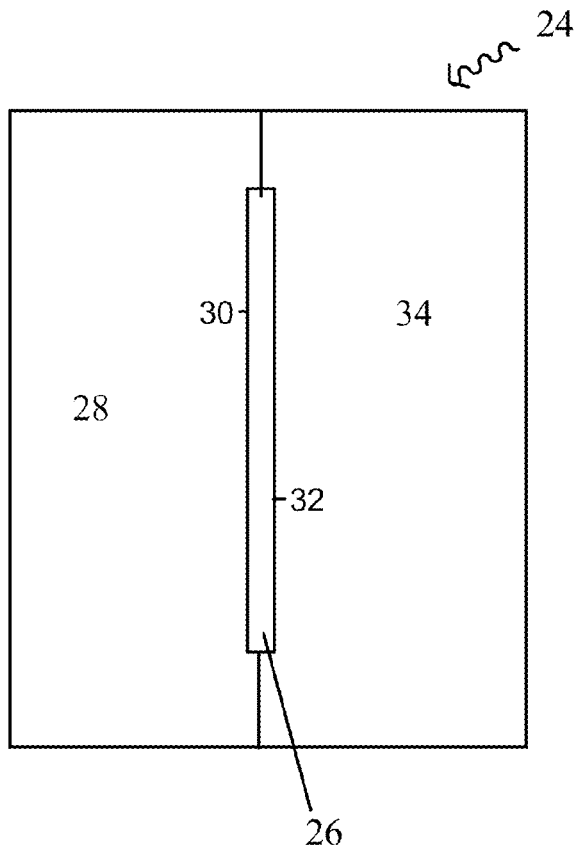

In other embodiments, the system includes a reactor 24 as shown in FIG. 2B having a membrane 26 wherein a gas stream 28 containing $CO_2$ is in contact with a first surface 30 of the membrane and an aqueous carbonate stream 34 is on a second surface 32 of the membrane. The membrane is permeable to at least the $CO_2$ gas, but is either impermeable to the aqueous carbonate stream 34 or the first surface 30 is impermeable to the stream 34. The membrane 26 can support an immobilized carbonic anhydrase as described herein. The $CO_2$ gas in the gas stream 28 can interact with the immobilized carbonic anhydrase and the stream 34 and be converted to bicarbonate. The bicarbonate can be absorbed by the stream 34 in contact with the immobilized enzyme. The membrane material can be a polysaccharide, an ion exchange resin, a treated silicon oxide, a porous metal structure, a carbon rod or tube, a graphite fiber, a silica bead, a cellulose membrane, a gel matrix (e.g., a polyacrylamide gel, a poly (acryloyl morpholine) gel, a nylon mesh and the like). High surface area/volume membrane systems that can be used in this configuration are disclosed in U.S. Pat. No. 6,524,843.

The desorber can have carbonic anhydrase immobilized on standard reactor packing materials and a feed of bicarbonate solution from the absorber. Reaction rates of this reaction to produce $CO_2$ can be increased by adding heat and the removal of $CO_2$ from the desorber could be increase by operating at below atmospheric pressure.

These system designs can be combined in different configurations depending on the specific application or gas stream to be treated. For example, the system specifications can be tailored to the $CO_2$ content of the feed stream and the overall purity, recovery, and contaminant levels required for the product streams along with the temperature and pressure requirements of both streams. The use of immobilized enzymes increases the range of system operating conditions as compared to the corresponding free enzyme. A packed tower as described herein can be used as the absorber in conjunction with a membrane reactor as described herein as the desorber. Alternatively, a membrane reactor as described herein can be used as the absorber and a packed tower as described herein can be used as the desorber.

Figure 3A:
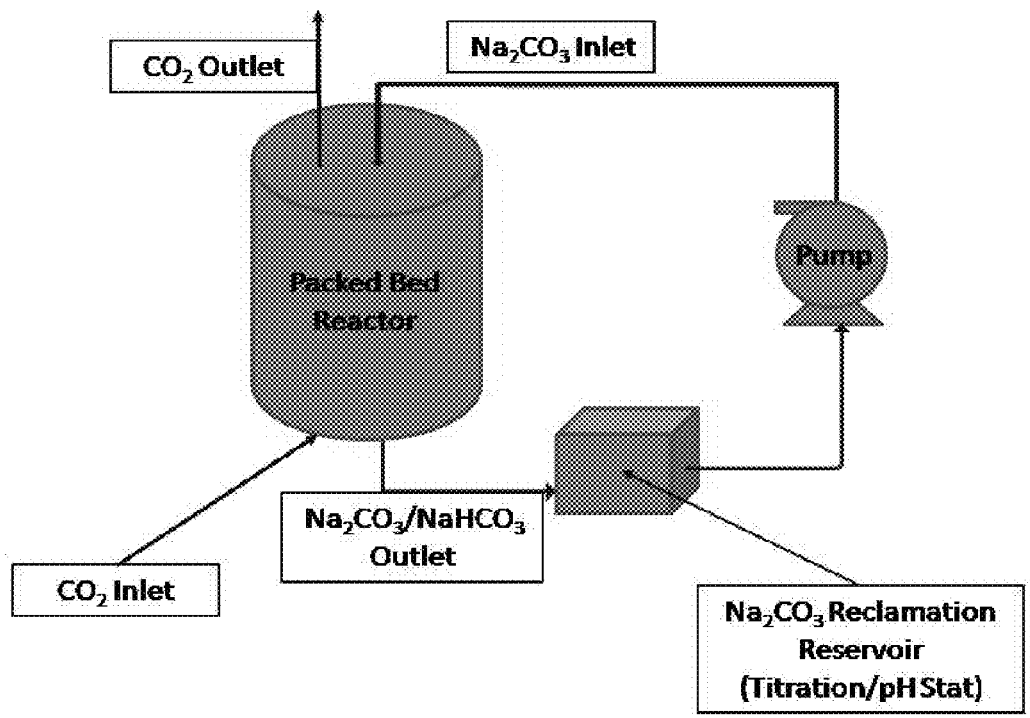
FIG. 3A is a schematic of the packed bed reactor used to collect the data presented in Example 1.
Figure 3B:
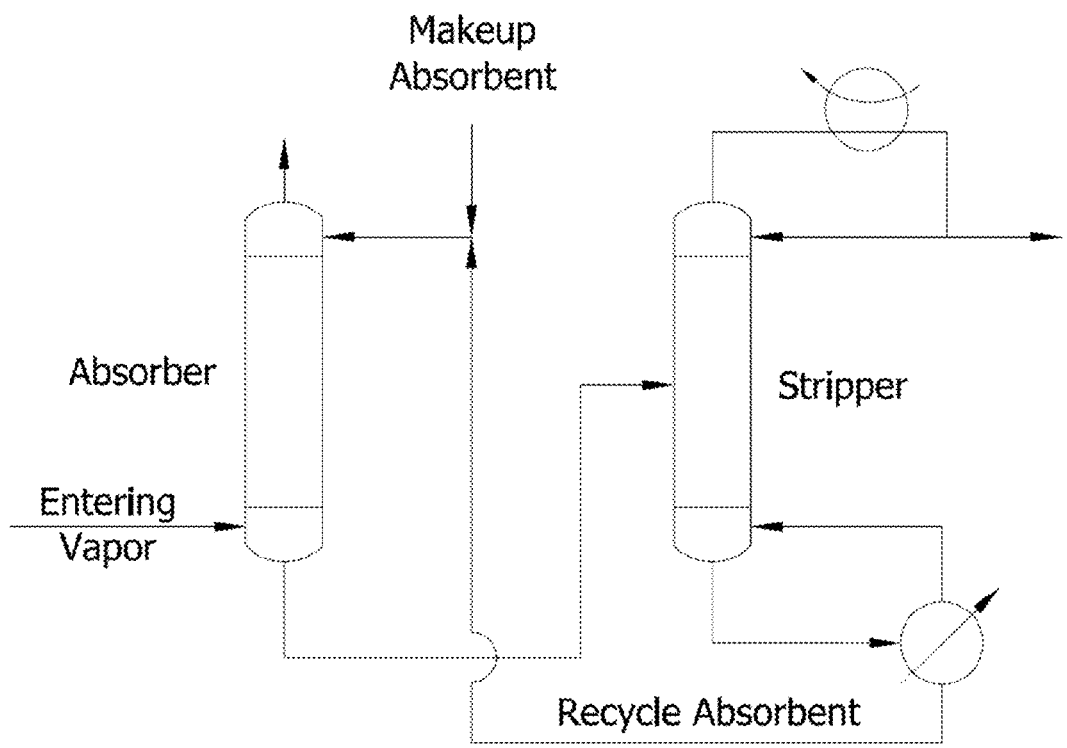
FIG. 3B is a schematic of a carbon capture system having an absorber and a stripper.

Also, the system design can be generally as depicted in FIG. 3B. For example, the carbon capture process unit comprises a standard absorption unit and a stripping (reactive distillation) unit. The core components of the carbon capture system (CCS) are an absorbing unit operation, a stripping unit operation, and a heat exchange component between the two unit operations. Peripheral equipment could include standard control hardware and software, flow monitoring and regulation (e.g., control valves, flow meters), pumps, pH monitoring (e.g., pH meters), temperature monitoring (e.g., temperature monitors), or any combination thereof. The additional equipment could provide means for monitoring and controlling the process.

Carbonic Anhydrase

The carbonic anhydrase (CA) used in the systems described herein catalyze the conversion of carbon dioxide to bicarbonate ions and protons and the conversion of bicarbonate ions and protons to carbon dioxide. Several forms of carbonic anhydrase exist in nature. Carbonic anhydrase is found in mammals, plants, algae, and bacteria. The enzymes are usually divided into three classes (e.g., alpha, beta, and gamma carbonic anhydrase). Mammalian carbonic anhydrases belong to the alpha class, plant carbonic anhydrases belong to the beta class, and carbonic anhydrases from methane-producing bacteria that grow in hot springs belong to the gamma class. Members of different classes do not have sequence or structural similarity, but perform the same function and require a zinc ion at the active site.

For mammalian carbonic anhydrase, there are at least 14 isoforms known. These mammalian CA enzymes are divided into four broad subgroups depending on the tissue or cellular compartment location (e.g., cytosolic, mitochondrial, secreted, and membrane-associated). The CA known to have the fastest turnover rate is CA II. CA IV is known to have particularly high temperature stability and this stability is believed to stem from the two disulfide linkages in the enzyme.

In some of the preferred embodiments, bovine carbonic anhydrase II or human carbonic anhydrase IV is used. Human carbonic anhydrase IV is available from William S. Sly at St. Louis University and is described in more detail in the following references: T. Okuyama, S Sato, X. L. Zhu, A. Waheed, and W. S. Sly, Human carbonic anhydrase IV: cDNA cloning, sequence comparison, and expression in COS cell membranes, *Proc. Natl. Acad. Sci. USA* 1992, 89(4), 1315-1319 and T. Stams, S. K. Nair, T. Okuyama, A. Waheed, W. S. Sly, D. W. Christianson, Crystal structure of the secretory form of membrane-associated human carbonic anhydrase IV at 2.8-Å resolution, *Proc. Natl. Acad. Sci. USA* 1996, 93, 13589-13594.

Compounds that mimic the active site of carbonic anhydrase can also be used. For example, various metal complexes have been used to mimic the carbonic anhydrase active site. For example, $[Zn_2(3,6,9,12,20,23,26,29\text{-octaazatricyclo}[29.3.1.1^{14,18}]\text{hexatriaconta-}[(34), 14,16,18(36),31(35),32\text{-hexaene})(CO_3)]Br_2 \cdot 7H_2O$ and $[Zn_2(3,6,9,12,20,23,26,29\text{-octaazatricyclo}[29.3.1.1^{14,18}]\text{hexatriaconta-1}(34), 14,16,18(36),31(35),32\text{-hexaene})(CO_3)]Br_2 \cdot 0.5CH_3COCH_3 \cdot 5H_2O$ (See Qi et al., Inorganic Chemistry Communications 2008, 11, 929-934). Also used as a mimic for carbonic anhydrase was $[tris(2\text{-benzimidazolylmethyl})amineZn(OH)_2]^{2+}$, $[tris(2\text{-benzimidazolyl})amineZn(OH)_2](ClO_4)_2$, and $[tris(hydroxy\text{-}2\text{-benzimidazolylmethyl})amineZn(OH)_2]ClO_4 \cdot 1.5H_2O$ were also used to hydrate $CO_2$. (See Nakata et al., The Chemistry Letters, 1997, 991-992 and Echizen et al., Journal of Inorganic Biochemistry 2004, 98, 1347-1360)

Enzymes and Enzyme Modifications

Enzymes including carbonic anhydrase or other enzymes can be modified and immobilized using the methods and material described herein. An enzyme is used to catalyze a desired reaction. Generally, naturally-occurring enzymes, man-made enzymes, artificial enzymes and chemically or genetically modified naturally-occurring enzymes can be immobilized. In addition, engineered enzymes that have been engineered by natural or directed evolution can be used. Stated another way, an organic or inorganic molecule that mimics an enzyme's properties can be used in embodiments of the present invention. The enzymes that can be immobilized are oxidoreductases, transferases, hydrolases, lyases, isomerases, ligases, or combinations thereof. Other enzymes that can be used can be obtained by commonly used recombinant genetic methods such as error-prone PCR and gene shuffling. Furthermore, other suitable enzymes may be obtained by the mining of enzymes from various environments such as in soil. Additionally, new enzymes and forms of enzymes can be found in microorganisms or other living sources in the environment.

In various preferred embodiments, enzymes immobilized are lipases, glucose isomerases, nitrilases, glucose oxidases, proteases (e.g., pepsin), amylases (e.g., fungal amylase, maltogenic amylase), cellulases, lactases, esterases, carbohydrases, hemicellulases, pentosanases, xylanases, pullulanases, β-glucanases, acetolactate decarboxylases, β-glucosidases, glutaminases, penicillin acylases, chloroperoxidases, aspartic β-decarboxylases, cyclodextrin glycosyltransferases, subtilisins, aminoacylases, alcohol dehydrogenases, amino acid oxidases, phospholipases, ureases, cholesterases, desulfinases, lignin peroxidases, pectinases, oxidoreductases, dextranases, glucosidases, galactosidases, glucoamylases, maltases, sucrases, invertases, naringanases, bromelain, ficin, papain, pepsins, peptidases, chymosin, thermolysins, trypsins, triglyceridases, pregastric esterases, phosphatases, phytases, amidases, glutaminases, lysozyme, catalases, dehydrogenases, peroxidases, lyases, fumarases, histidases, aminotransferases, ligases, cyclases, racemases, mutases, oxidases, reductases, ligninases, laccases, listed above, haloperoxidases, hydrogenases, nitrogenases, oxynitrilases (mandelonitrile lyases), or combinations thereof.

In various embodiments, the enzyme catalyzes reactions wherein glucose is produced. In one system, β-glucosidase can be used to hydrolyze cellobiose to glucose. Further, cellulases catalyze the hydrolysis of cellulose to glucose and amylases catalyze the hydrolysis of starch or maltose to glucose. Complex carbohydrates are the most abundant biological molecules and are a good source of substrate, but glucose has a wider range of uses than complex carbohydrates, so the carbohydrates are preferably broken down to low-molecular weight components, like glucose. Cellulose is the most abundant complex carbohydrate and it is formed from glucose sub-units. It is easily broken down by cellulases that hydrolyze the glycosidic bonds. Bioreforming of complex substrates to their low-molecular weight components can be achieved by catalysis with enzymes. These enzymes can be used for the digestion of polysaccharides (starch and cellulose) and disaccharides (sucrose and lactose) to individual carbohydrates that can be used in a larger number of reactions.

In other preferred embodiments, a carbonic anhydrase can be immobilized. Carbonic anhydrase can be used to catalyze the conversion of carbon dioxide to carbonic acid (e.g., bicarbonate and a proton in aqueous solution) or the conversion of bicarbonate and a proton to carbon dioxide.

For purposes of this application, the term "modification" means that various functional groups on the enzyme's surface interact covalently, ionically, or by hydrophobic or hydrophilic association with various modifying agents. Covalent modifications to various enzymes can be made by reaction of the enzyme with a hydrophobic agent, a hydrophilic agent, or an amphiphilic agent. These interactions add a hydrophobic, hydrophilic, or amphiphilic moiety to the enzyme. Various hydrophobic agents can be used, for example, a monoamine (e.g., alkyl amine), an aldehyde (e.g., pentanal, isobutanal, acetanal, hexanal, octanal, decanal), a quaternary ammonium salt, an alkyltrimethylammonium cation, an organic cation, a phosphonium cation, a pyridinium cation, an imidazolium cation, a viologen, a bis(triphenylphosphine)iminium metal complex, a bipyridyl metal complex, a phenanthroline-based metal complex, or a combination thereof. In various embodiments, the hydrophobic agent can be butyl amine, hexyl amine, octyl amine, decyl amine, dodecyl amine, pentanal, isobutanal, acetanal, hexanal, octanal, decanal, acetyltrimethylammonium bromide, sodium dodecyl sulfate, ammonium lauryl sulfate, triphenylphosphonium, hexadecylpyridinium, ethidium, methyl viologen, benzyl viologen, [Ru(bipyridine)$_3$]$^{2+}$, [Fe(phenanthroline)$_3$]$^{3+}$, or a combination thereof. In other embodiments, the hydrophobic agent can be butyl amine, hexyl amine, octyl amine, decyl amine, dodecyl amine, pentanal, isobutanal, acetanal, hexanal, octanal, decanal, acetyltrimethylammonium bromide, sodium dodecyl sulfate, ammonium lauryl sulfate, triphenylphosphonium, hexadecylpyridinium, ethidium, methyl viologen, benzyl viologen, or a combination thereof.

Further, hydrophilic agents can be used, for example, a diamine (e.g., ethylene diamine), a monocarboxylate, a diacid (e.g., suberic acid), a polyal, a polysaccharide, a polyacrylate, a polyacrylamide, a glycosyl, an anhydride (e.g., succinic anhydride, pyromellitic anhydride, glyceric aldehyde), a polyethylene glycol, agarose, or a combination thereof. Also, various amphiphilic modifying agents can be used, for example, an amino acid, fatty acids, fatty alcohols, lipids, alkyl polyethylene oxide, other polyethylene oxide copolymers, alkyl polyglucosides, or a combination thereof. Further, the surface active agents described below could be used to modify the enzymes as well. The agents for covalent modification have a functional group that is or can be made reactive with a functional group of the enzyme being modified. Further, the enzyme can be glycosylated by using an appropriate expression system or by in vitro glycosylation wherein a saccharide moiety is attached to the enzyme.

In various preferred embodiments, the enzyme is carbonic anhydrase wherein the enzyme has been covalently modified with either an alkyl amine or a water soluble polymer such as polyethylene glycol, an ethylene glycol/propylene glycol copolymer, carboxymethylcellulose, dextran, polyvinyl alcohol, and the like. Alkyl amines useful for covalent modification are butyl amine, hexyl amine, octyl amine, decyl amine, dodecyl amine, and the like.

The enzymes may be modified at random positions within the molecule, or at predetermined positions within the molecule and may include one, two, three or more attached chemical moieties.

The water soluble polymer can be of any molecular weight, and can be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired properties, particularly, biological activity. For example, the polyethylene glycol may have a mass average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa. In various embodiments, the polyethylene glycol can have a mass average molecular weight from about 200 Da to about 900 Da, from about 300 Da to about 800 Da, from about 400 Da to about 700 Da, from about 500 Da to about 600 Da, or a mass average molecular weight of about 550 Da.

As noted above, the polyethylene glycol may have a branched structure. Branched polyethylene glycols are described, for example, in U.S. Pat. No. 5,643,575; Morpurgo et al, Appl. Biochem. Biotechnol. 56:59-72 (1996); Vorobjev et al., Nucleosides Nucleotides 18:2745-2750 (1999); and Caliceti et al., Bioconjug. Chem. 10:638-646 (1999), the disclosures of each of which are incorporated herein by reference.

The polyethylene glycol molecules (or other chemical moieties) should be attached to the enzyme with consideration of effects on functional domains of the enzyme. There are a number of attachment methods available to those skilled in the art, e.g., EP 0 401 384, herein incorporated by reference (coupling PEG to G-CSF), see also Malik et al., Exp. Hematol. 20:1028-1035 (1992) (reporting PEGylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine, arginine, asparagine, and glutamine residues and the N-terminal amino acid residues; those having a free carboxyl group may include aspartic acid residues, glutamic acid residues and the C-terminal amino acid residue. Sulfhydryl groups may also be used as a reactive group for attaching the polyethylene glycol molecules.

As suggested above, polyethylene glycol may be attached to enzymes via linkage to any of a number of amino acid residues. For example, polyethylene glycol can be linked to an enzyme via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) of the enzyme or to more than one type of amino acid residue (e.g., lysine, histidine, aspartic acid, glutamic acid, cysteine and combinations thereof) of the enzyme.

As indicated above, PEGylation of the enzymes may be accomplished by any number of means. For example, polyethylene glycol may be attached to the enzyme either directly or by an intervening linker. Linkerless systems for attaching polyethylene glycol to enzymes are described in Delgado et al., Crit. Rev. Thera. Drug Carrier Sys. 9:249-304 (1992); Francis et al., Inter J. of Hematol. 68:1-18 (1998); U.S. Pat. No. 4,002,531; U.S. Pat. No. 5,349,052; WO 95/06058; and WO 98/32466, the disclosures of each of which are incorporated herein by reference.

One system for attaching polyethylene glycol directly to amino acid residues of enzymes without an intervening linker employs tresylated MPEG, which is produced by the modification of monomethoxy polyethylene glycol (MPEG) using tresylchloride ($ClSO_2CH_2CF_3$). Upon reaction of the enzyme with tresylated MPEG, polyethylene glycol is directly attached to amine groups of the enzyme. Thus, the invention includes enzyme-polyethylene glycol conjugates produced by reacting enzymes of the invention with a polyethylene glycol molecule having a 2,2,2-trifluoroethane sulfonyl group.

Polyethylene glycol can also be attached to enzymes using a number of different intervening linkers. For example, U.S. Pat. No. 5,612,460, the entire disclosure of which is incorporated herein by reference, discloses urethane linkers for connecting polyethylene glycol to enzymes. Enzyme-polyethylene glycol conjugates wherein the polyethylene glycol is attached to the enzyme by a linker can also be produced by reaction of enzymes with compounds such as MPEG-succinimidylsuccinate, MPEG activated with 1,1'-carbonyldiimidazole, MPEG-2,4,5-trichloropenylcarbonate, MPEG-p-nitrophenolcarbonate, and various MPEG-succinate derivatives. A number of additional polyethylene glycol derivatives and reaction chemistries for attaching polyethylene glycol to enzymes are described in WO 98/32466, the entire disclosure of which is incorporated herein by reference.

The number of polyethylene glycol moieties attached to each enzyme (i.e., the degree of substitution) may also vary. For example, the PEGylated enzymes may be linked, on average, to 1, 2, 3, 4, 5, 6, 7, 8, 9, 10, 12, 15, 17, 20, or more polyethylene glycol molecules. Similarly, the average degree of substitution ranges from 1-3, 2-4, 3-5, 4-6, 5-7, 6-8, 7-9, 8-10, 9-11, 10-12, 11-13, 12-14, 13-15, 14-16, 15-17, 16-18, 17-19, or 18-20 polyethylene glycol moieties per enzyme molecule. Methods for determining the degree of substitution are discussed, for example, in Delgado et al., Crit. Rev. Thera. Drug Carrier Sys. 9:249-304 (1992).

When an amine is used to modify the enzyme, the enzyme is combined with a coupling agent (e.g., N-(3-dimethylaminopropyl)-N-ethylcarbodiimide hydrochloride (EDC), dicyclohexylcarbodiiminde (DCC), N,N'-diisopropylcarbodiimide (DIC)) and an ester activating agent (e.g., N-hydroxysulfosuccinimide sodium salt (Sulfo-NHS)), 1-hydroxybenzotriazole, 1-hydroxy-7-azabenzotrizole); the resulting solution is vigorously vortexed for five seconds. A second solution is made with a MES buffer of pH 5.0 combined with an alkyl amine or a polyethylene glycol. This solution is combined with the coupling agent/enzyme solution and vigorously vortexed for 5 seconds. The combined solutions are held refrigerated overnight. Then the modified enzyme can be immobilized in the immobilization materials described herein.

Further, the enzymes can be modified by various surface active agents. For example, non-ionic surface active agents can be N,N-bis(3-D-gluconamidopropyl)cholamide (BigCHAP), N,N-bis(3-D-gluconamidopropyl)deoxycholamide (DeoxyBigCHAP), a polyoxyethylene alcohol (e.g., Brij35 and Brij 58 P), 2-cyclohexylmethyl-β-D-maltoside (Cymal-1), 2-cyclohexylethyl-β-D-maltoside (Cymal-2), cyclohexylpentyl-3-D-maltoside (Cymal-5), cyclohexylhexyl-β-D-maltoside(Cymal-6), decyl-β-D-maltopyranoside, n-dodecyl-β-D-maltoside, n-hexyadecyl-β-D-maltoside, undecyl-β-D-maltoside, decyl-β-D-1-thiomaltopyranoside, octyl-3-D-thioglucopyranoside, digitonin, dimethydecylphosphine oxide, dodecyldimethylphosphine oxide, (octylphenoxy)polyethoxyethanol (IGEPAL® CA630), N-octanoyl-N-methylglucamine (MEGA-8), N-nonanoyl-N-methylglucamine (MEGA-9), N-decanoyl-N-methylglucamine (MEGA-10), a polyoxy ethylene octyl phenol (Nonidet® P40-substitute), a polyoxyethylene-polyoxypropylene block co-polymer (Pluronic F-68), saponin, polyoxyethylene 9-lauryl ether (Thesit®), a polyoxy ethylene octyl phenol (e.g., Triton® X-100 and Triton® X-114), a polyoxyethylene derivative of sorbitan monolaurate (e.g., TWEEN® 20, TWEEN® 40, and TWEEN® 80), N,N-dimethyldodecylamine-N-oxide, an alcohol ethoxylate (Synperonic A7), or a combination thereof.

Zwitterionic surface active agents can also be used, for example amidosulfobetaine-14, amidosulfobetaine-16, C7BzO, 3-[(3-cholamidopropyldimethylammonio]-1-propanesulphonate (CHAPS), 3-[(3-cholamidopropyldimethylammonio]-2-hydroxy-1-propanesulphonate (CHAPSO), (dodecyldimethylammonio)acetate (EMPIGEN® BB), 3-(N,N-dimethyloctylammonio) propanesulfonate, 3-(dodecylammonio)propanesulfonate, 3-(N,N-dimethylmyristylammonio) propanesulfonate, 3-(N,N-dimethylpalmitylammonio) propanesulfonate, 3-(N,N-dimethyloctadecylammonio) propanesulfonate, or a combination thereof.

When the enzyme is modified with a surface active agent, the modified enzyme is prepared by combining the enzyme with a surface active agent in a buffer of the appropriate pH for the enzyme. One of ordinary skill in the art could readily determine buffers of appropriate pH for a particular enzyme.

Enzyme Immobilization Materials

For purposes of the present invention, an enzyme is "stabilized" if it either: (1) retains at least about 15% of its initial catalytic activity for at least about 30 days when continuously catalyzing a chemical transformation at room temperature; (2) retains at least about 15% of its initial catalytic activity for at least about 5 days when continuously catalyzing a chemical transformation at room temperature; (3) retains at least about 15% of its initial catalytic activity for at least about 5 days when being treated at temperatures from about 30° C. to about 100° C., (4) retains at least about 15% of its initial catalytic activity for at least about 5 days when continuously catalyzing a chemical transformation at room temperature and a pH from about 0 to about 13, (5) retains at least about 15% of its initial catalytic activity for at least about 5 days when continuously catalyzing a chemical transformation at room temperature in a non-polar solvent, an oil, an alcohol, acetonitrile, or a high ion concentration. Typically, a free enzyme in solution loses its catalytic activity within a few hours to a few days, whereas a properly immobilized and stabilized enzyme can retain its catalytic activity for at least about 5 days to about 1095 days (3 years). Thus, the immobilization of the enzyme provides a significant advantage in stability. The retention of catalytic activity is defined as the enzyme having at least about 15% of its initial activity, which can be measured by a means that demonstrate enzyme-mediated generation of product such as chemiluminescence, electrochemical, mass spectrometry, spectrophotometric (i.e. UV-Vis), radiochemical, or fluorescence assay wherein the intensity of the property is measured at an initial time. In various embodiments, the enzyme retains at least about 15% of its initial activity while the enzyme is continuously catalyzing a chemical transformation.

With respect to the stabilization of the enzyme, the enzyme immobilization material provides a chemical and/or mechanical barrier to prevent or impede enzyme denaturation. To this end, the enzyme immobilization material physically confines the enzyme, preventing the enzyme from unfolding. The process of unfolding an enzyme from a folded three-dimensional structure is one mechanism of enzyme denaturation.

In some embodiments, the enzyme immobilization material stabilizes the enzyme so that the enzyme retains its catalytic activity for at least about 5 days to about 730 days (2 years). In other embodiments, the immobilized enzyme retains at least about 75% of its initial catalytic activity for at least about 30, 45, 60, 75, 90, 105, 120, 150, 180, 210, 240, 270, 300, 330, 365, 400, 450, 500, 550, 600, 650, 700, 730, 800, 850, 900, 950, 1000, 1050, 1095 days or more. In some instances, the immobilized enzyme retains about 75% to about 95% of its initial catalytic activity for about 30 to about 1095 days, about 45 to about 1095 days, about 60 to about 1095 days, about 75 to about 1095 days, about 90 to about 1095 days, about 105 to about 1095 days, about 120 to about 1095 days, about 150 to about 1095 days, about 180 to about 1095 days, about 210 to about 1095 days, about 240 to about 1095 days, about 270 to about 1095 days, about 300 to about 1095 days, about 330 to about 1095 days, about 365 to about 1095 days, about 400 to about 1095 days, about 450 to about 1095 days, about 500 to about 1095 days, about 550 to about 1095 days, about 600 to about 1095 days, about 650 to about 1095 days, about 700 to about 1095 days, or about 730 to about 1095 days. In various embodiments, the immobilized enzyme retains at least about 15, 20, 25, 30, 35, 40, 45, 50, 55, 60, 65, 70, 75, 80, 85, 90 or 95% or more of its initial catalytic activity for at least about 5, 7, 10, 15, 20, 25, 30, 45, 60, 75, 90, 105, 120, 150, 180, 210, 240, 270, 300, 330, 365, 400, 450, 500, 550, 600, 650, 700, 730, 800, 850, 900, 950, 1000, 1050, 1095 days or more. In some instances, the immobilized enzyme retains about 15 to about 95%, about 20 to about 95%, about 25 to about 95%, about 30 to about 95%, about 35 to about 95%, about 40 to about 95%, about 45 to about 95%, about 50 to about 95%, about 55 to about 95%, about 60 to about 95%, about 65 to about 95%, about 70 to about 95%, about 75 to about 95%, about 80 to about 95%, about 85 to about 95%, or about 90 to about 95% of its initial catalytic activity for about 5 to about 1095 days, about 7 to about 1095 days, about 10 to about 1095 days, about 15 to about 1095 days, about 20 to about 1095 days, about 25 to about 1095 days, about 30 to about 1095 days, about 45 to about 1095 days, about 60 to about 1095 days, about 75 to about 1095 days, about 90 to about 1095 days, about 105 to about 1095 days, about 120 to about 1095 days, about 150 to about 1095 days, about 180 to about 1095 days, about 210 to about 1095 days, about 240 to about 1095 days, about 270 to about 1095 days, about 300 to about 1095 days, about 330 to about 1095 days, about 365 to about 1095 days, about 400 to about 1095 days, about 450 to about 1095 days, about 500 to about 1095 days, about 550 to about 1095 days, about 600 to about 1095 days, about 650 to about 1095 days, about 700 to about 1095 days, or about 730 to about 1095 days.

In various embodiments, an enzyme having greater temperature or pH stability may also retain at least about 75% of its initial catalytic activity for at least about 5 days when actively catalyzing a chemical transformation as described above.

In other embodiments, when exposed to a pH of less than about 2, less than about 3, less than about 4, or less than about 5, the stabilized enzyme retains at least about 15, 20, 25, 30, 35, 40, 45, 50, 55, 60, 65, 70, 75, 80, 85, 90 or 95% of its initial catalytic activity for at least about 5, 10, 15, 30, 40, 50, 60, 75, 90 days or more when continuously catalyzing a chemical transformation. In some instances, when exposed to a pH of less than about 2, less than about 3, less than about 4, or less than about 5, the stabilized enzyme retains about 15 to about 95%, about 20 to about 95%, about 25 to about 95%, about 30 to about 95%, about 35 to about 95%, about 40 to about 95%, about 45 to about 95%, about 50 to about 95%, about 55 to about 95%, about 60 to about 95%, about 65 to about 95%, about 70 to about 95%, about 75 to about 95%, about 80 to about 95%, about 85 to about 95%, or about 90 to about 95% of its initial catalytic activity for about 5 to 90 days, about 10 to 90 days, about 15 to 90 days, about 20 to 90 days, about 25 to 90 days, about 30 to 90 days, about 35 to 90 days, about 40 to 90 days, about 45 to 90 days, about 50 to 90 days, about 55 to 90 days, about 60 to 90 days, about 65 to 90 days, about 70 to 90 days, about 75 to 90 days, about 80 to 90 days, about 85 to 90 days when continuously catalyzing a chemical transformation. In some instances, when exposed to a pH of less than about 2, less than about 3, less than about 4, or less than about 5, the stabilized enzyme retains about 15 to about 95%, about 20 to about 95%, about 25 to about 95%, about 30 to about 95%, about 35 to about 95%, about 40 to about 95%, about 45 to about 95%, about 50 to about 95%, about 55 to about 95%, about 60 to about 95%, about 65 to about 95%, about 70 to about 95%, about 75 to about 95%, about 80 to about 95%, about 85 to about 95%, or about 90 to about 95% of its initial catalytic activity for at least about 5, 10, 15, 30, 40, 50, 60, 75, 90 days or more when continuously catalyzing a chemical transformation. In some instances, when exposed to a pH of greater than about 9, greater than about 10, greater than about 11, or greater than about 12, the stabilized enzyme retains about 15 to about 95%, about 20 to about 95%, about 25 to about 95%, about 30 to about 95%, about 35 to about 95%, about 40 to about 95%, about 45 to about 95%, about 50 to about 95%, about 55 to about 95%, about 60 to about 95%, about 65 to about 95%, about 70 to about 95%, about 75 to about 95%, about 80 to about 95%, about 85 to about 95%, or about 90 to about 95% of its initial catalytic activity for about 5 to 90 days, about 10 to 90 days, about 15 to 90 days, about 20 to 90 days, about 25 to 90 days, about 30 to 90 days, about 35 to 90 days, about 40 to 90 days, about 45 to 90 days, about 50 to 90 days, about 55 to 90 days, about 60 to 90 days, about 65 to 90 days, about 70 to 90 days, about 75 to 90 days, about 80 to 90 days, about 85 to 90 days when continuously catalyzing a chemical transformation.

In other embodiments, when exposed to an agent such as a nonpolar solvent, an oil, an alcohol, acetonitrile, a concentrated ionic solution, or combination thereof, the stabilized enzyme retains at least about 15, 20, 25, 30, 35, 40, 45, 50, 55, 60, 65, 70, 75, 80, 85, 90 or 95% of its initial catalytic activity for at least about 5, 10, 15, 30, 40, 50, 60, 75, 90 days or more when continuously catalyzing a chemical transformation. In some instances, when exposed to the agent, the stabilized enzyme retains about 10 to about 95%, about 15 to about 95%, about 20 to about 95%, about 25 to about 95%, about 30 to about 95%, about 35 to about 95%, about 40 to about 95%, about 45 to about 95%, about 50 to about 95%, about 55 to about 95%, about 60 to about 95%, about 65 to about 95%, about 70 to about 95%, about 75 to about 95%, about 80 to about 95%, about 85 to about 95%, or about 90 to about 95% of its initial catalytic activity for about 5 to 90 days, about 10 to 90 days, about 15 to 90 days, about 20 to 90 days, about 25 to 90 days, about 30 to 90 days, about 35 to 90 days, about 40 to 90 days, about 45 to 90 days, about 50 to 90 days, about 55 to 90 days, about 60 to 90 days, about 65 to 90 days, about 70 to 90 days, about 75 to 90 days, about 80 to 90 days, about 85 to 90 days when continuously catalyzing a chemical transformation. In these instances, the concentration of the agent can be from about 1 wt. % to about 95 wt. %, 5 wt. % to about 95 wt. %, 10 wt. % to about 95 wt. %, 15 wt. % to about 95 wt. %, 20 wt. % to about 95 wt. %, 30 wt. % to about 95 wt. %, 40 wt. % to about 95 wt. %, 50 wt. % to about 95 wt. %.

An immobilized enzyme is an enzyme that is physically confined in a certain region of the enzyme immobilization material while retaining its catalytic activity. There are a variety of methods for enzyme immobilization, including carrier-binding, cross-linking and entrapping. Carrier-binding is the binding of enzymes to water-insoluble carriers. Cross-linking is the intermolecular cross-linking of enzymes by bifunctional or multifunctional reagents. Entrapping is incorporating enzymes into the lattices of a semipermeable material. The particular method of enzyme immobilization is not critically important, so long as the enzyme immobilization material (1) immobilizes the enzyme, and in some embodiments, (2) stabilizes the enzyme. In various embodiments, the enzyme immobilization material is also permeable to a compound smaller than the enzyme. An enzyme is adsorbed to an immobilization material when it adheres to the surface of the material by chemical or physical interactions. Further, an enzyme is immobilized by entrapment when the enzyme is contained within the immobilization material whether within a pocket of the material or not.

With reference to the immobilization material's permeability to various compounds that are smaller than an enzyme, the immobilization material allows the movement of a substrate compound through it so the substrate compound can contact the enzyme. The immobilization material can be prepared in a manner such that it contains internal pores, micellar pockets, channels, openings or a combination thereof, which allow the movement of the substrate compound throughout the immobilization material, but which constrain the enzyme to substantially the same space within the immobilization material. Such constraint allows the enzyme to retain its catalytic activity. In various preferred embodiments, the enzyme is confined to a space that is substantially the same size and shape as the enzyme, wherein the enzyme retains substantially all of its catalytic activity. The pores, micellar pockets, channels, or openings have physical dimensions that satisfy the above requirements and depend on the size and shape of the specific enzyme to be immobilized.

In some of the embodiments, the enzyme is preferably located within a pore of the immobilization material and the compound travels in and out of the immobilization material through transport channels. The pores of the enzyme immobilization material can be from about 6 nm to about 30 nm, from about 10 nm to about 30 nm, from about 15 nm to about 30 nm, from about 20 nm to about 30 nm, from about 25 nm to about 30 nm, from about 6 nm to about 20 nm, or from about 10 nm to about 20 nm. The relative size of the pores and transport channels can be such that a pore is large enough to immobilize an enzyme, but the transport channels are too small for the enzyme to travel through them. Further, a transport channel preferably has a diameter of at least about 10 nm. In some embodiments, the pore diameter to transport channel diameter ratio is at least about 2:1, 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1, 10:1 or more; the pore diameter to transport channel diameter ratio can be about 2:1 to about 10:1, about 2.5:1 to about 10:1, about 3:1 to about 10:1, about 3.5:1 to about 10:1, about 4:1 to about 10:1, about 4.5:1 to about 10:1, about 5:1 to about 10:1, about 5.5:1 to about 10:1, about 6:1 to about 10:1, about 6.5:1 to about 10:1, about 7:1 to about 10:1, about 7.5:1 to about 10:1, about 8:1 to about 10:1, about 8.5:1 to about 10:1, about 9:1 to about 10:1, or about 9.5:1 to about 10:1. In yet another embodiment, preferably, a transport channel has a diameter of at least about 2 nm and the pore diameter to transport channel diameter ratio is at least about 2:1, 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1, 10:1 or more; the pore diameter to transport channel diameter ratio can be about 2:1 to about 10:1, about 2.5:1 to about 10:1, about 3:1 to about 10:1, about 3.5:1 to about 10:1, about 4:1 to about 10:1, about 4.5:1 to about 10:1, about 5:1 to about 10:1, about 5.5:1 to about 10:1, about 6:1 to about 10:1, about 6.5:1 to about 10:1, about 7:1 to about 10:1, about 7.5:1 to about 10:1, about 8:1 to about 10:1, about 8.5:1 to about 10:1, about 9:1 to about 10:1, or about 9.5:1 to about 10:1.

In some of the various embodiments, when the enzyme is large or aggregated, the enzyme immobilization material can have a pore size that is substantially the same size as the enzyme or aggregated enzyme. Such an enzyme immobilization material can have pores that constrain the enzyme or aggregated enzyme in substantially the same space within the enzyme immobilization material and allow diffusion of compounds that are smaller than the enzyme or aggregated enzyme through the material. This enzyme immobilization material would have an average micelle size of from about 15 nm to about 2000 nm, from about 50 nm to about 2000 nm, from about 100 nm to about 2000 nm, from about 200 nm to about 2000 nm, from about 300 nm to about 2000 nm, from about 400 nm to about 2000 nm, from about 500 nm to about 2000 nm, from about 600 nm to about 2000 nm, from about 700 nm to about 2000 nm, from about 800 nm to about 2000 nm, from about 20 nm to about 1000 nm, from about 50 nm to about 1000 nm, from about 100 nm to about 1000 nm, from about 200 nm to about 1000 nm, from about 300 nm to about 1000 nm, from about 400 nm to about 1000 nm, from about 500 nm to about 1000 nm, from about 600 nm to about 1000 nm, or from about 700 nm to about 1000 nm.

In some of these embodiments, the immobilization material has a micellar or inverted micellar structure. Generally, the molecules making up a micelle are amphipathic, meaning they contain a polar, hydrophilic group and a nonpolar, hydrophobic group. The molecules can aggregate to form a micelle, where the polar groups are on the surface of the aggregate and the hydrocarbon, nonpolar groups are sequestered inside the aggregate. Inverted micelles have the opposite orientation of polar groups and nonpolar groups. The amphipathic molecules making up the aggregate can be arranged in a variety of ways so long as the polar groups are in proximity to each other and the nonpolar groups are in proximity to each other. Also, the molecules can form a bilayer with the nonpolar groups pointing toward each other and the polar groups pointing away from each other. Alternatively, a bilayer can form wherein the polar groups can point toward each other in the bilayer, while the nonpolar groups point away from each other.

Modified Nafion®

In one preferred embodiment, the micellar immobilization material is a modified perfluoro sulfonic acid-PTFE copolymer (or modified perfluorinated ion exchange polymer) (modified Nafion® or modified Flemion®) membrane. The perfluorinated ion exchange polymer membrane is modified with a hydrophobic cation that is larger than the ammonium ($NH_4^+$) ion. The hydrophobic cation serves the dual function of (1) dictating the membrane's pore size and (2) acting as a chemical buffer to help maintain the pore's pH level, both of which stabilize the enzyme.

With regard to the first function of the hydrophobic cation, mixture-casting a perfluoro sulfonic acid-PTFE copolymer (or perfluorinated ion exchange polymer) with a hydrophobic cation to produce a modified perfluoro sulfonic acid-PTFE copolymer (or modified perfluorinated ion exchange polymer)(Nafion® or Flemion®) membrane provides an immobilization material wherein the pore size is dependent on the size of the hydrophobic cation. Accordingly, the larger the hydrophobic cation, the larger the pore size. This function of the hydrophobic cation allows the pore size to be made larger or smaller to fit a specific enzyme by varying the size of the hydrophobic cation.

Regarding the second function of the hydrophobic cation, the properties of the perfluoro sulfonic acid-PTFE copolymer (or perfluorinated ion exchange polymer) membrane are altered by exchanging the hydrophobic cation for protons as the counterion to the —$SO_3^-$ groups on the perfluoro sulfonic acid-PTFE copolymer (or anions on the perfluorinated ion exchange polymer) membrane. This change in counterion provides a buffering effect on the pH because the hydrophobic cation has a much greater affinity for the —$SO_3^-$ sites than protons do. This buffering effect of the membrane causes the pH of the pore to remain substantially unchanged with changing solution pH; stated another way, the pH of the pore resists changes in the solution's pH. In addition, the membrane provides a mechanical barrier, which further protects the immobilized enzymes.

In order to prepare a modified perfluoro sulfonic acid-PTFE copolymer (or perfluorinated ion exchange polymer) membrane, the first step is to cast a suspension of perfluoro sulfonic acid-PTFE copolymer (or perfluorinated ion exchange polymer), particularly Nafion®, with a solution of the hydrophobic cations to form a membrane. The excess hydrophobic cations and their salts are then extracted from the membrane, and the membrane is re-cast. Upon re-casting, the membrane contains the hydrophobic cations in association with the —SO$_3^-$ sites of the perfluoro sulfonic acid-PTFE copolymer (or perfluorinated ion exchange polymer) membrane. Removal of the salts of the hydrophobic cation from the membrane results in a more stable and reproducible membrane; if they are not removed, the excess salts can become trapped in the pore or cause voids in the membrane.

In one embodiment, a modified Nafion® membrane is prepared by casting a suspension of Nafion® polymer with a solution of a salt of a hydrophobic cation such as quaternary ammonium bromide. Excess quaternary ammonium bromide or hydrogen bromide is removed from the membrane before it is re-cast to form the salt-extracted membrane. Salt extraction of membranes retains the presence of the quaternary ammonium cations at the sulfonic acid exchange sites, but eliminates complications from excess salt that may be trapped in the pore or may cause voids in the equilibrated membrane. The chemical and physical properties of the salt-extracted membranes have been characterized by voltammetry, ion exchange capacity measurements, and fluorescence microscopy before enzyme immobilization. Exemplary hydrophobic cations are ammonium-based cations, quaternary ammonium cations, alkyltrimethylammonium cations, alkyltriethylammonium cations, organic cations, phosphonium cations, triphenylphosphonium, pyridinium cations, imidazolium cations, hexadecylpyridinium, ethidium, viologens, methyl viologen, benzyl viologen, bis(triphenylphosphine)iminium, metal complexes, bipyridyl metal complexes, phenanthroline-based metal complexes, [Ru(bipyridine)$_3$]$^{2+}$ and [Fe(phenanthroline)$_3$]$^{3+}$.

In one preferred embodiment, the hydrophobic cations are ammonium-based cations. In particular, the hydrophobic cations are quaternary ammonium cations. In another embodiment, the quaternary ammonium cations are represented by Formula 1:

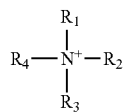

wherein R$_1$, R$_2$, R$_3$, and R$_4$ are independently hydrogen, hydrocarbyl, substituted hydrocarbyl, or heterocyclo wherein at least one of R$_1$, R$_2$, R$_3$, and R$_4$ is other than hydrogen. In a further embodiment, preferably, R$_1$, R$_2$, R$_3$, and R$_4$ are independently hydrogen, methyl, ethyl, propyl, butyl, pentyl, hexyl, heptyl, octyl, nonyl, decyl, undecyl, dodecyl, tridecyl or tetradecyl wherein at least one of R$_1$, R$_2$, R$_3$, and R$_4$ is other than hydrogen. In still another embodiment, R$_1$, R$_2$, R$_3$, and R$_4$ are the same and are methyl, ethyl, propyl, butyl, pentyl or hexyl. In yet another embodiment, preferably, R$_1$, R$_2$, R$_3$, and R$_4$ are butyl. In yet another embodiment, preferably, R$_1$, R$_2$, R$_3$, and R$_4$ are ethyl. Preferably, the quaternary ammonium cation is tetraethylammonium (T2A), tetrapropylammonium (T3A), tetrapentylammonium (T5A), tetrahexylammonium (T6A), tetraheptylammonium (T7A), trimethylicosylammonium (TMICA), trimethyloctyldecylammonium (TMODA), trimethylhexyldecylammonium (TMHDA), trimethyltetradecylammonium (TMTDA), trimethyloctylammonium (TMOA), trimethyldodecylammonium (TMDDA), trimethyldecylammonium (TMDA), trimethylhexylammonium (TMHA), tetrabutylammonium (TBA), triethylhexylammonium (TEHA), and combinations thereof.

Carbonic anhydrase can be immobilized in TEAB-modified Nafion® as follows. Tetraethyl ammonium bromide (TEAB) modified Nafion® is added to ethanol to make a solution having a concentration of 5.0 wt. %. The carbonic anhydrase is added to a buffer solution and a surface active agent is added at a total solution percentage of 0.5% and stirred until a uniform dissolution occurs. Once the solution is adequately dispersed, the TEAB-modified Nafion® solution is added and stirred until the solution is sufficiently homogenous. Once the immobilized enzyme solution is thoroughly mixed, it is cast onto a high surface area support and allowed to dry for 12 hours at 4° C. followed by two hours under vacuum. Alternatively, a high surface carbon support can be added to the immobilized enzyme solution, mixed, sprayed, and allowed to dry for several hours at room temperature.

Hydrophobically Modified Polysaccharides

In other various embodiments, exemplary micellar or inverted micellar immobilization materials are hydrophobically modified polysaccharides, these polysaccharides are selected from chitosan, cellulose, chitin, starch, amylose, alginate, glycogen, and combinations thereof. In various embodiments, the micellar or inverted micellar immobilization materials are polycationic polymers, particularly, hydrophobically modified chitosan. Chitosan is a poly[β-1-(1-4)-2-amino-2-deoxy-D-glucopyranose]. Chitosan is typically prepared by deacetylation of chitin (a poly[β1-(1-4)-2-acetamido-2-deoxy-D-glucopyranose]). The typical commercial chitosan has approximately 85% deacetylation. These deacetylated or free amine groups can be further functionalized with hydrocarbyl, particularly, alkyl groups. Thus, in various embodiments, the micellar hydrophobically modified chitosan corresponds to the structure of Formula 2

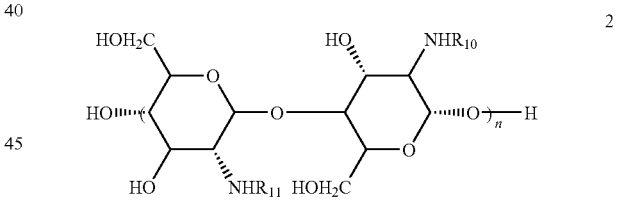

wherein n is an integer; R$_{10}$ is independently hydrogen, hydrocarbyl, substituted hydrocarbyl, or a hydrophobic redox mediator; and R$_{11}$ is independently hydrogen, hydrocarbyl, substituted hydrocarbyl, or a hydrophobic redox mediator. In certain embodiments of the invention, n is an integer that gives the polymer a molecular weight of from about 21,000 to about 4,000,000; from about 21,000 to about 500,000; preferably, from about 90,000 to about 500,000; more preferably, from about 150,000 to about 350,000; more preferably, from about 225,000 to about 275,000. In many embodiments, R$_{10}$ is independently hydrogen or alkyl and R$_{11}$ is independently hydrogen or alkyl. Further, R$_{10}$ is independently hydrogen or hexyl and R$_{11}$ is independently hydrogen or hexyl. Alternatively, R$_{10}$ is independently hydrogen or octyl and R$_{11}$ is independently hydrogen or octyl.

In other various embodiments, the micellar hydrophobically modified chitosan is a micellar hydrophobic redox mediator modified chitosan corresponding to Formula 2A

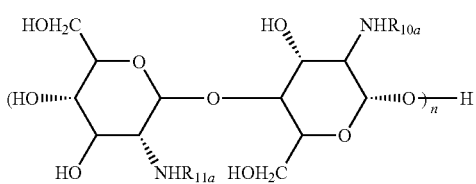

wherein n is an integer; $R_{10a}$ is independently hydrogen, or a hydrophobic redox mediator; and $R_{11a}$ is independently hydrogen, or a hydrophobic redox mediator.

Further, in various embodiments, the micellar hydrophobically modified chitosan is a modified chitosan or redox mediator modified chitosan corresponding to Formula 2B

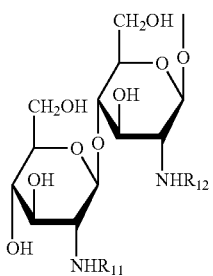

wherein $R_{11}$, $R_{12}$, and n are defined as in connection with Formula 2. In some embodiments, $R_{11}$ and $R_{12}$ are independently hydrogen or straight or branched alkyl; preferably, hydrogen, butyl, pentyl, hexyl, heptyl, octyl, nonyl, decyl, undecyl, or dodecyl. In various embodiments, $R_{11}$ and $R_{12}$ are independently hydrogen, butyl, or hexyl.

The micellar hydrophobically modified chitosans can be modified with hydrophobic groups to varying degrees. The degree of hydrophobic modification is determined by the percentage of free amine groups that are modified with hydrophobic groups as compared to the number of free amine groups in the unmodified chitosan. The degree of hydrophobic modification can be estimated from an acid-base titration and/or nuclear magnetic resonance (NMR), particularly $^1$H NMR, data. This degree of hydrophobic modification can vary widely and is at least about 0.25, 0.5, 1, 2, 4, 6, 8, 10, 12, 14, 16, 18, 20, 25, 30, 32, 24, 26, 28, 40, 42, 44, 46, 48%, or more. Preferably, the degree of hydrophobic modification is from about 10% to about 45%; from about 10% to about 35%; from about 20% to about 35%; or from about 30% to about 35%.

In other various embodiments, the hydrophobic redox mediator of Formula 2A is a transition metal complex of osmium, ruthenium, iron, nickel, rhodium, rhenium, or cobalt with 1,10-phenanthroline (phen), 2,2'-bipyridine (bpy) or 2,2',2''-terpyridine (terpy), methylene green, methylene blue, poly(methylene green), poly(methylene blue), luminol, nitrofluorenone derivatives, azines, osmium phenanthrolinedione, catechol-pendant terpyridine, toluene blue, cresyl blue, nile blue, neutral red, phenazine derivatives, thionin, azure A, azure B, toluidine blue O, acetophenone, metallophthalocyanines, nile blue A, modified transition metal ligands, 1,10-phenanthroline-5,6-dione, 1,10-phenanthroline-5,6-diol, [Re(phen-dione)(CO)$_3$Cl], [Re(phen-dione)$_3$](PF$_6$)$_2$, poly(metallophthalocyanine), poly(thionine), quinones, diimines, diaminobenzenes, diaminopyridines, phenothiazine, phenoxazine, toluidine blue, brilliant cresyl blue, 3,4-dihydroxybenzaldehyde, poly(acrylic acid), poly(azure I), poly(nile blue A), polyaniline, polypyridine, polypyrole, polythiophene, poly(thieno[3,4-b]thiophene), poly(3-hexylthiophene), poly(3,4-ethylenedioxypyrrole), poly(isothianaphthene), poly(3,4-ethylenedioxythiophene), poly(difluoroacetylene), poly(4-dicyanomethylene-4H-cyclopenta[2,1-b;3,4-b']dithiophene), poly(3-(4-fluorophenyl)thiophene), poly(neutral red), or combinations thereof.

Preferably, the hydrophobic redox mediator is Ru(phen)$_3^{+2}$, Fe(phen)$_3^{+2}$, Os(phen)$_3^{+2}$, Co(phen)$_3^{+2}$, Cr(phen)$_3^{+2}$, Ru(bpy)$_3^{+2}$, Os(bpy)$_3^{+2}$, Fe(bpy)$_3^{+2}$, Co(bpy)$_3^{+2}$, Cr(bpy)$_3^{+2}$, Os(terpy)$_3^{+2}$, Ru(bpy)$_2$(4-methyl-4'-(6-hexyl)-2,2'-bipyridine)$^{+2}$, Co(bpy)$_2$(4-methyl-4'-(6-hexyl)-2,2'-bipyridine)$^{+2}$, Cr(bpy)$_2$(4-methyl-4'-(6-hexyl)-2,2'-bipyridine)$^{+2}$, Fe(bpy)$_2$(4-methyl-4'-(6-hexyl)-2,2'-bipyridine)$^{+2}$, Os(bpy)$_2$(4-methyl-4'-(6-hexyl)-2,2'-bipyridine)$^{+2}$, or combinations thereof. More preferably, the hydrophobic redox mediator is Ru(bpy)$_2$(4-methyl-4'-(6-hexyl)-2,2'-bipyridine)$^{+2}$, Co(bpy)$_2$(4-methyl-4'-(6-hexyl)-2,2'-bipyridine)$^{+2}$, Cr(bpy)$_2$(4-methyl-4'-(6-hexyl)-2,2'-bipyridine)$^{+2}$, Fe(bpy)$_2$(4-methyl-4'-(6-hexyl)-2,2'-bipyridine)$^{+2}$, Os(bpy)$_2$(4-methyl-4'-(6-hexyl)-2,2'-bipyridine)$^{+2}$, or combinations thereof. In various preferred embodiments, the hydrophobic redox mediator is Ru(bpy)$_2$(4-methyl-4'-(6-hexyl)-2,2'-bipyridine)$^{+2}$.

For the immobilization material having a hydrophobic redox mediator as the modifier, the hydrophobic redox mediator is typically covalently bonded to the chitosan or polysaccharide backbone. Typically, in the case of chitosan, the hydrophobic redox mediator is covalently bonded to one of the amine functionalities of the chitosan through a —N—C— bond. In the case of metal complex redox mediators, the metal complex is attached to the chitosan through an —N—C— bond from a chitosan amine group to an alkyl group attached to one or more of the ligands of the metal complex. A structure corresponding to Formula 2C is an example of a metal complex attached to a chitosan

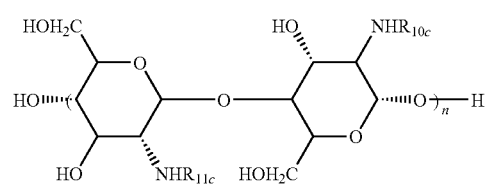

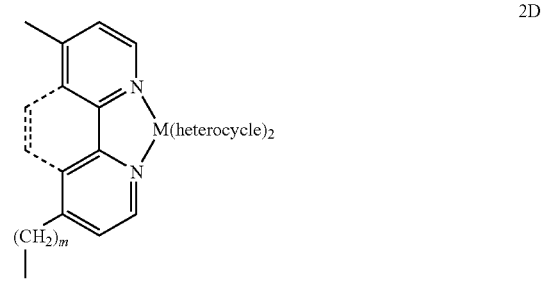

wherein n is an integer; $R_{10c}$ is independently hydrogen or a structure corresponding to Formula 2D; $R_{11c}$ is independently hydrogen or a structure corresponding to Formula 1D; m is an integer from 0 to 10; M is Ru, Os, Fe, Cr, or Co; and heterocycle is bipyridyl, substituted bipyridyl, phenanthroline, acetylacetone, and combinations thereof.

The hydrophobic group used to modify chitosan serves the dual function of (1) dictating the immobilization material's micelle size and (2) modifying the chitosan's chemical environment to maintain an acceptable micelle environment, both of which stabilize the enzyme. With regard to the first function of the hydrophobic group, hydrophobically modifying chitosan produces an immobilization material wherein the pore size is dependent on the size of the hydrophobic group. Accordingly, the size, shape, and extent of the modification of the chitosan with the hydrophobic group affects the size and shape of the micellar pore/pocket. This function of the hydrophobic group allows the micellar pore/pocket size to be made larger or smaller or a different shape to fit a specific enzyme by varying the size and branching of the hydrophobic group.

Regarding the second function of the hydrophobic cation, the properties of the hydrophobically modified chitosan membranes are altered by modifying chitosan with hydrophobic groups. This hydrophobic modification of chitosan affects the pore environment by increasing the number of available exchange sites to proton. In addition to affecting the pH of the material, the hydrophobic modification of chitosan provides a membrane that is a mechanical barrier, which further protects the immobilized enzymes.

Table 1 shows the number of available exchange sites to proton for the hydrophobically modified chitosan membrane.

TABLE 1

Number of available exchange sites to proton per gram of chitosan polymer

| Membrane | Exchange sites per gram ($\times 10^{-4}$ mol $SO_3$/g) |
| --- | --- |
| Chitosan | 10.5 ± 0.8 |
| Butyl Modified | 226 ± 21 |
| Hexyl Modified | 167 ± 45 |
| Octyl Modified | 529 ± 127 |
| Decyl Modified | 483 ± 110 |

Further, such polycationic polymers are capable of immobilizing enzymes and increasing the activity of enzymes immobilized therein as compared to the activity of the same enzyme in a buffer solution. In various embodiments, the polycationic polymers are hydrophobically modified polysaccharides, particularly, hydrophobically modified chitosan. For example, for the hydrophobic modifications noted, the enzyme activities for glucose oxidase were measured. The highest enzyme activity was observed for glucose oxidase in a hexyl modified chitosan suspended in t-amyl alcohol. These immobilization membranes showed a 2.53 fold increase in glucose oxidase enzyme activity over enzyme in buffer. Table 2 details the glucose oxidase activities for a variety of hydrophobically modified chitosans.

TABLE 2

Glucose oxidase enzyme activity for modified chitosans

| Membrane/Solvent | Enzyme Activity (Units/gm) |
| --- | --- |
| Buffer | 103.61 ± 3.15 |
| UNMODIFIED CHITOSAN | 214.86 ± 10.23 |
| HEXYL CHITOSAN | |
| Chloroform | 248.05 ± 12.62 |
| t-amyl alcohol | 263.05 ± 7.54 |
| 50% acetic acid | 118.98 ± 6.28 |
| DECYL CHITOSAN | |
| Chloroform | 237.05 ± 12.31 |
| t-amyl alcohol | 238.05 ± 10.02 |
| 50% acetic acid | 3.26 ± 2.82 |
| OCTYL CHITOSAN | |
| Chloroform | 232.93 ± 7.22 |
| t-amyl alcohol | 245.75 ± 9.77 |
| 50% acetic acid | 127.55 ± 11.98 |
| BUTYL CHITOSAN | |
| Chloroform | 219.15 ± 9.58 |
| t-amyl alcohol | 217.10 ± 6.55 |
| 50% acetic acid | 127.65 ± 3.02 |

To prepare the hydrophobically modified chitosans of the invention having an alkyl group as a modifier, a chitosan gel was suspended in acetic acid followed by addition of an alcohol solvent. To this chitosan gel was added an aldehyde (e.g., butanal, hexanal, octanal, or decanal), followed by addition of sodium cyanoborohydride. The resulting product was separated by vacuum filtration and washed with an alcohol solvent. The modified chitosan was then dried in a vacuum oven at 40° C. and resulted in a flaky white solid.

To prepare a hydrophobically modified chitosan of the invention having a redox mediator as a modifier, a redox mediator ligand was derivatized by contacting 4,4'-dimethyl-2,2'-bipyridine with lithium diisopropylamine followed by addition of a dihaloalkane to produce 4-methyl-4'-(6-haloalkyl)-2,2'-bipyridine. This ligand was then contacted with Ru(bipyridine)$_2$Cl$_2$ hydrate in the presence of an inorganic base and refluxed in a water-alcohol mixture until the Ru(bipyridine)$_2$Cl$_2$ was depleted. The product was then precipitated with ammonium hexafluorophosphate, or optionally a sodium or potassium perchlorate salt, followed by recrystallization. The derivatized redox mediator (Ru(bipyridine)$_2$(4-methyl-4'-(6-bromohexyl)-2,2'-bipyridine)$^{+2}$) was then contacted with deacetylated chitosan and heated. The redox mediator modified chitosan was then precipitated and recrystallized.

The hydrophobically modified chitosan membranes have advantageous insolubility in ethanol. For example, the chitosan enzyme immobilization materials described above generally are functional to immobilize and stabilize the enzymes in solutions having up to greater than about 99 wt. % or 99 volume % ethanol. In various embodiments, the chitosan immobilization material is functional in solutions having 15, 20, 25, 30, 35, 40, 45, 50, 55, 60, 65, 70, 75, 80, 85, 90, 95 or more wt. % or volume % ethanol. In some instances the chitosan immobilization material is functional in solutions having from about 15 to about 95 wt. % or vol. % ethanol, from about 25 to about 95 wt. % or vol. % ethanol, from about 35 to about 95 wt. % or vol. % ethanol, from about 45 to about 95 wt. % or vol. % ethanol, from about 55 to about 95 wt. % or vol. % ethanol, from about 65 to about 95 wt. % or vol. % ethanol, from about 70 to about 95 wt. % or vol. % ethanol, from about 75 to about 95 wt. % or vol. % ethanol, from about 80 to about 95 wt. % or vol. % ethanol, from about 85 to about 95 wt. % or vol. % ethanol, or from about 90 to about 95 wt. % or vol. % ethanol.

In other embodiments, the micellar or inverted micellar immobilization materials are polyanionic polymers, such as hydrophobically modified polysaccharides, particularly, hydrophobically modified alginate. Alginates are linear unbranched polymers containing β-(1-4)-linked D-mannuronic acid and α-(1-4)-linked L-guluronic acid residues. In the unprotonated form, β-(1-4)-linked D-mannuronic acid corresponds to the structure of Formula 3A

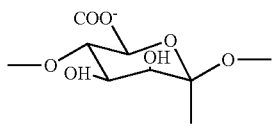

3A and in the unprotonated form, α-(1-4)-linked L-guluronic acid corresponds to the structure of Formula 3B(Note structures 3a and 3B could be made better by showing bonding to the C6 carboxylate to the carbon and, in 3A, bonding of C3 to the oxygen in the hydroxyl group.)

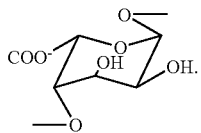

3B

Alginate is a heterogeneous polymer consisting of polymer blocks of mannuronic acid residues and polymer blocks of guluronic acid residues.

Alginate polymers can be modified in various ways. One type is alginate modified with a hydrophobic cation that is larger than the ammonium ($NH_4^+$) ion. The hydrophobic cation serves the dual function of (1) dictating the polymer's pore size and (2) acting as a chemical buffer to help maintain the micelle's pH level, both of which stabilize the enzyme. With regard to the first function of the hydrophobic cation, modifying alginate with a hydrophobic cation produces an immobilization material wherein the micelle size is dependent on the size of the hydrophobic cation. Accordingly, the size, shape, and extent of the modification of the alginate with the hydrophobic cation affects the size and shape of the micellar pore/pocket. This function of the hydrophobic cation allows the micelle size to be made larger or smaller or a different shape to fit a specific enzyme by varying the size and branching of the hydrophobic cation.

Regarding the second function of the hydrophobic cation, the properties of the alginate polymer are altered by exchanging the hydrophobic cation for protons as the counterion to the —$CO_2^-$ groups on the alginate. This change in counterion provides a buffering effect on the pH because the hydrophobic cation has a much greater affinity for the —$CO_2^-$ sites than protons do. This buffering effect of the alginate membrane causes the pH of the micellar pore/pocket to remain substantially unchanged with changing solution pH; stated another way, the pH of the pore resists changes in the solution's pH. In addition, the alginate membrane provides a mechanical barrier, which further protects the immobilized enzymes.

In order to prepare a modified alginate membrane, the first step is to cast a suspension of alginate polymer with a solution of the hydrophobic cation to form a membrane. The excess hydrophobic cations and their salts are then extracted from the membrane, and the membrane is re-cast. Upon re-casting, the membrane contains the hydrophobic cations in association with —$CO_2^-$ sites of the alginate membrane. Removal of the salts of the hydrophobic cation from the membrane results in a more stable and reproducible membrane; if they are not removed, the excess salts can become trapped in the pore or cause voids in the membrane.

In one embodiment, a modified alginate membrane is prepared by casting a suspension of alginate polymer with a solution of a salt of a hydrophobic cation such as quaternary ammonium bromide. Excess quaternary ammonium bromide or hydrogen bromide is removed from the membrane before it is re-cast to form the salt-extracted membrane. Salt extraction of membranes retains the presence of the quaternary ammonium cations at the carboxylic acid exchange sites, but eliminates complications from excess salt that may be trapped in the pore or may cause voids in the equilibrated membrane. Exemplary hydrophobic cations are ammonium-based cations, quaternary ammonium cations, alkyltrimethylammonium cations, alkyltriethylammonium cations, organic cations, phosphonium cations, triphenylphosphonium, pyridinium cations, imidazolium cations, hexadecylpyridinium, ethidium, viologens, methyl viologen, benzyl viologen, bis (triphenylphosphine)iminium, metal complexes, bipyridyl metal complexes, phenanthroline-based metal complexes, $[Ru(bipyridine)_3]^{2+}$ and $[Fe(phenanthroline)_3]^{3+}$.

In one preferred embodiment, the hydrophobic cations are ammonium-based cations. In particular, the hydrophobic cations are quaternary ammonium cations. In another embodiment, the quaternary ammonium cations are represented by Formula 4:

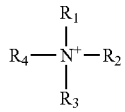

4 wherein $R_1$, $R_2$, $R_3$, and $R_4$ are independently hydrogen, hydrocarbyl, substituted hydrocarbyl, or heterocyclo wherein at least one of $R_1$, $R_2$, $R_3$, and $R_4$ is other than hydrogen. In a further embodiment, preferably, $R_1$, $R_2$, $R_3$, and $R_4$ are independently hydrogen, methyl, ethyl, propyl, butyl, pentyl, hexyl, heptyl, octyl, nonyl, decyl, undecyl, dodecyl, tridecyl or tetradecyl wherein at least one of $R_1$, $R_2$, $R_3$, and $R_4$ is other than hydrogen. In still another embodiment, $R_1$, $R_2$, $R_3$, and $R_4$ are the same and are methyl, ethyl, propyl, butyl, pentyl or hexyl. In yet another embodiment, preferably, $R_1$, $R_2$, $R_3$, and $R_4$ are butyl. In yet another embodiment, preferably, $R_1$, $R_2$, $R_3$, and $R_4$ are ethyl. Preferably, the quaternary ammonium cation is tetraethylammonium, tetrapropylammonium (T3A), tetrapentylammonium (T5A), tetrahexylammonium (T6A), tetraheptylammonium (T7A), trimethylicosylammonium (TMICA), trimethyloctyldecylammonium (TMODA), trimethylhexyldecylammonium (TMHDA), trimethyltetradecylammonium (TMTDA), trimethyloctylammonium (TMOA), trimethyldodecylammonium (TMDDA), trimethyldecylammonium (TMDA), trimethylhexylammonium (TMHA), tetrabutylammonium (TBA), triethylhexylammonium (TEHA), and combinations thereof.

The micelle characteristics were studied and the micellar pore/pocket structure of this membrane is ideal for enzyme immobilization, because the micellar pores/pockets are hydrophobic, micellar in structure, buffered to external pH change, and have high pore interconnectivity.

In another experiment, ultralow molecular weight alginate and dodecylamine were placed in 25% ethanol and refluxed to produce a dodecyl-modified alginate by amidation of the carboxylic acid groups. Various alkyl amines can be substituted for the dodecylamine to produce alkyl-modified alginate having a $C_4$-$C_{16}$ alkyl group attached to varying numbers of the reactive carboxylic acid groups of the alginate structure. In various embodiments, at least about 1, 2, 4, 6, 8, 10, 12, 14, 16, 18, 20, 22, 24, 26, 28, 30, 32, 34, 36, 38, 40, 42, 44, 46, 48%, or more of the carboxylic acid groups react with the alkylamine. In some instances, from about 2 to about 50%, from about 10 to about 50%, from about 20 to about 50%, from about 30 to about 50%, from about 40 to about 50% of the carboxylic acid groups react with the alkylamine.

The hydrophobically modified alginate membranes have advantageous insolubility in ethanol. For example, the alginate enzyme immobilization materials described above generally are functional to immobilize and stabilize the enzymes in solutions having at least about 25 wt. % or 25 volume % ethanol. In various embodiments, the alginate immobilization material is functional in solutions having 25, 30, 35, 40, 45, 50, 55, 60, 65, 70, 75, 80, 85, 90 or more wt. % or volume % ethanol. In some instances, the alginate immobilization material is functional in solutions having from about 25 to about 95 wt. % or vol. % ethanol, from about 35 to about 95 wt. % or vol. % ethanol, from about 45 to about 95 wt. % or vol. % ethanol, from about 55 to about 95 wt. % or vol. % ethanol, from about 65 to about 95 wt. % or vol. % ethanol, from about 70 to about 95 wt. % or vol. % ethanol, from about 75 to about 95 wt. % or vol. % ethanol, from about 80 to about 95 wt. % or vol. % ethanol, from about 85

In order to evaluate the most advantageous immobilization material for a particular enzyme, the selected enzyme can be immobilized in various immobilization materials, deposited on an electron conductor, and treated with a solution containing an electron mediator (e.g., $NAD^+$) and/or a substrate for the particular enzyme in a buffer solution. A fluorescence micrograph is obtained and shows fluorescence when the enzyme immobilized in the particular immobilization material is still a catalytically active enzyme after immobilization. Enzyme activity could also be determined by any standard spectroscopic assay. Further, enzyme activity can be determined using a bioreactor for that enzyme, in particular, the activity of carbonic anhydrase can be measured by using the bioreactor described in example 1 or a carbonic anhydrase assay as published by Sigma (revision date Jul. 22, 1996). The carbonic anhydrase assay measures the rate of enzymatic $CO_2$ hydration by determining the net rate difference between a non-enzymatic blank and an enzyme-containing sample in the time required to decrease the pH of a buffered reaction mixture from 8.3 to 6.3.

The assay techniques described above are one way to determine whether a particular immobilization material will immobilize and stabilize an enzyme while retaining the enzyme's catalytic activity. For example, for starch-consuming amylase, the enzyme immobilization material that provided the greatest relative activity is provided by immobilization of the enzyme in butyl chitosan suspended in t-amyl alcohol. For maltose-consuming amylase, the greatest relative activity is provided by immobilization of the enzyme in medium molecular weight decyl modified chitosan.

One aspect of the present invention is directed to an enzyme immobilized by entrapment in a polymeric immobilization material, the immobilization material being permeable to a compound smaller than the enzyme and having the structure of either Formulae 5, 6, 7, or 8:

Formula 5

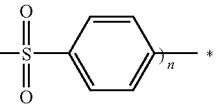

Formula 6

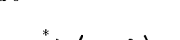

Formula 7

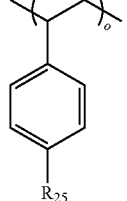

Formula 8

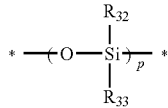

wherein $R_{21}$, $R_{22}$, $R_{23}$ and $R_{24}$ are independently hydrogen, alkyl, or substituted alkyl, provided that the average number of alkyl or substituted alkyl groups per repeat unit is at least 0.1 $R_{25}$ is hydrogen or substituted alkyl, provided that the average number of substituted alkyl groups per repeat unit is at least 0.1; $R_{32}$ and $R_{33}$ are independently hydrogen, alkyl, aryl, or substituted alkyl, provided that the average number of hydrogen atoms per repeat unit is at least 0.1 and m, n, o, and p are independently integers of from about 10 to about 5000. In many of these embodiments, the enzyme immobilization material comprises a micellar or inverted micellar polymer.

Modified Polysulfone

In some of the various embodiments, the immobilization material has a structure of Formula 5

Formula 5

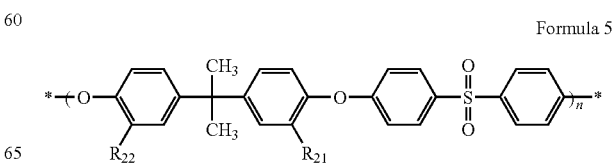

wherein $R_{21}$, $R_{22}$, and n are defined above. In various embodiments, $R_{21}$ and $R_{22}$ are independently hydrogen, alkyl, or substituted alkyl. In various embodiments, $R_{21}$ and $R_{22}$ are independently hydrogen or —$(CH_2)_q N^+ R_{26} R_{27} R_{28}$, wherein $R_{26}$, $R_{27}$, and $R_{28}$ are independently alkyl and q is an integer of 1, 2, or 3; particularly, $R_{26}$, $R_{27}$, and $R_{28}$ are independently methyl, ethyl, propyl, butyl, pentyl, or hexyl; more particularly, $R_{26}$, $R_{27}$, and $R_{28}$ are methyl.

Alternatively, $R_{21}$ and $R_{22}$ are independently hydrogen or —$(CH_2)_q N^+ R_{26} R_{27} R_{28}$, wherein $R_{26}$ and $R_{27}$ are independently methyl, ethyl, or propyl, $R_{28}$ is alkylamino, and q is an integer of 1, 2, or 3. When $R_{28}$ is alkylamino, preferred alkylamino groups are tertiary alkylamino groups. For example, the alkylamino group can be —$CH_2 N^+ R_{29} R_{30} R_{31}$, —$CH_2 CH_2 N^+ R_{29} R_{30} R_{31}$ or —$CH_2 CH_2 CH_2 N^+ R_{29} R_{30} R_{31}$ wherein $R_{29}$, $R_{30}$, and $R_{31}$ are independently hydrogen or alkyl. In various preferred embodiments, $R_{29}$, $R_{30}$, and $R_{31}$ are independently methyl, ethyl, propyl, butyl, pentyl, or hexyl; more particularly, $R_{29}$, $R_{30}$, and $R_{31}$ are methyl or ethyl.

Preferably, $R_{21}$, $R_{22}$, or $R_{21}$ and $R_{22}$ are alkyl or substituted alkyl wherein the average number of alkyl or substituted alkyl groups per repeat unit is from about 0.1 to about 1.4, from about 0.2 to about 1.4, from about 0.3 to about 1.4, from about 0.3 to about 1.2, from about 0.3 to about 1, from about 0.3 to about 0.8, from about 0.4 to about 1.4, from about 0.4 to about 1.2, from about 0.4 to about 1, from about 0.4 to about 0.8, from about 0.5 to about 1.4, from about 0.5 to about 1.2, from about 0.5 to about 1, from about 0.5 to about 0.8.

In other preferred embodiments, $R_{21}$ and $R_{22}$ are independently hydrogen or —$(CH_2)_q$-polyether wherein q is an integer of 1, 2, or 3. In preferred embodiments, q is 1. In some of the preferred embodiments, $R_{21}$ and $R_{22}$ are independently hydrogen, —$CH_2$—O—$(CH_2(CH_3)$—$CH_2$—O$)_z$—$R_t$, —$CH_2$—O—$(CH_2$—$CH_2$—O$)_z$—$R_t$, or a combination thereof wherein z is an integer from 3 to 180, and the polyethylene oxide or polypropylene oxide (e.g., —O—$(CH_2$—$CH_2$—O$)_z$—$R_t$ or —$CH_2$—O—$(CH_2(CH_3)$—$CH_2$—O$)_z$—$R_t$ wherein $R_t$ is hydrogen, alkyl, substituted alkyl, aryl, or substituted aryl) has a molecular weight from about 150 Daltons (Da) to about 8000 Daltons (Da). In particular embodiments, the polyethylene oxide has a molecular weight from about 500 Da to about 600 Da; particularly about 550 Da.

Modified polysulfone is a desirable immobilization material because it has good chemical and thermal stability. Additionally, modified polysulfone has advantageous solubility characteristics in polar organic solvents such as N-methylpyrrolidone (NMP) and dioxane. This solubility enables the modified polysulfone beads to be prepared by precipitation in water or lower aliphatic alcohols. Unmodified polysulfone can immobilize and retain an enzyme (e.g., carbonic anhydrase) in the beads. But, the activity of the carbonic anhydrase is reduced and it is hypothesized that the low porosity and thus, the low permeability of unmodified polysulfone beads at the polymer-solvent interface prevents the substrate and product from diffusing to and from the active site of the enzyme. In order to improve the porosity, the polysulfone can be modified to increase the porosity and transport of the substrate and product through the material.

For example, the polysulfone can be modified by adding amine groups to the benzene groups of the polysulfone. By modifying the polysulfone with quaternary amine groups, the hydrophilicity of the polysulfone is affected and in turn the porosity and the transport of carbonate/bicarbonate ions increases. Also, the positively charged amine groups can stabilize carbonic anhydrase through electrostatic interactions. This modification of adding a hydrophobic group to a hydrophilic polymer may also form micellar aggregate/pore structures in the polymer. To add amine groups to the polysulfone, the benzene rings of the backbone are chloromethylated followed by the amination of the chloromethyl groups. This process is generally described in Jihua, H.; Wentong, W.; Puchen, Y.; Qingshuang, Z. Desalination 1991, 83, 361 and Park, J.-S.; Park, G.-G.; Park, S.-H.; Yoon, Y.-G.; Kim, C. S.; Lee, W. Y. Macromol. Symp. 2007, 249-250, 174. The general reaction scheme for this transformation is shown in Scheme 1. The average number of chloromethyl groups added per repeat unit can be controlled by manipulating the reactant ratios during the first step as described in Hibbs, M. R.; Hickner, M. A.; Alam, T. M.; McIntyre, S. K.; Fujimoto, C. H.; Cornelius, C. J. Chem. Mater. 2008, 20, 2566.

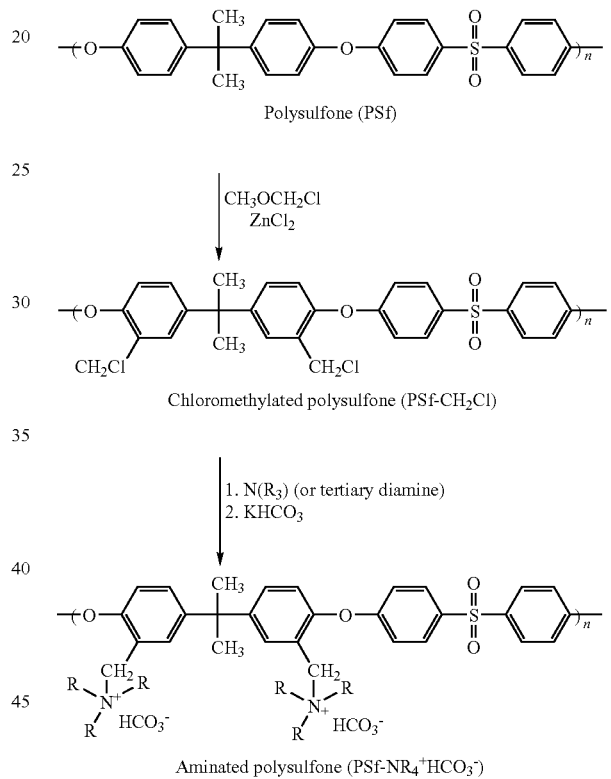

Scheme 1. Reaction scheme for the formation of aminated polysulfone

Additionally, the choice of tertiary amine added to the chloromethylated polysulfone (PSf-$CH_2Cl$) can affect the polysulfone properties. For instance, trimethyl amine can be used to aminate PSf-$CH_2Cl$, resulting in a quaternary benzyl trimethyl ammonium cation. This benzyl trimethyl ammonium cation has been shown to be more stable with prolonged exposure to elevated temperatures and/or strongly basic solutions. (See Sata, T.; Tsujimoto, M.; Yamaguchi, T.; Matsusaki, K. J. Membrane Sci. 1996, 112, 161.) Tertiary diamines can also be used in this amination step, providing a way of crosslinking polysulfone to improve its mechanical and thermal stability. The addition of diamines to chloromethylated polysulfone solutions crosslinks polysulfone and solidifies the mixture. The solvent can then be exchanged with water or methanol to yield a more porous aminated polysulfone. The initial polymer concentration of the solution can be adjusted to manipulate the porosity in the resulting polysulfone. The exchange of the chloride anions with bicarbonate anions after amination could improve the performance of the immobilized carbonic anhydrase by removing chloride ions that inhibit enzyme activity. Additionally, the incorporation of bicarbonate ions into polysulfone could provide a buffering capacity to protect the enzyme from pH changes.

Further, once the polysulfone is chloromethylated, other modified polysulfone polymers can be prepared. For example, the chloromethyl groups can react with a hydroxyl end group of poly(ethylene oxide) (PEO) to create polysulfone polymers with grafted PEO side chains. (See Park, J. Y.; Acar, M. H.; Akthakul, A.; Kuhlman, W.; Mayes, A. M. *Biomater.* 2006, 27, 856.) The general reaction scheme is shown in Scheme 2. As described above, the chloromethylation of polysulfone can be manipulated to provide control over the grafting density of the PEO side chains. Additionally, the molecular weight of the PEO side chains can be altered to influence the overall weight loading of PEO in PEO-modified polysulfone; the loading affects the overall mechanical properties of the polymer.

Scheme 2. Reaction scheme for the formation of PSf-g-PEO

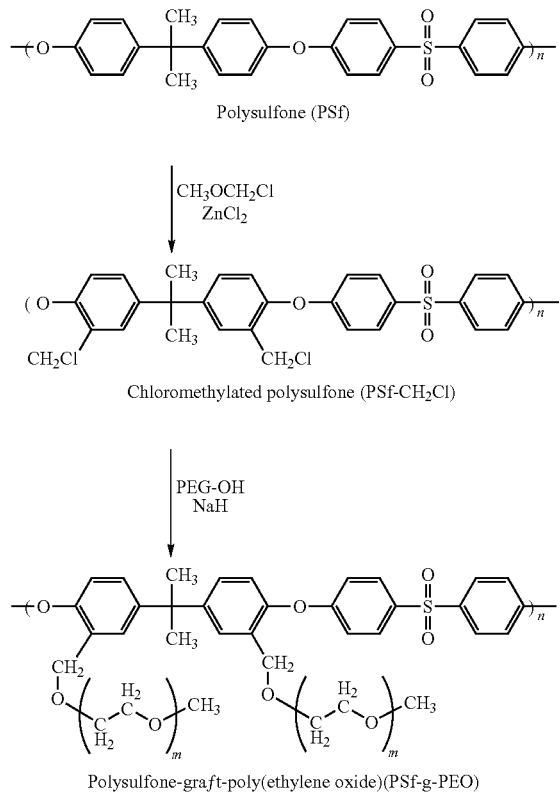

The incorporation of PEO into polysulfone will improve the hydrophilicity of these beads and the transport of carbonate/bicarbonate ions. Additionally, when polyethylene glycol-modified carbonic anhydrase is the enzyme, the PEO-modified polysulfone can provide a hydrophilic PEO layer around the carbonic anhydrase and further prevent the enzyme from leaching. The PEO encapsulation of carbonic anhydrase can also protect the enzyme from effects of drying that may be important for retaining its activity upon immobilization.

Additionally, particular processing conditions can also improve the porosity and the ion transport of the polymers. For instance, it is possible to foam polysulfone through the use of supercritical carbon dioxide to introduce microporous structure into polysulfone polymers. (See Krause, B.; Mettinkhof, R.; van der Vegt, N. F. A.; Wessling, M. *Macromolecules* 2001, 34, 874.) A similar approach could be used to enable the foaming of modified polysulfone beads. Microporosity can also be introduced into polysulfone by using a freeze-drying process similar to the process used to create microporous chitosan. (See Cooney, M. J.; Lau, C.; Windmeisser, M.; Liaw, B. Y.; Klotzbach, T.; Minteer, S. D. *J. Mater. Chem.* 2008, 18, 667.) Since polysulfone is not soluble in a water/acetic acid mixture, a suitable solvent for polysulfone that is capable of appreciable sublimation in its solid state under vacuum is required. Menthol is a promising candidate due to its low melting temperature (35° C.) and comparable solubility parameter to dioxane, which suggests that polysulfone could dissolve at high concentrations in menthol at slightly elevated temperatures.

Modified Polycarbonate

In certain embodiments, the immobilization material has a structure of Formula 6

Formula 6

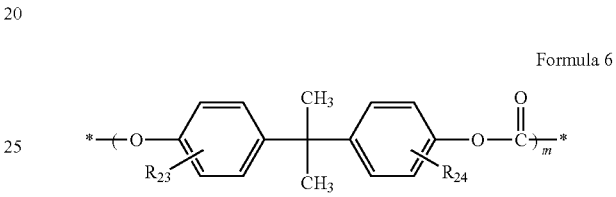

wherein $R_{23}$, $R_{24}$, and m are defined above. In various embodiments, $R_{23}$ and $R_{24}$ are independently hydrogen, alkyl, or substituted alkyl. In various embodiments, $R_{23}$ and $R_{24}$ are independently hydrogen or $-(CH_2)_q N^+ R_{26} R_{27} R_{28}$, wherein $R_{26}$, $R_{27}$, and $R_{28}$ are independently alkyl and q is an integer of 1, 2, or 3; particularly, $R_{26}$, $R_{27}$, and $R_{28}$ are independently methyl, ethyl, propyl, butyl, pentyl, or hexyl; more particularly, $R_{26}$, $R_{27}$, and $R_{28}$ are methyl.

Alternatively, $R_{23}$ and $R_{24}$ are independently hydrogen or $-(CH_2)_p N^+ R_{26} R_{27} R_{28}$ wherein $R_{26}$ and $R_{27}$ are independently methyl, ethyl, or propyl, $R_8$ is alkylamino, and p is an integer of 1, 2, or 3. When $R_{28}$ is alkylamino, preferred alkylamino groups are tertiary alkylamino groups. For example, the alkylamino group can be $-CH_2 N^+ R_{29} R_{30} R_{31}$, $-CH_2CH_2 N^+ R_{29} R_{30} R_{31}$ or $-CH_2CH_2CH_2 N^+ R_{29} R_{30} R_{31}$ wherein $R_{29}$, $R_{30}$, and $R_{31}$ are independently hydrogen or alkyl. In various preferred embodiments, $R_{29}$, $R_{30}$, and $R_{31}$ are independently methyl, ethyl, propyl, butyl, pentyl, or hexyl; more particularly, $R_{29}$, $R_{30}$, and $R_{31}$ are methyl or ethyl.

In other preferred embodiments, $R_{23}$ and $R_{24}$ are independently hydrogen or $-(CH_2)_q$-polyether wherein q is an integer of 1, 2, or 3. In some of the preferred embodiments, $R_{23}$ and $R_{24}$ are independently hydrogen, $-CH_2-O-(CH_2(CH_3)-CH_2-O)_z-R_t$, $-CH_2-O-(CH_2-CH_2-O)_z-R_t$, or a combination thereof wherein z is an integer from 3 to 180, and the polyethylene oxide or polypropylene oxide (e.g., $-O-(CH_2-CH_2-O)_z-R_t$ or $-CH_2-O-(CH_2(CH_3)-CH_2-O)_z-R_t$ wherein $R_t$ is hydrogen, alkyl, substituted alkyl, aryl, or substituted aryl) has a molecular weight from about 150 Daltons (Da) to about 8000 Daltons (Da).

Preferably, $R_{23}$, $R_{24}$, or $R_{23}$ and $R_{24}$ are alkyl or substituted alkyl wherein the average number of alkyl or substituted alkyl groups per repeat unit is from about 0.1 to about 1.4, from about 0.2 to about 1.4, from about 0.3 to about 1.4, from about 0.3 to about 1.2, from about 0.3 to about 1, from about 0.3 to about 0.8, from about 0.4 to about 1.4, from about 0.4 to about 1.2, from about 0.4 to about 1, from about 0.4 to about 0.8, from about 0.5 to about 1.4, from about 0.5 to about 1.2, from about 0.5 to about 1, from about 0.5 to about 0.8.

Polycarbonate has a structure similar to polysulfone. It also contains benzene rings in its backbone, so it can be functionalized by adding chloromethyl groups in the same manner as described above for polysulfone. These chloromethyl groups can then be aminated or have PEO grafted following the same procedure utilized for polysulfone. Schemes 3 and 4 show the general reaction schemes for both. Similar to polysulfone, polycarbonate can be foamed using supercritical carbon dioxide.

Scheme 3. Reaction scheme for the formation of aminated polycarbonate

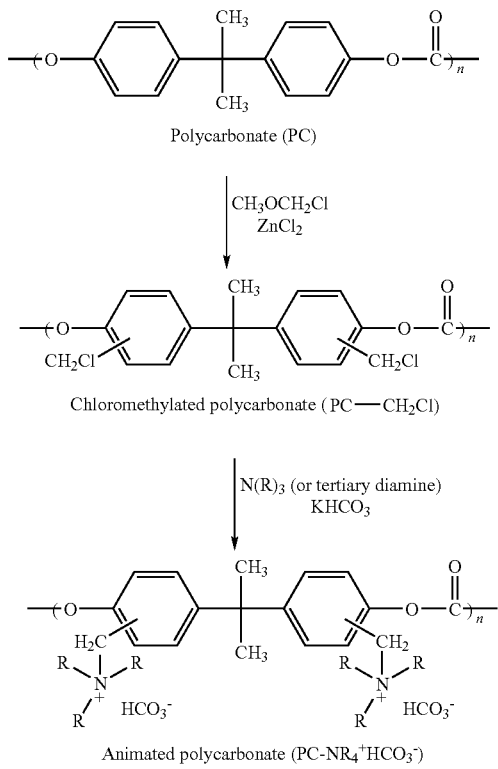

Scheme 4. Reaction scheme for the formation of PC-g-PEO

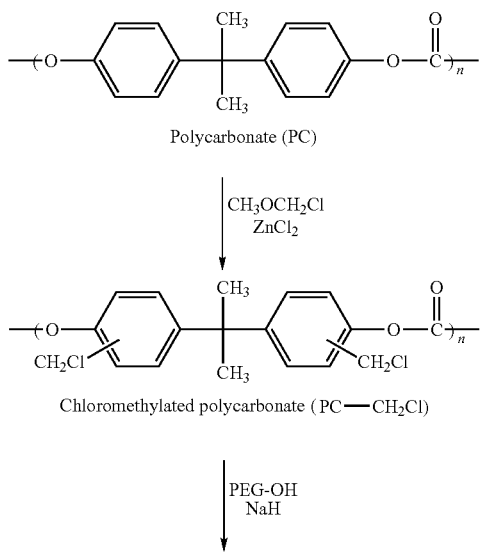

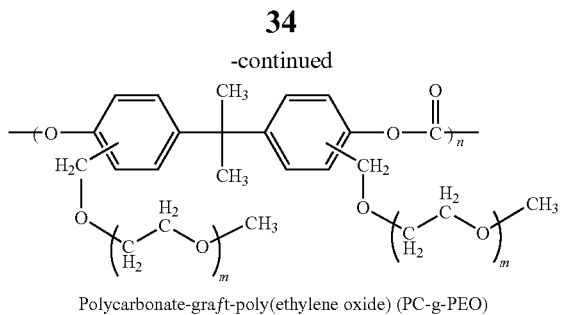

Polycarbonate-gra*f*t-poly(ethylene oxide) (PC-g-PEO)

Modified Poly(vinylbenzyl chloride)

In other embodiments, the immobilization material has a structure of Formula 7

Formula 7 wherein $R_{25}$ and o are defined above. In various embodiments, $R_{25}$ is hydrogen, alkyl, or substituted alkyl. In various embodiments, $R_{25}$ is hydrogen or $—(CH_2)_qN^+R_{26}R_{27}R_{28}$, wherein $R_{26}$, $R_{27}$, and $R_{28}$ are independently alkyl and q is an integer of 1, 2, or 3; particularly, $R_{26}$, $R_{27}$, and $R_{28}$ are independently methyl, ethyl, propyl, butyl, pentyl, or hexyl; more particularly, $R_{26}$, $R_{27}$, and $R_{28}$ are methyl.

Alternatively, $R_{25}$ is hydrogen or $—(CH_2)_pN^+R_{26}R_{27}R_{28}$ wherein $R_{26}$ and $R_{27}$ are independently methyl, ethyl, or propyl, $R_{28}$ is alkylamino, and p is an integer of 1, 2, or 3. When $R_{28}$ is alkylamino, preferred alkylamino groups are tertiary alkylamino groups. For example, preferred alkylamino groups can be $—CH_2N^+R_{29}R_{30}R_{31}$, $—CH_2CH_2N^+R_{29}R_{30}R_{31}$ or $—C_6H_4N^+R_{29}R_{30}R_{31}$ wherein $R_{29}$, $R_{30}$, and $R_{31}$ are independently hydrogen or alkyl. In various preferred embodiments, $R_{29}$, $R_{30}$, and $R_{31}$ are independently methyl, ethyl, propyl, butyl, pentyl, or hexyl; more particularly, $R_{29}$, $R_{30}$, and $R_{31}$ are methyl or ethyl.

Preferably, $R_{25}$ is substituted alkyl wherein the average number of substituted alkyl groups per repeat group is at least 0.1, 0.2, 0.3, 0.4, 0.5, 0.6, 0.7, or more.

Poly(vinylbenzyl chloride) (PVBC) is a commercially-available polymer with a chloromethyl group contained in the polymer, so it can be aminated similarly to the synthetic procedure described above for chloromethylated polysulfone or polycarbonate. PVBC, however, lacks the mechanical strength of polysulfone and polycarbonate and is somewhat brittle and has a lower glass transition temperature. However, it is believed that the mechanical and thermal stability of this polymer can be improved by crosslinking PVBC by amination with tertiary diamines. (See Varcoe, J. R.; Slade, R. C. T.; Lee, E. L. H. *Chem. Commun.* 2006, 1428.) This process incorporates positive charges in the PVBC and these charges can also stabilize the immobilized enzyme through electrostatic interactions. Scheme 5 shows the general scheme for this reaction.

Scheme 5. Reaction scheme for the formation of crosslinked PVBC

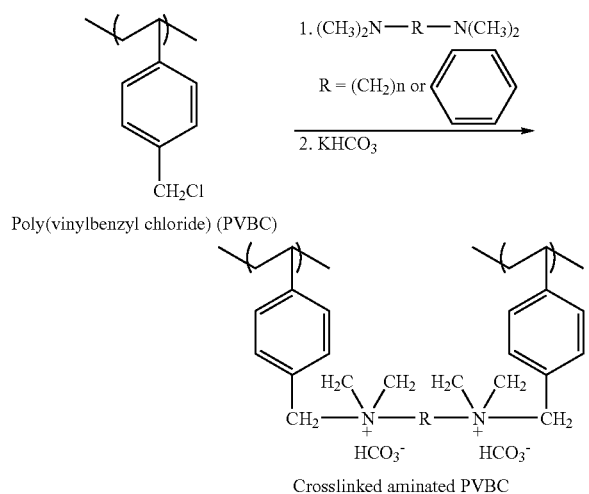

Poly(vinylbenzyl chloride) (PVBC)

Crosslinked aminated PVBC

Upon addition of a diamine to a 40 wt. % solution of PVBC in NMP, both a methylene (—CH$_2$—) and a phenylene (—C$_6$H$_4$—) spacer in the diamine produces crosslinked solid films. Diamines having the following structures were selected because they provide long-term stability to these quaternary amines. The use of tetramethyl methanediamine (TMMDA) solidifies this solution quickly (e.g., less than 10 minutes), indicating that the reaction of TMMDA with PVBC is fast. Once solidified, PVBC crosslinked with TMMDA does not swell upon addition of methanol or water. In contrast, the reaction of tetramethyl phenylenediamine (TMPDA) is slower and takes several hours to solidify. Once solidified, PVBC crosslinked with TMPDA swells significantly (but maintains its original shape) upon exposure to either methanol or water. PVBC crosslinked with TMPDA forms a hydrophilic, high-swelling material, which could significantly improve the transport of carbonate/bicarbonate ions through the polymer, as compared to polysulfone and polycarbonate that are rigid glassy polymers. Similar to the polysulfone and polycarbonate, the amount of derivatization of the modified PVBC can be altered by adjusting the polymer concentration of the solution during the chloromethylation reaction.

Modified Polysiloxanes

In various embodiments, the immobilization material has a structure of Formula 8

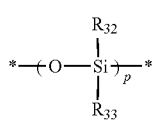

Formula 8 wherein $R_{32}$ and $R_{33}$ are independently hydrogen, alkyl, aryl, or substituted alkyl, provided that the average number of hydrogen atoms per repeat unit is at least 0.1.

In various embodiments, $R_{32}$ and $R_{33}$ are independently hydrogen, alkyl, aryl, -(substituted alkylene)-acid or a salt thereof, -(substituted alkylene)-base or a salt thereof, —(CH$_2$)$_q$O—(CH$_2$—CH$_2$—O)$_z$—R$_t$, —CH$_2$—O—(CH$_2$(CH$_3$)—CH$_2$—O)$_z$—R$_t$, or a combination thereof, wherein q is an integer of 2, 3, or 4 and R$_t$ is. The acid group can be a carboxylic, a phosphonic, a phosphoric, a sulfonic, a sulfuric, a sulfamate, a salt thereof, or a combination thereof. The base can be an amine base, particularly, a tertiary amine, a quaternary amine, a nitrogen heterocycle, a salt thereof, or a combination thereof. In particular embodiments, $R_{32}$ and $R_{33}$ are independently hydrogen, alkyl, aryl, —(CH$_2$)$_3$—O—((CH$_2$)$_2$—O—)$_z$CH$_3$, —(CH$_2$)$_2$—C(O)—O—(CH$_2$)$_2$-imidazolium, —(CH$_2$)$_3$—O—CH$_2$—CH(OH)—N(CH$_3$)—(CH$_2$)$_2$—SO$_3$Na.

The structure of Formula 8 is prepared starting with a hydrosiloxane, which is a polysiloxane that contains silicon hydride bonds. Examples include poly(methyl hydrosiloxane) (PMHS) homopolymer, poly(phenyl dimethylhydrosiloxy)siloxane (PPDMHS) homopolymer, and copolymers of PMHS or PPDMHS with other polysiloxanes such as poly(dimethylsiloxane) (PDMS) or poly(phenylmethylsiloxane) (PPMS). Specifically, polyalkyl hydrosiloxane (e.g., poly(methyl hydrosiloxane), poly(ethyl hydrosiloxane), poly(propyl hydrosiloxane), polyaryl hydrosiloxane (e.g., poly(phenyl hydrosiloxane), poly(tolyl hydrosiloxane)), poly(phenyl dimethylhydrosiloxy)siloxane, poly(dimethyl siloxane co-methyl hydrosiloxane), poly(methyl hydrosiloxane co-phenyl methyl siloxane), poly(methyl hydrosiloxane co-alkyl methyl siloxane), poly(methyl hydrosiloxane co-diphenyl siloxane), poly(methyl hydrosiloxane co-phenyl methyl siloxane). These polysiloxanes have a desirable CO$_2$ solubility. Without being bound by theory, it is believed that the elasticity of polysiloxanes increases CO$_2$ solubility. Using published procedures, these hydride-functional polysiloxanes can be grafted with polyether and/or ionic groups by coupling them with allyl-containing compounds using a platinum catalyst (hydrosilation reaction). The general reaction schemes are shown in Schemes 6-8.

Scheme 6. Synthesis of polyethylene glycol modified poly(methyl hydrosiloxane).

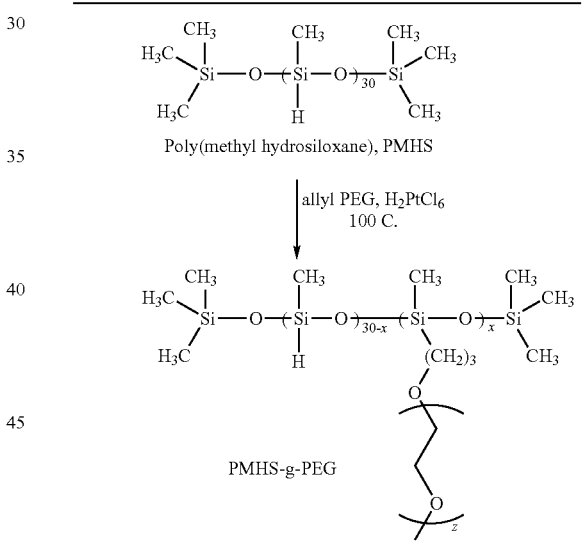

Poly(methyl hydrosiloxane), PMHS allyl PEG, H$_2$PtCl$_6$
100 C.

PMHS-g-PEG

Scheme 7. Synthesis of cation-modiefied poly(methyl hydrosiloxane).

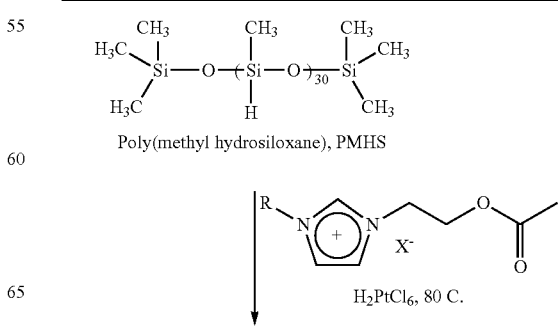

Poly(methyl hydrosiloxane), PMHS

H$_2$PtCl$_6$, 80 C.

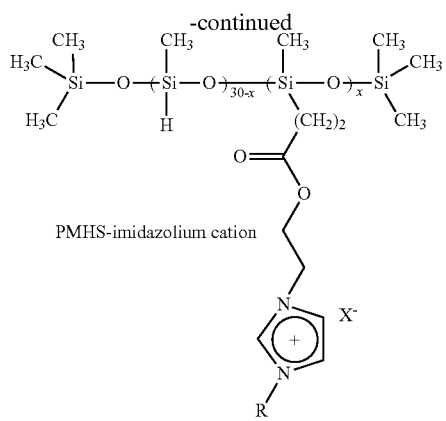

PMHS-imidazolium cation

Scheme 8. Synthesis of anion-modified poly(methyl hydrosiloxane).

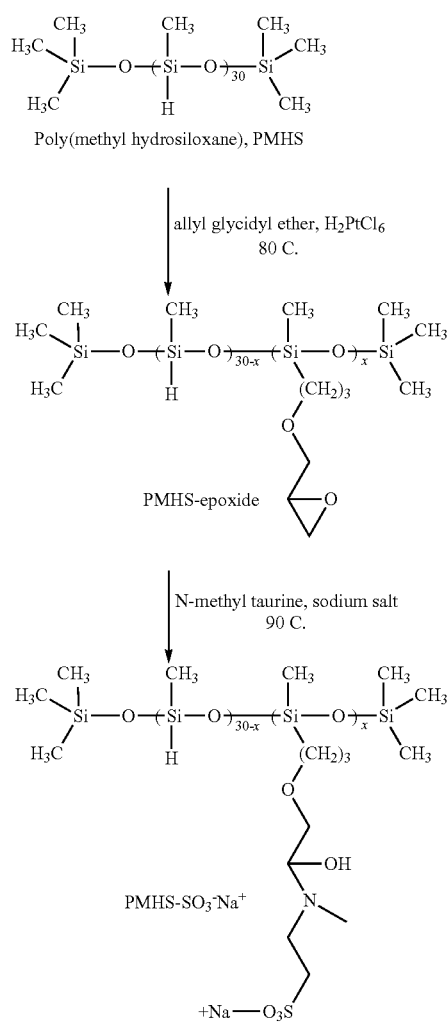

Generally, functionalization of an ionic and nonionic polysiloxane can be manipulated by controlling the amount of polyether or ionic groups added. In particular, functionalization of PMHS can be varied by varying the amount of allyl PEG, allyl glycidyl ether, and/or alkylimidazolium acrylate added to the reaction mixture. Addition of functional sites (e.g., polyether or ionic groups) increases the water solubility of ionic and nonionic polysiloxanes. The water solubility of the polymer depends on the number of functional sites added to the polysiloxane. Further, polysiloxanes can be functionalized with both a polyether and an ionic species by adding a polyether having an allyl group and an ionic compound having an allyl group to the same reaction mixture.

The functionalized PMHS can then be crosslinked into an elastomer having properties similar to a natural rubber by using the remaining Si—H groups via two possible pathways, a hydrosilylation reaction or a dehydrogenative coupling reaction. The hydrosilylation reaction uses a platinum catalyst such as platinum-divinyltetramethyldisiloxane complex and vinyl-functional polysiloxanes as crosslinkers. Examples of vinyl-functional polysiloxanes include divinyl-terminated PDMS or PPMS, poly(vinylmethylsiloxane) (PVMS) homopolymer, and copolymers of PVMS and PDMS or PPMS. The dehydrogenative coupling reaction uses a catalyst wherein the choice of catalyst depends on the coupling mechanism. Tin catalysts are predominately used in dehydrogenative coupling reaction where Si—H couples to Si—OH to form Si—O—Si linkages. Tin catalyst such as di-n-butyldilauryltin are used with silanol-functional polysiloxanes as crosslinkers. In addition to tin compounds, other transition metal complexes based on zinc, iron, cobalt, ruthenium, iron, rhodium, iridium, palladium, and platinum can be used. Specific examples include zinc octoate, iron octoate, and Wilkinson's catalyst (rhodium-based metal salt; $(PhP)_3RhCl$). Precious metal catalysts (predominately platinum but rhodium as well) are used in hydrosilylation reactions where Si—H reacts with a terminal vinyl bond to form Si—$CH_2$—$CH_2$—Si. Free radical initiators (thermal and/or UV generated) can be used to crosslink vinyl, acrylate, or methacrylate containing polysiloxanes. Tin and/or titanium compounds are used to catalyze condensation cure systems where Si—OH groups react with a variety of reactive groups (alkoxy, acetoxy, oxime, enoxy, and amines) to form Si—O—Si bonds. These condensation cure systems are moisture sensitive and will react in the presence of water only, but using titanium and/or tin compounds speeds up that reaction. Examples of silanol-functional polysiloxanes include disilanol-terminated PDMS or poly(trifluoropropylmethylsiloxane) (PTFPMS), disilanol-terminated copolymers of PPMS and PDMS, and silanol-trimethylsilyl modified Q resins. The crosslink density affects the material's properties and enzyme retention in the immobilization matrix.

Other variables to this immobilization procedure include annealing temperature (4° C.-60° C. for bovine carbonic anhydrase (BCA) or to 80° C. for human carbonic anhydrase (HCA)) and tin catalyst choice and loading. In addition, to dibutyldilauryltin, bis(2-ethylhexanoate)tin, dimethylhydroxy(oleate)tin, and dioctyldilauryltin can be used as the catalyst. As the annealing temperature increases, the amount of tin catalyst needed to maintain a fast reaction rate (solidifying in 30 minutes or less) decreases and ranges from about 0.01 to about 10 vol. %, preferably about 0.2 to about 4 vol. %.

The final geometry of the polymer pieces can be varied as well. The cylinder diameter and length can be changed using different acrylic molds. Alternatively, the polysiloxane can be coated onto a solid support. Ideally, the surface of the solid support will be functionalized with Si—OH groups so that it can covalently bind to the polysiloxane during the tin-catalyzed crosslinking reaction. The type and molecular weight of the disilanol-terminated polymer crosslinker can also be varied to change the composite polysiloxane properties (e.g., density, mechanical strength, etc.). Alternatives to PDMS-$(OH)_2$ are the disilanol terminated diphenylsiloxane-dimethylsiloxane copolymer, disilanol terminated poly(trifluoropropylmethylsiloxane), and disilanol terminated poly(diphenylsiloxane).

Additionally, PMHS-g-PEG can be crosslinked via a different mechanism (hydrosilylation) using precious metal catalysts and vinyl-containing polysiloxane crosslinkers of various molecular weights. Useful catalysts for this reaction are platinum-divinyltetramethyldisiloxane complex, platinum-cyclovinylmethylsiloxane complex, and tris(dibutylsulfide)rhodium trichloride at loadings of about 0.01 to about 5 vol. %, preferably about 0.02 to about 0.5 vol. %. Examples of vinyl-containing polysiloxane crosslinkers are divinyl terminated poly(dimethylsiloxane), divinyl terminated diphenylsiloxane-dimethylsiloxane copolymer, divinyl terminated poly(phenylmethylsiloxane), poly(vinylmethylsiloxane), vinyl Q resins, vinyl T structure polymers, vinylmethylsiloxane-dimethylsiloxane copolymer, and poly(vinylphenylsiloxane co-phenylmethylsiloxane).

Enzyme Encapsulation Process

In order to encapsulate an enzyme in polysulfone, the enzyme must not be deactivated by the solvent used for dissolving the polymer. When preparing the enzyme encapsulated polymer beads, the enzyme is dissolved into a solvent with a surfactant. Next the polysulfone is added to the solution and stirred until completely dissolved. The polysulfone/enzyme solution is held at room temperature until complete mixing has been achieved. The dissolved polysulfone/enzyme solution is then added dropwise to a water, an alcohol, or a water-alcohol solution; this process forms polymeric beads as shown in FIG. 1. Additionally, FIG. 1 illustrates the retention of soluble species in the polymeric bead. The blue bead was created by mixing in 20 mg/mL copper phthalocyanine into the 20 wt. % polysulfone in 1-methylpyrrolidone solution. The solution is then added dropwise into a beaker of water forming the beads. The beads are washed repeatedly with water, alcohol, and carbonate solution to wash any free dye off the bead.

To immobilize an enzyme in alginate, a 2% unmodified alginate solution is loaded with enzyme, and then added dropwise into a 2 wt. % calcium chloride solution and stirred for at least thirty minutes. The enzyme encapsulated alginate beads are then removed and gently dried with paper towels. Next, the beads are rolled into a 20 wt. % polysulfone solution by hand to obtain a thin polysulfone film encapsulating the alginate bead. This film is needed because alginate beads dissolve in sodium carbonate solution without a polysulfone coating, but the enzyme is retained in the alginate when a thin film of polysulfone coats the bead. This procedure could be used for other polymers to control substrate diffusion.

To immobilize an enzyme in poly(vinylbenzyl chloride) (PVBC), a PVBC solution was made in a water displaceable solvent such as dioxane or 1-methylpyrrolidone. Then carbonic anhydrase was added to the solution and stirred until a uniform dissolution occurred. Once the solution is adequately dispersed, a diamine crosslinker is added and stirred until the solution is sufficiently viscous to form a bead. However, the stirring should not be long enough to allow the solution to gel. When the viscosity is low enough to be easily pipetted using a transfer pipette, the solution is added dropwise into a beaker of water and stirred to remove the excess solvent.

To immobilize an enzyme in polysulfone-graft-polyethylene glycol (PSf-g-PEG) polymers, dry PSf-g-PEG and a low boiling point solvent (e.g., dichloromethane, 1,2-dichloroethane, 1,4-dioxane, chloroform, tetrahydrofuran, toluene, 2-butanone, benzene, ethyl acetate, acetonitrile, acetone) is placed in a vessel until the PSf-g-PEG dissolves. A support material (e.g., porous lava rocks, porous silica, porous ceramics, porous polymeric beads or other appropriate support) is placed in a beaker and enzyme (e.g., carbonic anhydrase) is added with stirring. Once homogenized, PSf-g-PEG is added and stirred to coat the support material. The contents are stirred continuously until the solvent evaporates. The immobilized carbonic anhydrase-coated support material is placed in the vacuum oven to remove residual solvent and stored in bicarbonate solution.

Alternatively, enzyme can be immobilized in PSf-g-PEG by placing dry PSf-g-PEG in a vessel with a water-miscible solvent (e.g., N-methylpyrrolidone, 1,4-dioxane, dimethyl sulfoxide, tetrahydrofuran, acetonitrile, acetone) and stirred until the PSf-g-PEG dissolves. Once the PSf-g-PEG is dissolved, enzyme (e.g., carbonic anhydrase) is added and mixed thoroughly. The enzyme/PSf-g-PEG solution is added dropwise to deionized water to form polymer beads. The beads are stored in bicarbonate solution.

Core Component

The core is any particle that provides a support for the immobilized enzyme layer and that can be spray-dried. The core particle can be, for example, a polymer particle, a carbon particle, a zeolite particle, a metal particle, a ceramic particle, a metal oxide particle, a silica particle, or a combination thereof. In some embodiments, the core particle is an inert core particle. In various embodiments, the core particle is not a polymer particle. Preferred core particles do not adversely affect the stability of the enzyme or a chemical transformation involving the enzyme. For particular applications, the core particles have an average diameter from about 200 nm to about 100 μm, depending upon the intended use of the particles when coated with the immobilized enzyme. For other applications, the core particles can have dimensions appropriate to the system designed for the application.

Methods of Preparing Coated Particles

The coated particles are prepared by mixing a solution comprising an enzyme with a suspension comprising at least one core particle, an immobilization material, and a liquid medium and spray-drying the resulting mixture. The solution, suspension, and spray-drying step are described in more detail below.

An enzyme solution comprising the enzyme and a solvent is used in the coating procedure. The enzyme is combined with a solvent and mixed until a solution is formed. Acceptable enzymes are described in more detail above. The solvent can be an aqueous solution, particularly a buffer solution, such as an acetate buffer or phosphate buffer. The buffer pH is designed to provide an acceptable pH for the particular enzyme to be immobilized. Also, in various embodiments, the enzyme solution can contain an electron mediator as described above.

A suspension is prepared by combining a core particle, the desired immobilization material and a liquid medium. Exemplary core particles and immobilization materials are described above. The liquid medium can be a solvent or buffer, such as an acetate buffer or phosphate buffer. When a buffer is used as the liquid medium, the buffer pH is selected to provide an acceptable pH for the particular enzyme to be immobilized and coated.

Once the enzyme solution and the suspension are prepared, they are combined and mixed well. The resulting mixture is then dried. A preferred drying method is spray-drying because the drying also results in coating of the core particles with the immobilized enzyme layer. Conventional spray drying techniques can be used in the methods of the invention. Alternatives to spray-drying include other conventional processes for forming coated particles, such as fluidized bed granulation, spray dry granulation, rotogranulation, fluidized bed/spray drying granulation, extrusion and spheronization.

In some of the various embodiments, the solution comprises from about 0.1 wt. % to about 15 wt. % of the enzyme and about 85 wt. % to about 99.1 wt. % of a solvent, and the suspension comprises from about 0.1 wt. % to about 50 wt. % of the core particles, from about 4 wt. % to about 10 wt. % of the enzyme immobilization material, and from about 50 wt. % to about 75 wt. % of the liquid medium. Other ways to make the casting solution include mixing the particles and the enzyme together in buffer to form a suspension and then adding solubilized immobilization material to complete the mixture or by combining all of the materials at once to form a suspension.

In various preferred embodiments, a mixture of enzyme and enzyme immobilization material can be coated onto supporting particles using a spray coating/drying technique. For example, an airbrush (e.g., Paasche VL series) can be used to generate an aerosol of the components of the mixture and propel them towards a target. The aerosol is generated using compressed nitrogen gas regulated at about 25 psi. The mixture is airbrushed onto a surface such as a polycarbonate shield from a distance of about 40 cm from the tip of the airbrush to the shield. The airbrush can be moved in a raster pattern while moving vertically down the polycarbonate target in a zigzag pattern applying the casting solution. This procedure is used to minimize the coating thickness on the shield and minimize the particle-particle interaction while drying. The casting solution is allowed to dry on the shield for about 20 minutes before being collected by a large spatula/scraper.

For other particles that cannot be coated using the spray drying technique described above, the particles can be coated by methods known in the art such as dip coating, brush coating, spin coating, and the like.

Support or Substrate

Once the enzyme has been immobilized within the enzyme immobilization material, this immobilized enzyme can be deposited on a support. The substrate can be a material that provides the desired mechanical support necessary for the selected use. For example, the support may be a filter, a wire mesh, porous polymer, organic and inorganic membrane, and the like when the immobilized enzyme is used as a catalyst for a chemical transformation.

Aqueous Liquid

As described above, the aqueous liquid is contacted with the $CO_2$-containing gas to help absorb the $CO_2$ and increase the $CO_2$ concentration in the aqueous liquid. In many preferred embodiments, the aqueous liquid comprises a base. The base is a proton acceptor. The base is water soluble and does not denature the carbonic anhydrase. The base can be a metal hydroxide, a quaternary ammonium hydroxide, a metal carbonate, a quaternary ammonium carbonate, a quaternary ammonium alkoxide, a metal amide, a metal alkyl, a metal alkoxide, metal silanoate, an amine, an alkanolamine, a conjugate base of a weak acid, or a combination thereof. The metal hydroxides can include lithium hydroxide, sodium hydroxide, potassium hydroxide, rubidium hydroxide, cesium hydroxide, magnesium hydroxide, calcium hydroxide, strontium hydroxide, barium hydroxide, or a combination thereof. Also, ammonium hydroxide can be used in the aqueous liquid. The metal carbonate can be lithium carbonate, sodium carbonate, potassium carbonate, rubidium carbonate, cesium carbonate, magnesium carbonate, calcium carbonate, strontium carbonate, barium carbonate, ammonium carbonate, a carbonate salt of an organic cation, or a combination thereof. For example, the carbonate salt of an organic cation can be a tetraalkyleammonium carbonate (e.g., tetramethylammonium carbonate, tetraethylammonium carbonate, tetrapropylammonium carbonate, tetrabutylammonium carbonate, tetrapentylammonium carbonate, or tetrahexylammonium carbonate) an alkyltrimethyl ammonium carbonate (e.g., ethyltrimethyl ammonium carbonate, propyltrimethyl ammonium carbonate, butyltrimethyl ammonium carbonate, pentyltrimethyl ammonium carbonate, hexyltrimethyl ammonium carbonate, hepyltrimethyl ammonium carbonate, octyltrimethyl ammonium carbonate, nonyltrimethyl ammonium carbonate, decyltrimethyl ammonium carbonate, dodecyltrimethyl ammonium carbonate, or undecyltrimethyl ammonium carbonate), an alkyltriethylammonium carbonate (e.g., methyltriethyl ammonium carbonate, propyltriethyl ammonium carbonate, butyltriethyl ammonium carbonate, pentyltriethyl ammonium carbonate, hexyltriethyl ammonium carbonate, hepyltriethyl ammonium carbonate, octyltriethyl ammonium carbonate, nonyltriethyl ammonium carbonate, decyltriethyl ammonium carbonate, dodecyltriethyl ammonium carbonate, or undecyltriethyl ammonium carbonate), or a combination thereof.

The quaternary ammonium hydroxide, quaternary ammonium carbonate, or quaternary ammonium alkoxide can be benzyltrimethylammonium hydroxide, choline hydroxide, diethyldimethylammonium hydroxide, dimethyldodecylethylammonium hydroxide, N,N,N,N',N',N'-hexabutylhexamethylenediammonium dihydroxide, hexadecyltrimethylammonium hydroxide, hexamethonium hydroxide, triethylmethylammonium hydroxide, tributylmethylammonium hydroxide, trihexyltetradecylammonium hydroxide, tetrapropylammonium hydroxide, tetrabutylammonium hydroxide, tetraoctadecylammonium hydroxide, methyltripropylammonium hydroxide, tetrabutylammonium ethoxide, tetraethylammonium hydroxide, tetrahexylammonium hydroxide, tetrakis(decyl)ammonium hydroxide, tetramethylammonium hydroxide, trimethylphenylammonium hydroxide, or a combination thereof.

The metal amide, metal alkoxide, or metal silanoate can be lithium tert-amoxide, lithium bis(trimethylsilyl)amide, lithium diethylamide, lithium dimethylamide, lithium diisopropylamide, sodium bis(trimethylsilyl)amide, potassium bis (trimethylsilyl)amide, lithium dicyclohexylamide, lithium trimethylsilanolate, sodium methoxide, potassium methoxide, lithium methoxide, sodium ethoxide, potassium ethoxide, lithium ethoxide, lithium isopropoxide, sodium tert-butoxide, potassium tert-butoxide, lithium tert-butoxide, sodium tert-pentoxide, potassium tert-pentoxide, magnesium ethoxide, magnesium di-tert-butoxide, sodium trimethylsilanolate, potassium trimethylsilanolate, or a combination thereof.

The amine can be a cyclic amine of 2-(2-chloro-6-fluorophenyl)ethylamine, 1,4-diazabicyclo[2.2.2]octane (DABCO® 33-LV), 1,5-diazabicyclo[4.3.0]non-5-ene, 1,4-diazabicyclo[2.2.2]octane, 1,8-diazabicyclo[5.4.0]undec-7-ene, 4-(dimethylamino)pyridine, 2,6-lutidine, piperidine, 1,8-(dimethylamino)naphthalene, 2,2,6,6-tetramethylpiperidine, 2,8,9-triisobutyl-2,5,8,9-tetraaza-1-phosphabicyclo [3.3.3]undecane, tripelennamine, aniline, benzylamine, N-methyl aniline, imidazole, pyrrole, pyridine, morpholine, or a combination thereof.

The amine can be a primary amine, a secondary amine, a tertiary amine, or a combination thereof. The primary amine can be methylamine, ethylamine, propylamine, iso-propylamine, butylamine, iso-butylamine, sec-butylamine, tert-butylamine, pentylamine, iso-pentylamine, sec-pentylamine, tert-pentylamine, hexylamine, iso-hexylamine, sec-hexylamine, tert-hexylamine, ethylenediamine, (2-methylbutyl)

amine, 2-aminopentane, 3-(tert-butoxy)propylamine, 2-amino-6-methylheptane, 1-ethylpropylamine, or a combination thereof. Further, the secondary amine can be dimethylamine, diethylamine, dipropylamine, dibutylamine, dipentylamine, dihexylamine, methylethylamine, methylpropylamine, methylbutylamine, ethylpropylamine, ethylbutylamine, N-ethylmethylamine, N-isopropylmethylamine, N-butylmethylamine, N-ethylisopropylamine, N-tert-butylmethylamine, N-ethylbutylamine, 3-isopropoxypropylamine, chloro(diethylamino)dimethylsilane, 2,2'-(ethylenedioxy)bis(ethylamine), 1,3-bis(chloromethyl)-1,1,3,3-tetramethyldisilazane, N-tert-butylisopropylamine, N,N-diethyltrimethylsilylamine, di-sec-butylamine, or a combination thereof. Additionally, the tertiary amine can be trimethylamine, triethylamine, tripropylamine, tributylamine, dimethylethylamine, dimethylpropylamine, dimethylbutylamine, diethylmethylamine, diethylpropylamine, diethylbutylamine, N,N-diisopropylmethylamine, N-ethyldiisopropylamine, N,N-dimethylethylamine, N,N-diethylbutylamine, 1,2-dimethylpropylamine, N,N-diethylmethylamine, N,N-dimethylisopropylamine, 1,3-dimethylbutylamine, 3,3-dimethylbutylamine, N,N-dimethylbutylamine, or a combination thereof.

In various embodiments, the amine is a tertiary amine, for example, trimethylamine, triethylamine, tripropylamine, tributylamine, dimethylethylamine, dimethylpropylamine, dimethylbutylamine, diethylmethylamine, diethylpropylamine, diethylbutylamine, N,N-diisopropylmethylamine, N-ethyldiisopropylamine, N,N-dimethylethylamine, N,N-diethylbutylamine, 1,2-dimethylpropylamine, N,N-diethylmethylamine, N,N-dimethylisopropylamine, 1,3-dimethylbutylamine, 3,3-dimethylbutylamine, N,N-dimethylbutylamine, or a combination thereof.

The alkanolamine can be 2-amino-2-(hydroxymethyl)-1,3-propanediol (Trizma® base), propanolamine, ethanolamine, diethanolamine, dimethylethanolamine, N-methylethanolamine, triethanolamine, or a combination thereof.

The conjugate base of a weak acid could be an acetate, a citrate, a succinate, an oxalate, a malate, a malonate, a phosphate, a phosphonate, a sulfate, a sulfamate wherein the counterion can be a positive ion such as alkali metal, alkaline earth metal, or ammonium cations.

Unless otherwise indicated, the alkyl groups described herein are preferably lower alkyl containing from one to eight carbon atoms in the principal chain and up to 20 carbon atoms. Alkyls may be substituted or unsubstituted and straight or branched chain. Examples of unsubstituted alkyls include methyl, ethyl, n-propyl, i-propyl, n-butyl, i-butyl, s-butyl, t-butyl, n-pentyl, i-pentyl, s-pentyl, t-pentyl, and the like. The term "substituted," as in "substituted alkyl," means that various heteroatoms such as oxygen, nitrogen, sulfur, phosphorus, and the like can be attached to the carbon atoms of the alkyl group either in the main chain or as pendant groups. For example, the substituted alkyl groups can have —C—X—C— fragments in the main chain wherein the X is a heteroatom. Further, the substituted alkyl groups can have at least one hydrogen atom bound to a carbon atom replaced with one or more substituent groups such as hydroxy, alkoxy, alkylthio, phosphino, amino, halo, silyl, nitro, esters, ketones, heterocyclics, aryl, and the like.

Having described the invention in detail, it will be apparent that modifications and variations are possible without departing from the scope of the invention defined in the appended claims.

EXAMPLES

The following non-limiting examples are provided to further illustrate the present invention.

Example 1

Bench-Scale Packed Bed Reactor

A flow diagram for a packed bed reactor for hydrating $CO_2$ is shown in FIG. 3. A packed bed reactor having the parts indicated in FIG. 3 was fabricated. The reactor housing was made of 3 inch diameter PVC pipe with PVC caps on each end. The packing material in the reactor was commercially available lava rock covered with 0.18 wt. % by weight immobilized carbonic anhydrase. The immobilized carbonic anhydrase is described below. Carbon dioxide gas entered the reactor through a sparger at the base of the reactor and exited to atmospheric pressure at the top of the reactor. The aqueous solution of 500 mM sodium carbonate entered at the top of the reactor and exited on the side of the reactor. This configuration allowed maintenance of the liquid level in the reactor without use of a second pump.

The carbonic anhydrase was coated onto the packing and then tested. Sample 1A used a 100 mL packing volume and a 239 g packing weight for 0.18 wt. % carbonic anhydrase. A solution of 428 mg bovine carbonic anhydrase, 0.425 mL Triton X-100, 84.575 mL 0.02M Trissulfate buffer at pH 8.3, and 15 mL 15% tetraethylammonium bromide-modified Nafion® was prepared to form an immobilized enzyme solution. The solution was vortexed for approximately five minutes. The enzyme immobilization solution was pipetted onto the lava rock and allowed to dry overnight at 4° C. and then placed in a vacuum oven at room temperature and −30 mmHg for 2 hours before placing the lava rock into the reactor. Sample 1B had the same packing volume and packing weight, but contained no carbonic anhydrase for use as a control.

The reactor inlet flow rates, compositions of gas and liquid streams, packing weight, catalyst weight, and mol $CO_2$/(h L) sequestered were collected. The mol $CO_2$/(h L) sequestered was calculated based on the amount of sodium hydroxide/ potassium hydroxide used to reclaim the carbonate solution through the pH stat. The overall system is illustrated in FIG. 3. A 0.5 M sodium carbonate ($Na_2CO_3$) solution at a 4.18 L/h and a $CO_2$ flow rate of 7308 L/h was used in the reaction (The reactor conditions were not optimized).

Figure 4:
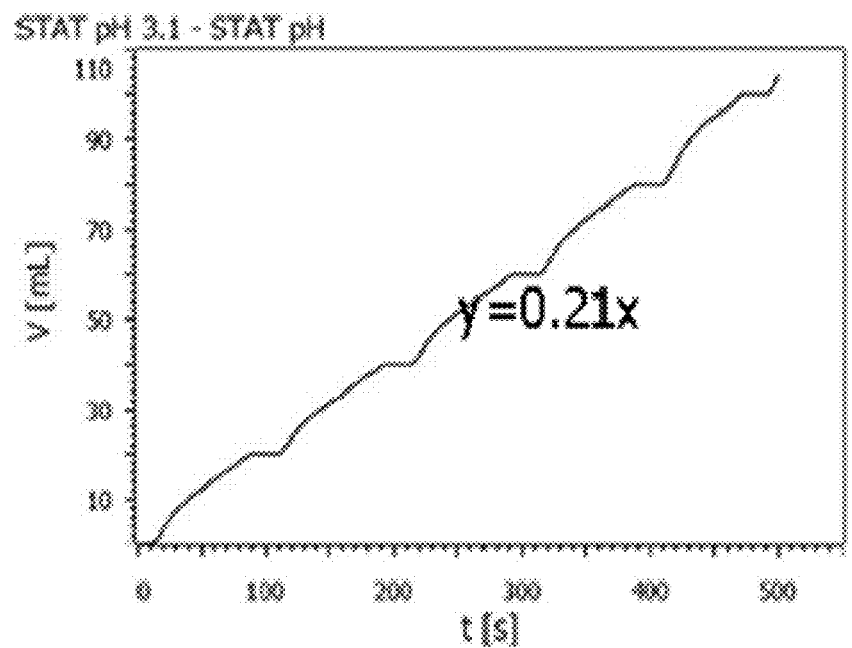
FIG. 4 is a graph of volume of 2M sodium hydroxide added to the reactor to keep the pH constant as the $CO_2$ is converted to bicarbonate versus time wherein the carbonic anhydrase was treated with Triton-X 100 and immobilized in tetraethylammonium-modified Nafion®.

When using the pH stat to determine how much carbon dioxide was sequestered, the dosing unit added a volume of 2 M sodium hydroxide (NaOH) in a recorded amount of time. A graph of the volume (mL) of sodium hydroxide added per unit time(s) with and without immobilized carbonic anhydrase are given in FIGS. 4 and 5, respectively.

The experiment wherein the packing material was coated with immobilized carbonic anhydrase showed that 0.719 mol/h of carbon dioxide was sequestered whereas the experiment wherein the packing material was not coated with enzyme showed that 0.471 mol/h of carbon dioxide was sequestered. The amount of carbon dioxide removed is calculated by the equation $$\text{molCO}_2 = \left(\frac{\Delta V}{\Delta t}\right)[\text{NaOH}]\left(\frac{\text{molCO}_2}{2\ \text{molNaOH}}\right),$$

where $\Delta V$ is the change in volume and $\Delta t$ is the change in time.

Example 2

Dehydration of Bicarbonate Solutions Using Carbonic Anhydrase

The rate of reaction for conversion of bicarbonate ions to $CO_2$, water and carbonate ions was monitored by the change in pH as a function of time in a closed system. The system parameters that were altered include temperature of the reaction, initial bicarbonate concentration, and reaction time. The experiments were carried out in a 200 mL three necked flask containing 80 mL of sodium bicarbonate solution with 0.313 mg/mL carbonic anhydrase either free in solution or immobilized on a porous support added to the solution. The temperature of the system was set to a constant set point using a thermostatically controlled water bath. Nitrogen gas was introduced into the system at a rate of 50 standard cubic centimeters per minute (sccm) through a fritted glass sparger of medium porosity to remove any carbon dioxide produced during the course of the reaction. The initial pH of the system was approximately 8.4 and the change in pH was monitored by a temperature compensated pH probe and the data was logged at three second intervals. All enzymatic systems tested were compared to comparable blanks of either a bicarbonate solution containing no enzyme or a bicarbonate solution containing support material having no immobilized enzyme coated thereon.

Example 2A

Free Enzyme in a Bicarbonate Solution

Figure 6:
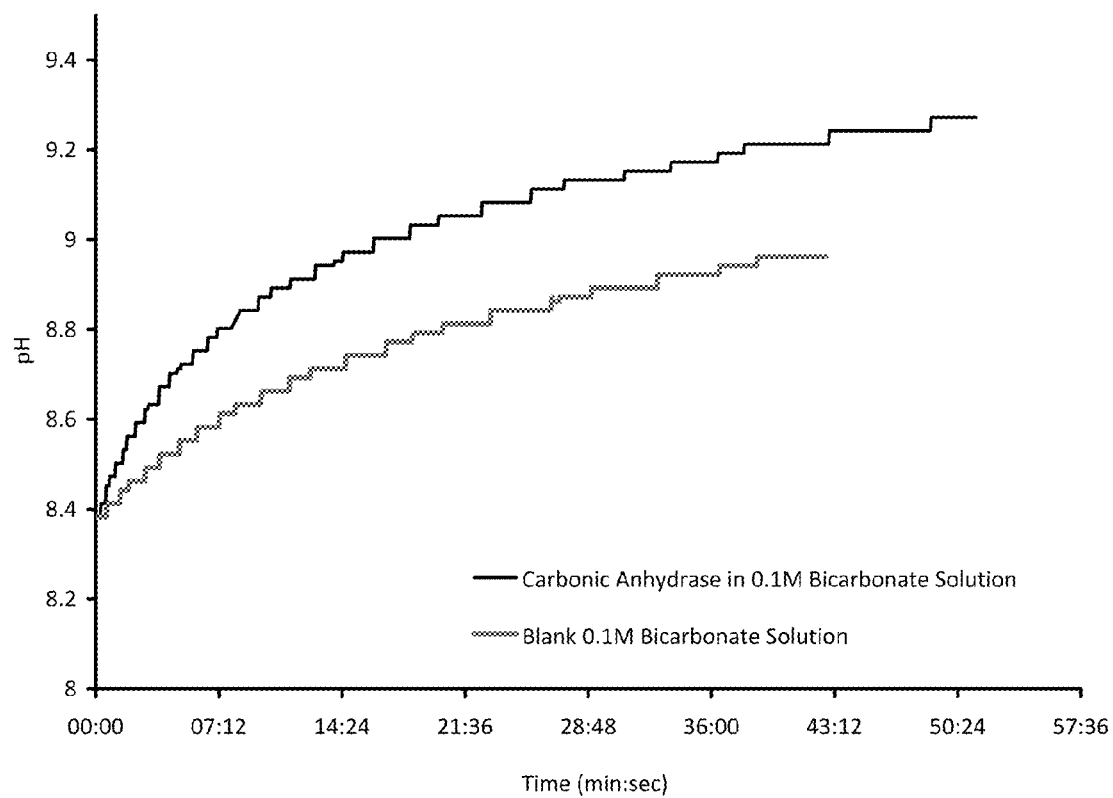
FIG. 6 is a graph of the pH versus time for a reaction of bicarbonate conversion to carbon dioxide catalyzed by non-immobilized carbonic anhydrase and no enzyme as described in example 2A wherein the experiment was performed in 0.1M $Na_2CO_3$, 50 sccm $CO_2$, at 40° C., and using 0.313 mg/mL carbonic anhydrase and a run time of 50 minutes.

Dehydration of bicarbonate catalyzed by non-immobilized carbonic anhydrase was compared to dehydration of bicarbonate without a catalyst. A graph of the pH versus the reaction time comparing the carbonic anhydrase catalyzed reaction to the uncatalyzed system is shown in FIG. 6. The temperature of this reaction was set at 40° C. and the initial concentration of the bicarbonate in solution was 0.1 M. The solution was stirred using an overhead glass rod fitted with a polytetrafluoroethylene (PTFE) paddle. Data collection for the reaction was initiated when the enzyme was introduced into the system and was continuously collected for approximately 50 minutes. Initially, the enzymatic system demonstrated a higher rate of pH change for the overall system when compared to the blank and the faster rate continued throughout the entire experiment. At 45 minutes, the pH of the uncatalyzed reaction mixture was 8.9 compared to over 9.2 for the carbonic anhydrase catalyzed reaction mixture after the same elapsed time. The carbonic anhydrase-catalyzed reaction mixture had a 0.5 pH unit increase in one third of the time as compared to the uncatalyzed reaction.

Figure 7:
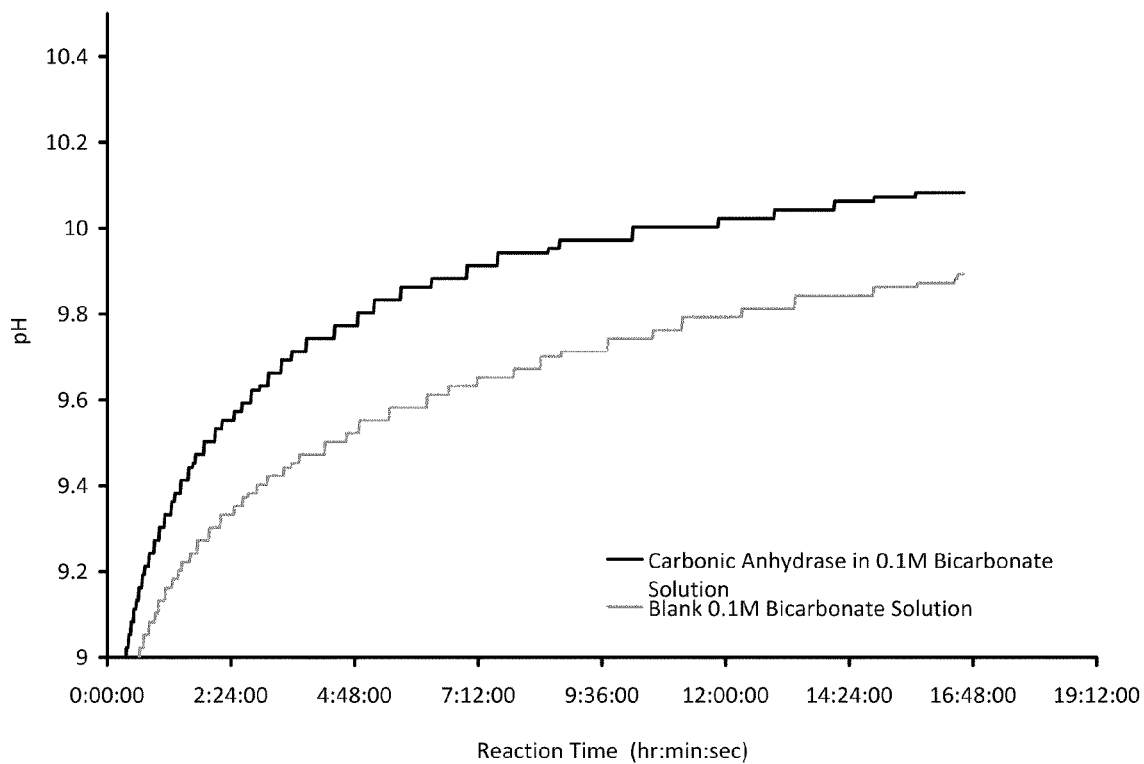
FIG. 7 is a graph of the pH versus time for a reaction of bicarbonate conversion to carbon dioxide catalyzed by non-immobilized carbonic anhydrase and no enzyme as described in example 2A wherein the experiment was performed in 0.1M $Na_2CO_3$, 50 sccm $CO_2$, at 40° C., and using 0.313 mg/mL carbonic anhydrase and a run time of 16 hours.

When the reaction was allowed more time for completion (up to 16 hours), the carbonic anhydrase-catalyzed reaction mixture maintained a higher pH value than the uncatalyzed reaction mixture throughout the entire experiment. A graph of the pH of the reaction mixture versus time for the 16 hour experiment is shown in FIG. 7. The carbonic anhydrase solution ended at a pH of 10.1 after 16 hours. A sodium carbonate solution has a pH of approximately 11.3, so the concentration of carbonate was higher in the reaction mixture that was allowed to react longer.

Example 2B

Varying the Bicarbonate Concentration

Figure 8:
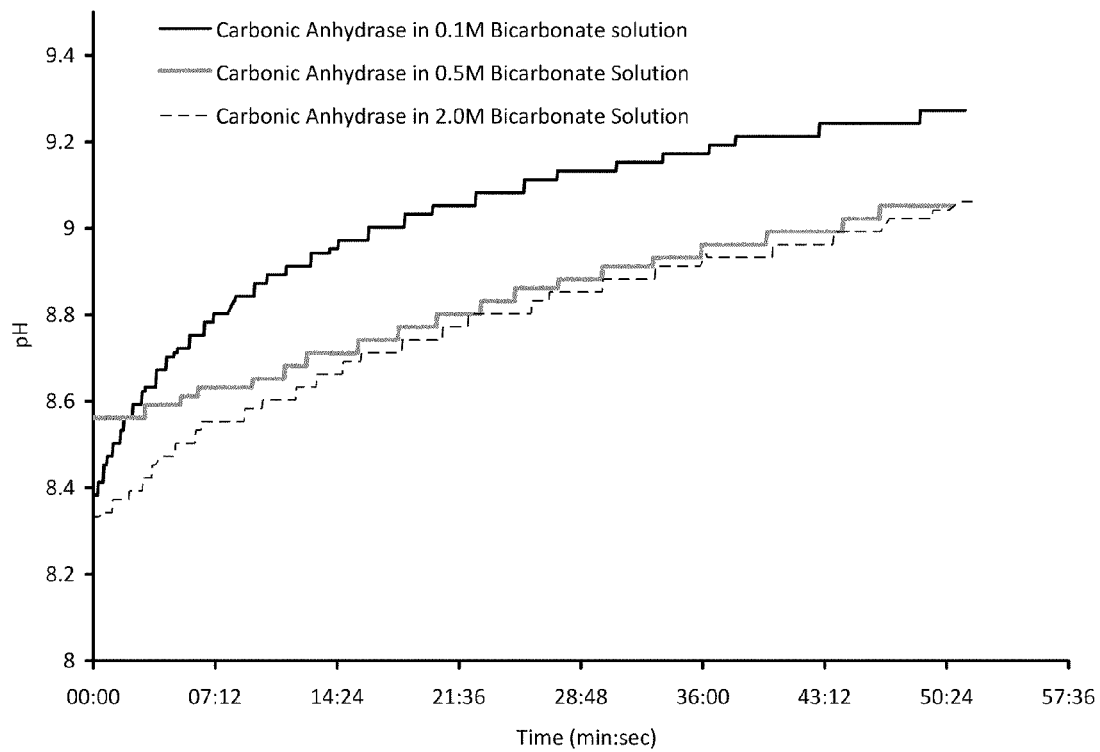
FIG. 8 is a graph of the pH versus time for a reaction of bicarbonate conversion to carbon dioxide catalyzed by non-immobilized carbonic anhydrase as described in example 2B wherein the experiment was performed in 0.1M, 0.5M, and 2M $Na_2CO_3$, 50 sccm $CO_2$, at 40° C., and using 0.313 mg/mL carbonic anhydrase.

The initial concentration of bicarbonate was varied between values of 0.1 M and 2.0 M for the non-immobilized enzyme system. FIG. 8 is a graph of the pH versus the reaction time for three carbonic anhydrase catalyzed reaction mixtures having an initial bicarbonate concentration of 0.1, 0.5, and 2.0 M. The largest change in pH was observed in the lowest concentration system. As the concentration of bicarbonate increased to 0.5 M the change in the pH of the system was comparable to that of the blank system at 0.1 M, but still slightly better than the blank at 0.5 M. The rate of pH increase and the final pH value slowed only slightly when the concentration of the bicarbonate was increased to 2.0 M when compared to the 0.5 M system. The inverse relation of the system response to increasing bicarbonate levels could have many causes. For example, the buffering capacity of the bicarbonate/carbonate solution increases as the concentration of the system increases because bicarbonate is converted to carbonate, thus causing the pH not to rise as fast as it would without such buffering. Further, the particular strain of bovine carbonic anhydrase used may favor the carbon dioxide hydration reaction over that of the bicarbonate dehydration reaction and as the reaction progressed, the carbonic anhydrase preferentially converted the newly formed carbonate and carbon dioxide back to the bicarbonate form. Finally, the combined effects of higher ionic concentrations and elevated temperatures has been shown to reduce the activity of free carbonic anhydrase in the carbon dioxide hydration reaction and a similar result might be expected for the bicarbonate dehydration.

Example 2C

Reaction Temperature

Figure 9:
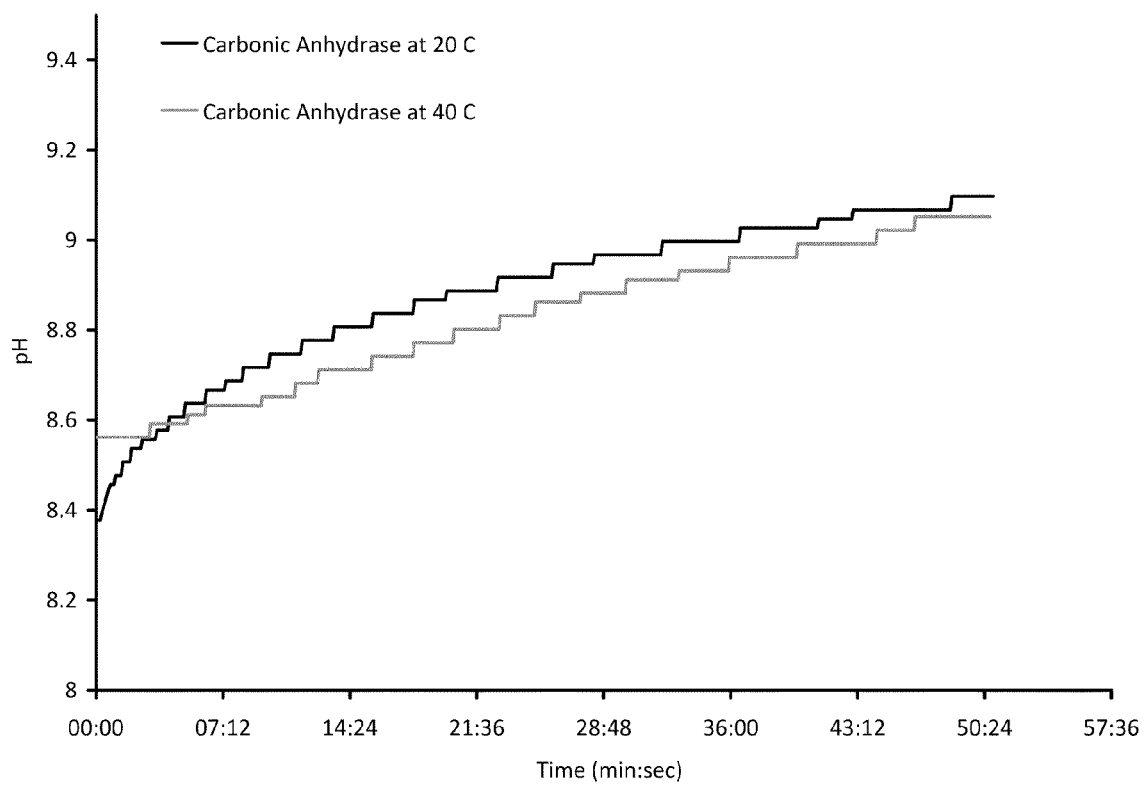
FIG. 9 is a graph of the pH versus time for a reaction of bicarbonate conversion to carbon dioxide catalyzed by non-immobilized carbonic anhydrase as described in example 2C wherein the experiment was performed in 0.5M $Na_2CO_3$, 50 sccm $CO_2$, at 20° C. and 40° C., and using 0.313 mg/mL carbonic anhydrase.

For an uncatalyzed reaction the rate of bicarbonate dehydration increases with increasing temperature of the reaction mixture. This was accomplished for the conversion of bicarbonate to carbonate by passing steam through the reaction mixture to increase the reaction temperature and thus, reaction rate, and to remove the carbon dioxide produced from the solution. A graph of the pH versus time for a carbonic anhydrase catalyzed conversion of bicarbonate to carbonate, $CO_2$, and water at 20° C. and 40° C. in a 0.1 M bicarbonate solution is shown in FIG. 9. For the non-immobilized enzyme system, the rate of reaction was slightly faster for the room temperature system over that of the higher temperature system. This may be the result of the combined effects of the high temperature and ionic concentration reducing the activity of the enzyme, similar to the results of the bicarbonate concentration studies previously.

Example 2D

Immobilized Carbonic Anhydrase

Figure 10:
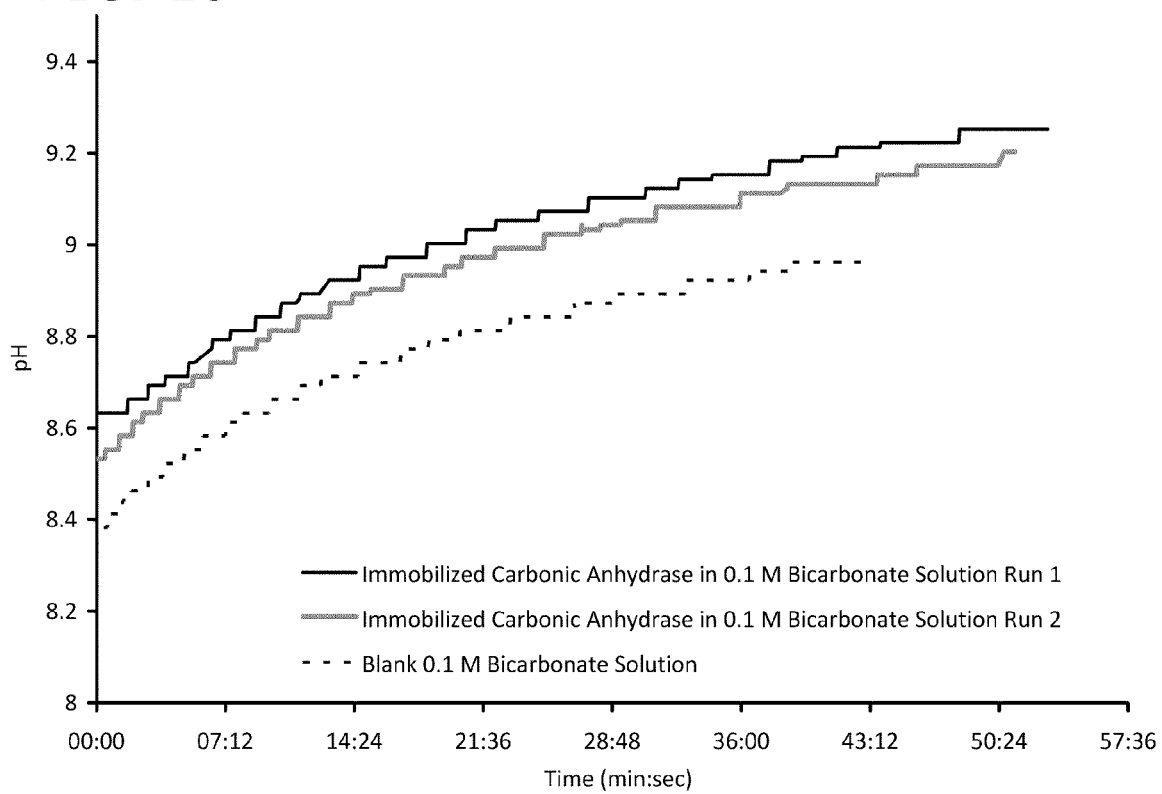
FIG. 10 is a graph of the pH versus time for a reaction of bicarbonate conversion to carbon dioxide catalyzed in two different runs by immobilized carbonic anhydrase as described in example 2D wherein the experiment was performed in 0.1M $Na_2CO_3$, 50 sccm $CO_2$, at 40° C., and using 0.313 mg/mL carbonic anhydrase treated with Triton-X 100 and immobilized in tetraethylammonium-modified Nafion®. An experiment wherein no carbonic anhydrase catalyst was used was also performed.

A graph of the pH versus time for the dehydration of bicarbonate using an immobilized carbonic anhydrase as a catalyst as compared to an uncatalyzed reaction mixture are shown in FIG. 10. The carbonic anhydrase in this example was encapsulated in tetraethylammonium bromide modified Nafion® onto washed and crushed lava rock supports (<1 cm) at a loading of 0.5% wt with 0.5% wt Triton X surfactant to maintain the enzyme hydration throughout the drying process.

The immobilized carbonic anhydrase was prepared as follows. Ethanol (2 mL) was added to tetraethyl ammonium bromide (TEAB) modified Nafion® (30 mg) to make a 5.0 wt. % solution. Carbonic anhydrase (50 mg) was added to 2 mL Trizma Base buffer solution (0.05 M, pH 7.6) to which 0.02 mL Triton X-100 was added at a total solution percentage of 0.5% and stirred until a uniform dissolution occurred. Once the solution was adequately dispersed, the TEAB-modified Nafion® solution was added and stirred until the solution was sufficiently homogenous. Once the immobilized enzyme solution was thoroughly mixed it was cast onto high surface area support and allowed to dry for 12 hours at 4° C. followed by 2 hours under vacuum. Alternatively, high surface carbon support was added to the immobilized enzyme solution, mixed, sprayed, and allowed to dry for several hours at room temperature.

The activity and performance of the immobilized enzyme was very similar to that of the free enzyme at the same salt concentration and temperature. Future testing on this sample will include exposure to higher temperatures (>50 C), higher concentrations of bicarbonate, and operating lifetime compared to non-immobilized enzyme. The same packing material with immobilized carbonic anhydrase was used for Run 1 and Run 2. This difference in performance may be attributed to the stability of the immobilized enzyme leaching after multiple washes and exposures to high carbonate concentration solutions.

Example 3

Immobilization of Carbonic Anhydrase TBAB-Modified Nafion® on Printex-95 Carbon

Bovine carbonic anhydrase (70 mg, purchased from Sigma-Aldrich) was combined with 10 mL of 20 mM Tris-$SO_4$ buffer of pH 8.3 and vigorously vortexed for approximately 5 seconds. Printex-95 carbon support material (0.5 gram) was combined with the enzyme solution and vigorously vortexed for one minute at room temperature. Tetrabutylammonium bromide (TBAB)-modified Nafion® (2 mL; 15% w/v) in 95% ethanol solution was added to the enzyme/support suspension and vigorously vortexed for one minute at room temperature. The enzyme/support/Nafion®/modifier solution was spray dried onto a mirror with nitrogen gas at about 20 psi. The resulting immobilized sample was allowed to dry at room temperature on the mirror for 30 minutes. Dried immobilized enzyme was scraped off the mirror and stored at about 4° C.

Enzyme activity was measured and calculated using a carbonic anhydrase assay as published by Sigma (revision date Jul. 22, 1996). The assay measures the rate of enzymatic $CO_2$ hydration by determining the net rate difference between a non-enzymatic blank and an enzyme-containing sample in the time required to decrease the pH of a buffered reaction mixture from 8.3 to 6.3. This enzyme activity assay was used in this and all subsequent examples.

Data obtained showed no net increase in reaction rate using immobilized enzyme relative to the non-enzymatic reaction. The amount of enzyme used in preparation and testing of the immobilized material, if active, was expected to show a pronounced rate increase.

Example 4

Immobilization of Carbonic Anhydrase in Tetraethylammonium Bromide (TEAB)-Modified Nafion® on Printex-95 Carbon Carbonic anhydrase was immobilized as described for Example 3 except that tetraethyl ammonium bromide was used as the modifier. Again, no net increase in rate was observed in the assay of this immobilized enzyme. The amount of enzyme used in preparation and testing of the immobilized material, if active, was expected to show a pronounced rate increase.

Example 5

Immobilization of Carbonic Anhydrase in Hexanal-Modified Chitosan on Poly(styrene-co-divinylbenzene) (PS-coDVB)

Carbonic anhydrase was immobilized as described in previous examples except that the polymer and modifier were chitosan and hexanal, respectively and the enzyme/polymer/modifier suspension was mixed with before spray drying. There was no net increase in the rate of $CO_2$ hydration over the non-enzymatic control reaction. The amount of enzyme used in preparation and testing of the immobilized material, if active, was expected to show a pronounced rate increase.

Example 6

Immobilization of Carbonic Anhydrase in Deacetylated Chitosan/Acetaldehyde on PS-co-DVB Carbonic anhydrase was immobilized and spray dried as described in previous examples except that the polymer and modifier were deacetylated chitosan and acetaldehyde. The support was poly(styrene-co-divinylbenzene) of 8 μm nominal particle size. No net enzyme activity was observed in this immobilization material. The amount of enzyme used in preparation and testing of the immobilized material, if active, was expected to show a pronounced rate increase.

Example 7

Immobilization of Triton X-100 Treated Carbonic Anhydrase in TEAB-Modified Nafion® on Printex-95 Carbon Bovine carbonic anhydrase (70 mg; purchased from Sigma-Aldrich) was combined with 10 mL of 20 mM Tris-$SO_4$ of pH 8.3 buffer and 0.050 mL Triton X-100. The immobilization and spray drying were done as in Example 2. Triton-treated enzyme immobilized by this procedure was tested for activity and had 1077 units of activity per gram material containing immobilized enzyme.

Example 8

Immobilization of Decylamine-Modified Carbonic Anhydrase in TEAB-Modified Nafion® on Printex-95 Carbon Carbonic anhydrase (70 mg) was combined with 5 mL of 75 mM MES buffer of pH 5.0 and then 7.8 mg N-(3-dimethylaminopropyl)-N'-ethylcarbodiimide hydrochloride (EDC) (4 mM) and 23.8 mg N-hydroxysulfosuccinimide sodium salt (sulfo-NHS) (11 mM). The solution was vigorously vortexed for five seconds. A second solution was made with 5 mL of 75 mM MES buffer of pH 5.0 was combined with 7.87 mg decylamine. This solution was combined with the EDC/enzyme solution and vigorously vortexed for 5 seconds. The combined solutions were held refrigerated overnight. Then the modified enzyme was mixed with 15% (w/v) TEAB-modified Nafion® and 1 gram Printex-95 and spray dried as described above. The enzyme activity assay showed that this modification had 3729 units of activity per gram material containing immobilized enzyme.

Example 9

Immobilization of (PEG) 8-Modified Carbonic Anhydrase on Printex-95 Carbon

Carbonic anhydrase (70 mg) was dissolved and used as described in Example 8 except that instead of decylamine, 11.0 mg (PEG) 8-modified carbonic anhydrase from Pierce Scientific was used. After overnight refrigeration, the modified enzyme preparation was combined with Printex-95 carbon and then spray dried as in Example 8. The enzyme assay showed that this immobilized modified carbonic anhydrase preparation had 3421 units of activity per gram material containing immobilized enzyme.

Example 10

Carbonic Anhydrase Immobilized in Polysulfone

Figure 11:
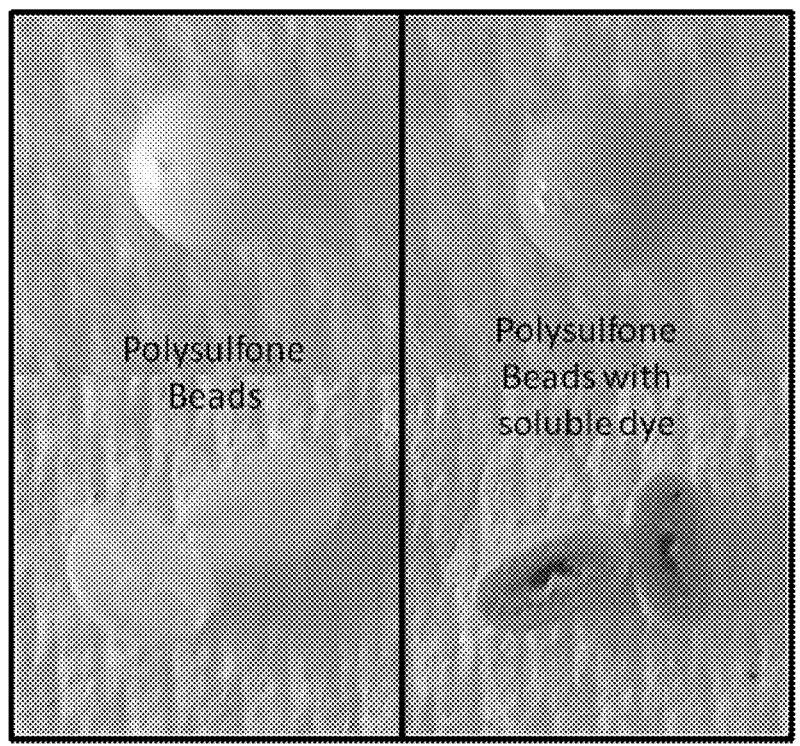
FIG. 11 is a picture of polysulfone beads and a cross sectional picture with and without a soluble dye present.

When immobilizing carbonic anhydrase in polysulfone, carbonic anhydrase was dissolved in 8 g 1-methylpyrrolidone and 0.05 mL Triton X-100. The polysulfone (2 g; 20 wt. %) was added to the solution and stirred until completely dissolved. The polysulfone/carbonic anhydrase solution was held at room temperature until complete mixing was achieved. The dissolved polysulfone/carbonic anhydrase solution was then added dropwise to a water, an alcohol, or a water-alcohol solution and formed polymeric beads (Sample 1A) as shown in FIG. 11. Blue beads (Sample 1B) were prepared by mixing 200 mg of copper phthalocyanine into 10 mL of the 20 wt. % polysulfone in 1-methylpyrrolidone solution. Next, the solution was added dropwise into a beaker of water, thus forming the beads. The beads were washed repeatedly with water, alcohol, and carbonate solution to wash any free dye off the bead.

Figure 12:
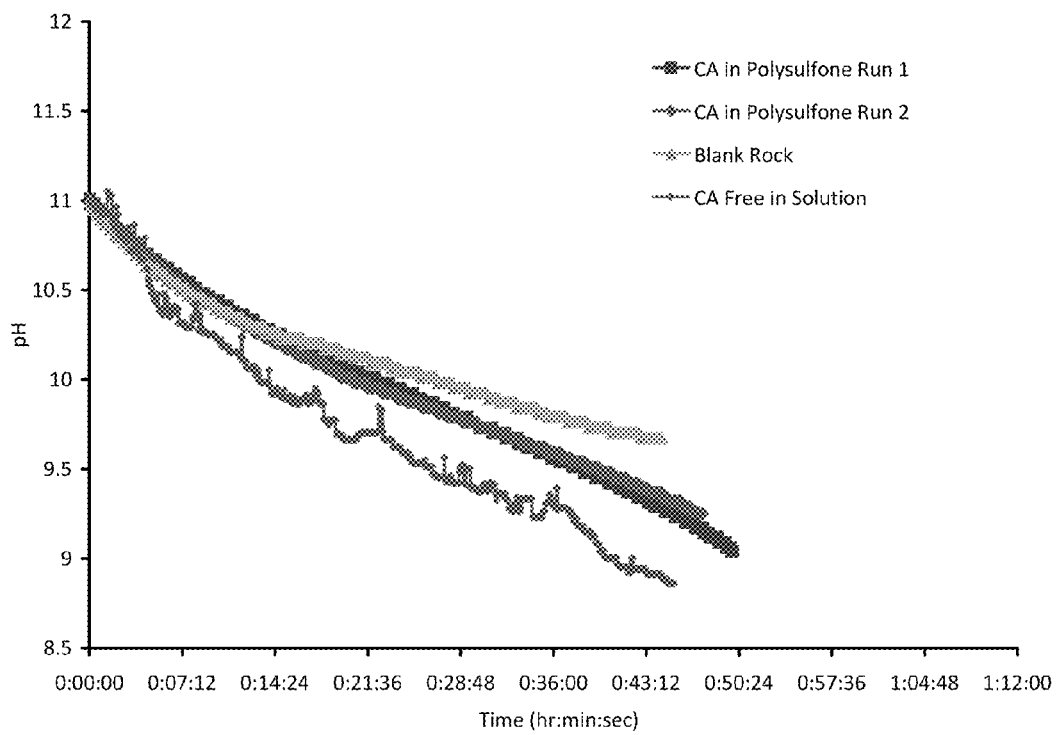
FIG. 12 is a graph of pH versus time for a reaction of carbon dioxide conversion to carbonic acid catalyzed with carbonic anhydrase immobilized in polysulfone, free carbonic anhydrase, and no enzyme as described in example 1C wherein the experiment was performed in 0.5M $Na_2CO_3$, 50 sccm $CO_2$, at 4° C., and using 25 mg (0.5 mg/mL) carbonic anhydrase.

Sample 1C was prepared by dissolving 100 mg carbonic anhydrase in 10 mL 1-methylpyrrolidone with 0.05 mL Triton X-100 and adding 20 wt. % polysulfone in 1-methylpyrrolidone. Samples 1A and 1B are pictured in FIG. 11. Sample 1C was tested for enzymatic activity. FIG. 12 shows the comparison of carbonic anhydrase immobilized in polysulfone to blank solution and free enzyme in solution. The immobilized enzyme showed activity, but the activity was not a high as that of free enzyme. The experiment used beads of Sample 1C placed in 0.5 M sodium carbonate at 0° C. in a three ring flask with 50 sccm carbon dioxide sparged into the solution. The pH was monitored using a temperature adjusted pH meter over the course of approximately 50 minutes. Each run was started when the pH reached 11.0 in order to have an adequate pH verse time comparison.

Example 11

Carbonic Anhydrase Immobilized Polysulfone/Alginate Core-Shell Particulate Support Carbonic anhydrase was immobilized in alginate to form alginate beads by mixing 25 mg carbonic anhydrase with 2 mL of a 2 wt. % alginate solution. This solution was added dropwise into 50 mL of a 2 wt. % calcium chloride solution and stirred for at least 30 minutes. The beads having carbonic anhydrase immobilized in alginate were then removed and gently dried with paper towels. Next, the beads were rolled into a 20 wt. % polysulfone solution by hand to obtain a thin polysulfone film coating the alginate beads. Alginate beads dissolve in sodium carbonate solution without the polysulfone coating. But, the alginate does not dissolve and the carbonic anhydrase is retained when a thin film of polysulfone coats the bead. This process could also be used for other polymeric immobilization materials to advantageously control the substrate diffusion.

Figure 13:
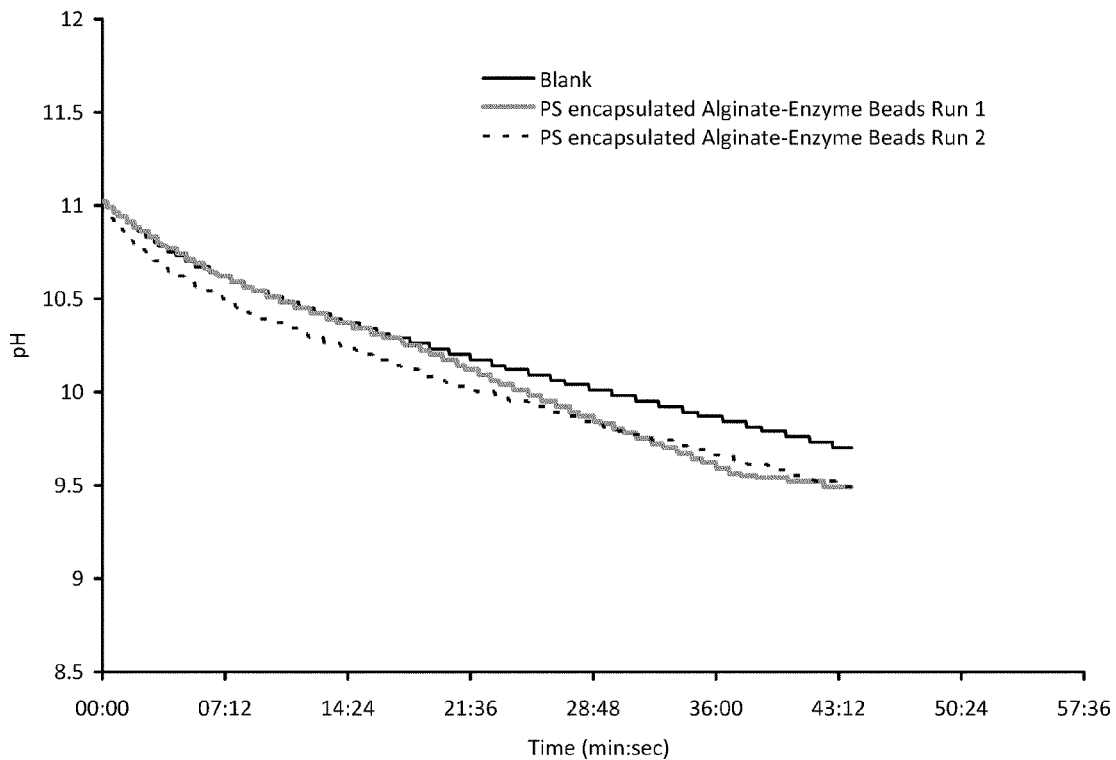
FIG. 13 is a graph of pH versus time for a reaction of carbon dioxide conversion to carbonic acid catalyzed with carbonic anhydrase immobilized in alginate and coated with polysulfone, free carbonic anhydrase, and no enzyme as described in example 2A wherein the experiment was performed in 0.5M $Na_2CO_3$, 50 sccm $CO_2$, at 4° C., and using 25 mg (0.5 mg/mL) carbonic anhydrase.

FIG. 13 shows the comparison of carbonic anhydrase immobilized in alginate encapsulated in polysulfone to blank solution. The immobilized enzyme did show activity throughout both runs. The first run was done almost immediately after the alginate beads were coated with polysulfone. The second run was soaked in a sodium carbonate/sodium bicarbonate solution overnight and then washed and tested in fresh solution. The resulting data suggested a diffusional limitation on the overall carbon dioxide reacted. As was seen in FIG. 13, the first run has a lower reaction rate than the blank for the first 20 minutes of the reaction, while the second run closely corresponds to the blank, but both runs containing enzyme end the experiment at the same pH value. The experiment consisted of 0.5 M sodium carbonate at 0° C. in a three ring flask with 50 sccm carbon dioxide sparged into the solution. The pH was monitored using a temperature adjusted pH meter over the course of approximately 50 minutes. Each run was started when the pH reached 11.0 in order to have an adequate pH verse time comparison.

Example 12

Carbonic Anhydrase Immobilized in Modified Polyvinyl Benzyl Chloride)

Figure 14:
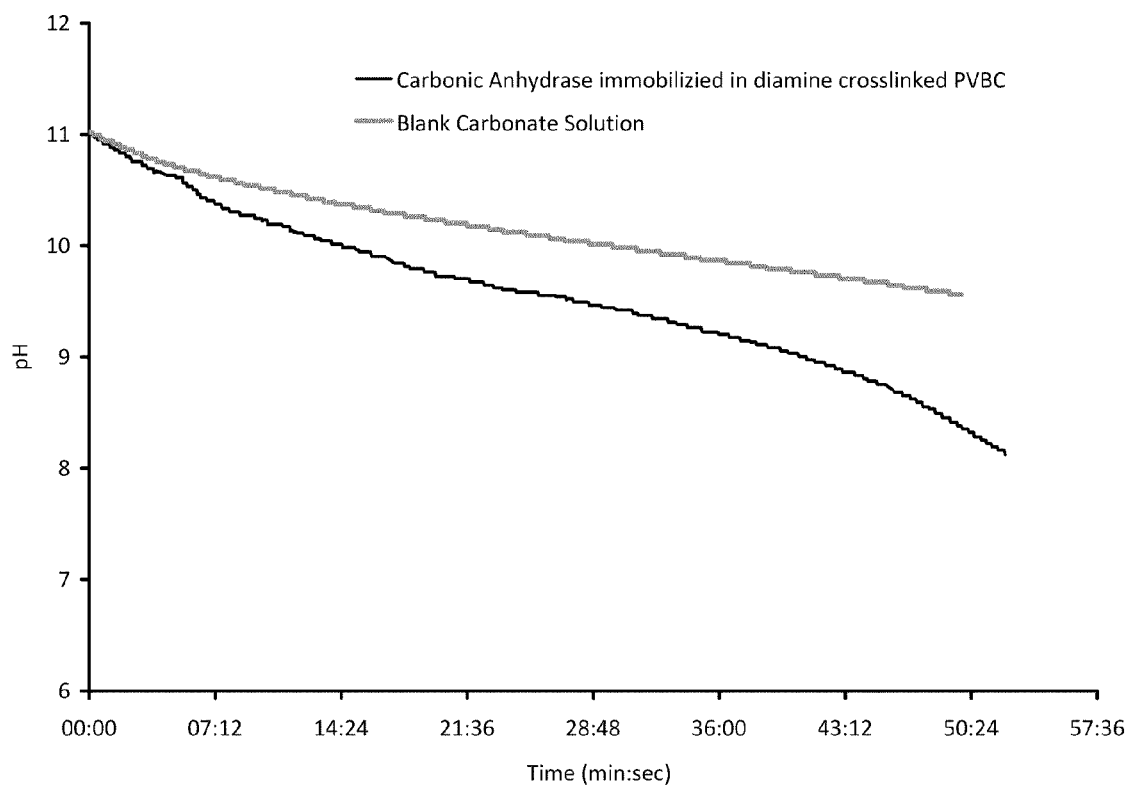
FIG. 14 is a graph of pH versus time for a reaction of carbon dioxide conversion to carbonic acid catalyzed with carbonic anhydrase immobilized in crosslinked poly(vinyl benzyl chloride) (PVBC) and no enzyme as described in example 3 wherein the experiment was performed in 0.5M $Na_2CO_3$, 50 sccm $CO_2$, at 4° C., and using 80 mg carbonic anhydrase.
Figure 15:
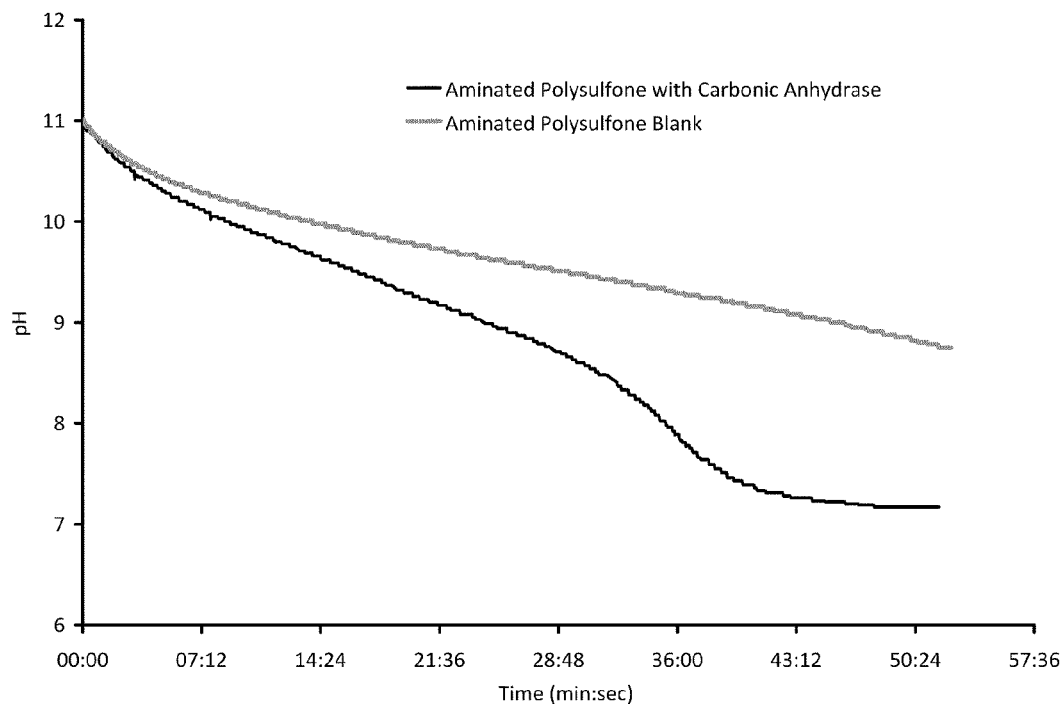
FIG. 15 is a graph of pH versus time for a reaction of carbon dioxide conversion to carbonic acid catalyzed with carbonic anhydrase immobilized in tetramethyl diamine aminated polysulfone particles and no enzyme as described in example 7 wherein the experiment was performed in 0.5M $Na_2CO_3$, 50 sccm $CO_2$, at 4° C., and using 50 mg carbonic anhydrase.

FIG. 14 shows the activity of this diamine cross-linked PVBC encapsulated carbonic anhydrase is approximately 50% that of the free enzyme in solution. The sample shown in FIG. 14 was taken after 2 hours of vigorous stirring in distilled, deionized water, demonstrated retention of enzyme within the support.

First, 5 mL of a 20 wt. % solution of poly(vinylbenzyl chloride) in dioxane was prepared. Then, 80 mg carbonic anhydrase was added to the solution and stirred until there was uniform dissolution. Once the solution was adequately dispersed, 0.435 mL N,N,N',N'-tetramethyl diaminomethane was added and stirred until the solution was sufficiently viscous to form a bead. However, the stirring was not long enough to allow the solution to gel. When the viscosity was low enough to be easily pipetted using a transfer pipette, the solution was added dropwise into a beaker of water and stirred to remove the excess solvent.

Example 13

Synthesis of Aminated Polysulfone

Polysulfone (10 g, PSf) and 40 mL of 1,2-dichloroethane were placed in a 3-neck 250 mL round bottom flask, and the solution was stirred with a Teflon stir bar to dissolve polysulfone. Once homogenized, 20 mL chloromethyl methyl ether and 2 g zinc chloride ($ZnCl_2$) were added to the flask. The flask was equipped with a thermometer, a condenser, and a rubber septum to cover the third opening. The reaction mixture was then heated to 40° C. with stirring and reacted for 4.5 hours. The solution was then cooled to room temperature and precipitated into 1.2 L of methanol. The crude chloromethylated polysulfone was collected and dried in the vacuum oven overnight at room temperature. This polymer was then redissolved in 200 mL 1,4-dioxane and reprecipitated into 1.2 L of methanol. The purified chloromethylated polysulfone (PSf-CH$_2$Cl) was then collected and dried in the vacuum oven overnight at room temperature. $^1$H NMR results indicated that 33% of the benzene rings in the polysulfone backbone were chloromethylated, corresponding to an average of 1.3 chloromethyl groups per repeat unit. A 20 wt. % solution of PSf-CH$_2$Cl in 1,4-dioxane was prepared by stirring with a Teflon stir bar in a glass vial.

Amination via trimethylamine. Beads of PSf-CH$_2$Cl were prepared by precipitating the 20 wt. % PSf-CH$_2$Cl in dioxane solution into a beaker with 500 mL deionized water. The beads were then stirred in the deionized water with a Teflon stir bar for 30 minutes. The beads were then collected and soaked in a solution of 0.04M trimethylamine in deionized water for 24 hours. They were then collected, rinsed with deionized water, and soaked in a 1M potassium hydroxide or potassium bicarbonate aqueous solution for 24 hours to exchange the chloride anions for either hydroxide or bicarbonate ions.

Amination via a tertiary diamine. A tertiary diamine (such as N,N,N',N'-tetramethyl-1,6-hexanediamine, TMHDA) was added to the 20 wt. % PSf-CH$_2$Cl in dioxane solution at an equimolar ratio of chloromethyl groups to tertiary nitrogens (equivalent to a 1:0.5 ratio of chloromethyl groups to diamine). For instance, 0.32 mL of TMHDA was added to 5 mL of a 20 wt. % solution of PSf-CH$_2$Cl described above (1.3 chloromethyl groups per repeat unit). The mixture was stirred for several minutes until noticeably more viscous. Beads were then prepared by precipitating this mixture into a beaker with 500 mL deionized water. The beads were then stirred in the deionized water with a Teflon stir bar for 30 minutes. They were then collected and soaked in a 1M potassium hydroxide or potassium bicarbonate aqueous solution for 24 hours to exchange the chloride anions for either hydroxide or bicarbonate ions.

Example 14

Synthesis of Aminated Polycarbonate

Polycarbonate (10 g, PC) and 80 mL of 1,2-dichloroethane were placed in a 3-neck 250 mL round bottom flask, and the solution was stirred with a Teflon stir bar to dissolve polycarbonate. Once homogenized, 20 mL chloromethyl methyl ether and 2 g zinc chloride (ZnCl$_2$) were added to the flask. The flask was equipped with a thermometer, a condenser, and a rubber septum to cover the third opening. The reaction mixture was then heated to 40° C. while stirring and reacted for 4.5 hours. The solution was then cooled to room temperature and precipitated into 1.2 L of methanol. The crude chloromethylated polycarbonate was collected and dried in the vacuum oven overnight at room temperature. This polymer was then redissolved in 200 mL 1,4-dioxane and reprecipitated into 1.2 L of methanol. The purified chloromethylated polycarbonate (PC—CH$_2$Cl) was then collected and dried in the vacuum oven overnight at room temperature. $^1$H NMR results indicated that only 5% of the benzene rings in the polycarbonate backbone were chloromethylated, corresponding to an average of 0.1 chloromethyl groups per repeat unit. A 20 wt. % solution of PC—CH$_2$Cl in N-methylpyrrolidone (NMP) was prepared by stirring with a Teflon stir bar in a glass vial.

Amination via trimethylamine. Beads of PC—CH$_2$Cl were prepared by precipitating the 20 wt. % PC—CH$_2$Cl in NMP solution into a beaker with 500 mL deionized water. The beads were then stirred in the deionized water with a Teflon stir bar for 30 minutes. The beads were then collected and soaked in a solution of 0.04M trimethylamine in deionized water for 24 hours. They were then collected, rinsed with deionized water, and soaked in a 1M potassium hydroxide or potassium bicarbonate aqueous solution for 24 hours to exchange the chloride anions for either hydroxide or bicarbonate ions.

Amination via a tertiary diamine. A tertiary diamine (such as N,N,N',N'-tetramethyl-1,6-hexanediamine, TMHDA) was added to the 20 wt % PC—CH$_2$Cl in NMP solution at an equimolar ratio of chloromethyl groups to tertiary nitrogens (equivalent to a 1:0.5 ratio of chloromethyl groups to diamine) For instance, 0.04 mL of TMHDA was added to 5 mL of a 20 wt. % solution of PC—CH$_2$Cl described above (0.1 chloromethyl groups per repeat unit). The mixture was stirred for several minutes until noticeably more viscous. Beads were then prepared by precipitating this mixture into a beaker with 500 mL deionized water. The beads were then stirred in the deionized water with a Teflon stir bar for 30 minutes. They were then collected and soaked in a 1M potassium hydroxide or potassium bicarbonate aqueous solution for 24 hours to exchange the chloride anions for either hydroxide or bicarbonate ions.

Example 15

Synthesis of Crosslinked Poly(vinylbenzyl chloride)

A 33 wt. % solution of poly(vinylbenzyl chloride) (PVBC) in dioxane was prepared by stirring with a Teflon stir bar in a glass vial. The choice of tertiary diamine or tertiary diamine mixture utilized to simultaneously aminate and crosslink PVBC affects the resulting chemical and mechanical properties of the beads and must be optimized for best performance. The use of two different diamine crosslinkers is described below.

Crosslinking with N,N,N',N'-tetramethyl-methanediamine (TMMDA). TMMDA (0.74 mL) was added to 5 mL of 33 wt. % PVBC dioxane solution (corresponding to an equimolar ratio of chloromethyl groups to nitrogens). The mixture was stirred for 3 minutes until noticeably more viscous. Beads were then prepared by precipitating this solution into a beaker with 500 mL deionized water. The beads were then stirred in the deionized water with a Teflon stir bar for 30 minutes. They were then collected and soaked in a 1M potassium hydroxide or potassium bicarbonate aqueous solution for 24 hours to exchange the chloride anions for either hydroxide or bicarbonate ions.

Crosslinking with N,N,N',N'-tetramethyl-phenylenediamine (TMPDA). TMPDA (0.89 g) was added to 5 mL of 33 wt. % PVBC dioxane solution (corresponding to an equimolar ratio of chloromethyl groups to nitrogens). The mixture was stirred for 1 hour until noticeably more viscous. The reaction of PVBC with TMPDA was much slower than its reaction with TMMDA, so these solutions were stirred longer before bead formation. Beads were then prepared by precipitating this solution into a beaker with 500 mL deionized water. The beads were then soaked in the deionized water for 30 minutes. These beads were not stirred in water after precipitation because these beads were hydrophilic, high-swelling materials that could break apart with strong agitation. They were then collected and soaked in a 1M potassium hydroxide or potassium bicarbonate aqueous solution for 24 hours to exchange the chloride anions for either hydroxide or bicarbonate ions.

Example 16

Carbonic Anhydrase Immobilized in Aminated Polysulfone

Figure 5:
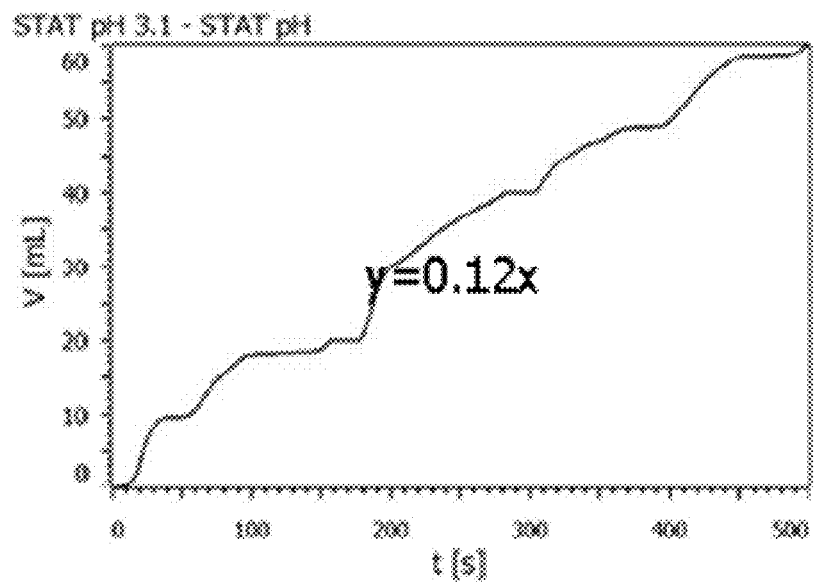
FIG. 5 is a graph of volume of 2M sodium hydroxide added to the reactor to keep the pH constant as the $CO_2$ is converted to bicarbonate versus time wherein there was no carbonic anhydrase in the reactor.

FIG. 5 shows the best retention of activity seen for aminated polymeric immobilization materials. The activity of this aminated polysulfone immobilized carbonic anhydrase is approximately 70% that of the free enzyme in solution. The sample shown in FIG. 5 was taken after 2 hours of vigorous stirring in DI water and demonstrated retention of enzyme within the immobilization material. To make the immobilized carbonic anhydrase particles, a solution of 5 ml of 20 wt. % chloromethylated polysulfone was made in dioxane. Then 50 mg carbonic anhydrase was added to the solution and stirred until a uniform dissolution occurred. Once the solution was adequately dispersed, tetramethyl diamine was added and stirred until the solution was sufficiently viscous to form a bead. However, the stirring was not long enough to allow the solution to gel. When the viscosity was low enough to be easily pipetted using a transfer pipette, the solution was added dropwise into a beaker of water and stirred to remove excess solvent.

Example 17

Hydration of $CO_2$ in Amine Solutions Using Carbonic Anhydrase

An aqueous solution containing water, an amine, and in some cases an enzyme had carbon dioxide bubbled through it and the amount of carbon dioxide that was captured was measured by determining the amount of sodium hydroxide added to the solution in order to maintain a pH value of 11 (the pH of the amine solutions). However, one MDEA test was performed at pH 8.4 (pH adjusted by sparging solution with carbon dioxide). Carbon dioxide was introduced into the aqueous solution at a rate of 200 sccm through a spherical sparging stone.

The immobilization material used for the was a polysulfone (PSf) backbone with polyethyleneoxide (PEO; average molecular weight of 550) grafted to a degree of functionality of 0.5 which corresponds to approximately 38% wt. (PEGylated PSf). The carbonic anhydrase (bovine CA) was immobilized in PEGylated PSf spheres using the following process. The enzyme was dissolved into the solvent with a surfactant. To encapsulate carbonic anhydrase in a polysulfone, the solvent was selected to not deactivate the enzyme. The polymer was added to the solution and stirred until completely dissolved. The polymer enzyme solution was held at room temperature until completely mixed. The dissolved polymer enzyme solution was then added dropwise to water, alcohol, or a water-alcohol solution creating polymeric beads. The enzyme used was a commercially available mammalian CA from a bovine source.

The primary amine used for these studies was monoethanolamine (MEA) that was tested at concentrations of 12 and 144 mM in DI water with an enzyme solution loading for the enzyme free in solution of 0.25 mg/mL in both amine concentrations and 0.5 mg/mL in the 144 mM MEA solution and an immobilized enzyme loading of 0.25 mg/mL solution. The tertiary alcohol amine that was examined is N-methyldiethanolamine (MDEA) and was tested at concentrations of 12 and 144 mM in DI water with an enzyme solution loading of 0.25 mg/mL in both amine concentrations. A second non-alcohol tertiary amine was included in this study, N,N-diethylmethylamine (DMA), and was tested at concentrations of 71 and 144 mM in DI water with an enzyme solution loading of 0.25 mg/mL in both amine concentrations. All of the solutions were kept at room temperature and the total volumes were set at 50 mL.

Figure 16:
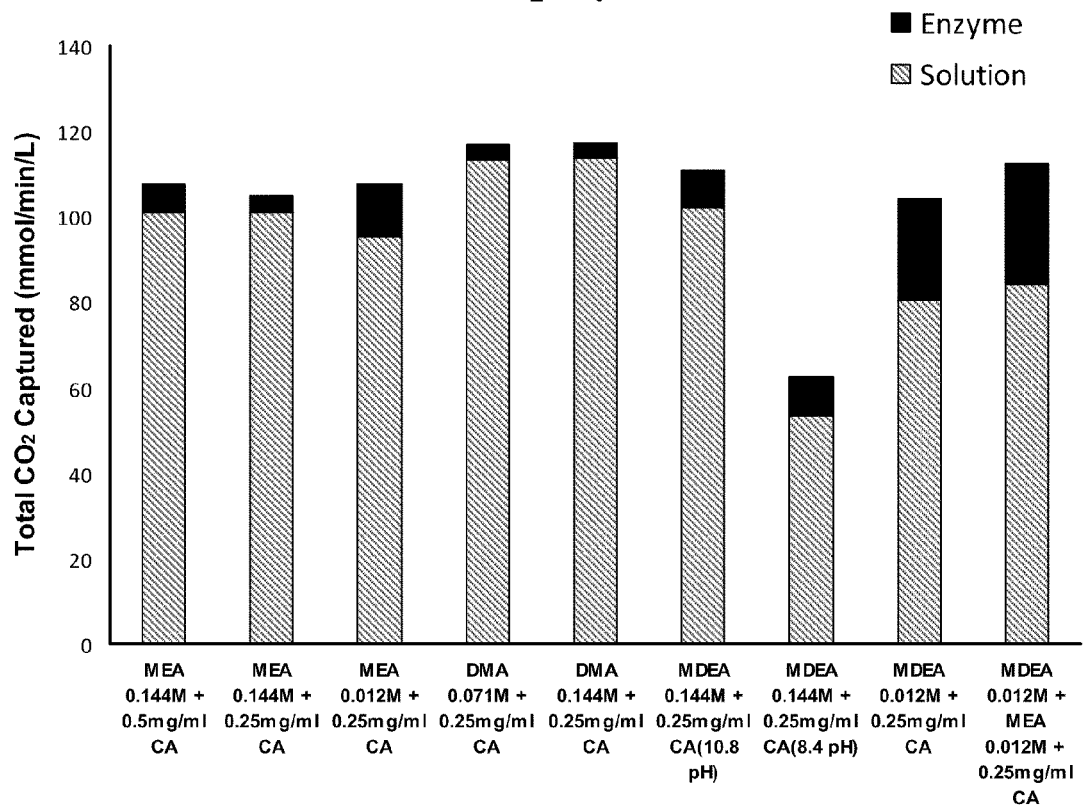
FIG. 16 is a graph of the total $CO_2$ captured in terms of mmol/min/L for carbonic anhydrase enzymes (CA) in solutions of monoethanolamine (MEA), N,N-diethylmethylamine (DMA), and N-methyldiethanolamine (MDEA).

The enzyme contribution was separated from the amine contribution through the comparisons of amine solutions to amine plus enzyme solutions. The results of this study, in terms of total carbon dioxide captured for both the amine and enzyme component, are shown in FIG. 16. The total amount of carbon dioxide captured with both enzyme and amine was relatively the same for all systems at pH 11. The enzyme had the greatest contribution of approximately 25% in the 12 mM MDEA and 12 mM MDEA/12 mM MEA solutions. The enzymes had the least contribution to total carbon dioxide capture in the DMA solutions, but the overall carbon dioxide capture in these solutions was the largest of all the systems tested and at the concentrations tested, seemed to be independent of amine concentration.

Figure 17:
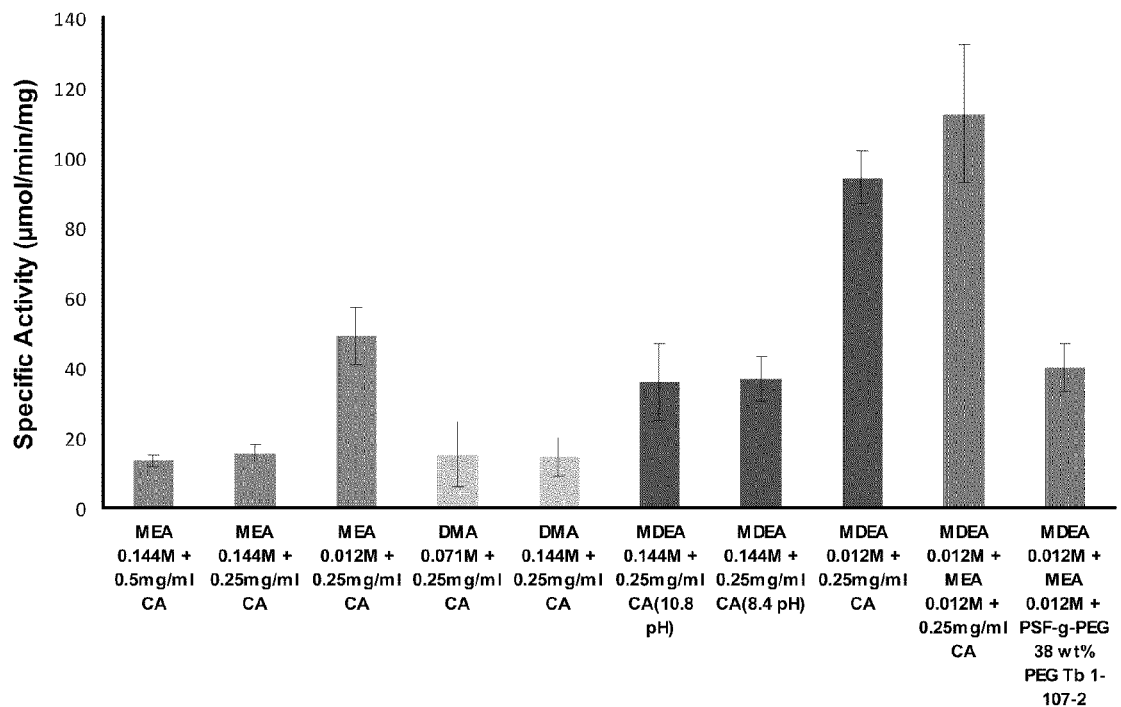
FIG. 17 is a graph of the specific activities of carbonic anhydrase in terms of μmol/min/mg for solutions of MEA, DMA, and MDEA.

The specific activities of enzyme in all of the above listed conditions are shown in FIG. 17. The largest activity of the enzyme system was observed in the mixed MEA and MDEA solution followed by the low concentration MDEA solution. The enzyme had the highest specific activity in the low concentration alcohol amine solutions when compared to the higher concentrations of the same amine. It is unclear whether these enzyme activities are the result of substrate inhibition by the amine or because the amine base is competitive in absorbing the carbon dioxide at higher concentrations.

Example 18

Removal of Carbon Dioxide from Solution Using Carbonic Anhydrase

Carbonic anhydrase was used for removing carbon dioxide from the aqueous liquid described in example 17. The experimental design and conditions of this study were similar to Example 17, but the substrate for the carbonic anhydrase was the absorbed carbon dioxide and the immobilized enzyme mixture was cast onto a high surface area support, crushed lava rock (about 1 cm in diameter), and allowed to dry into a film.

Figure 18:
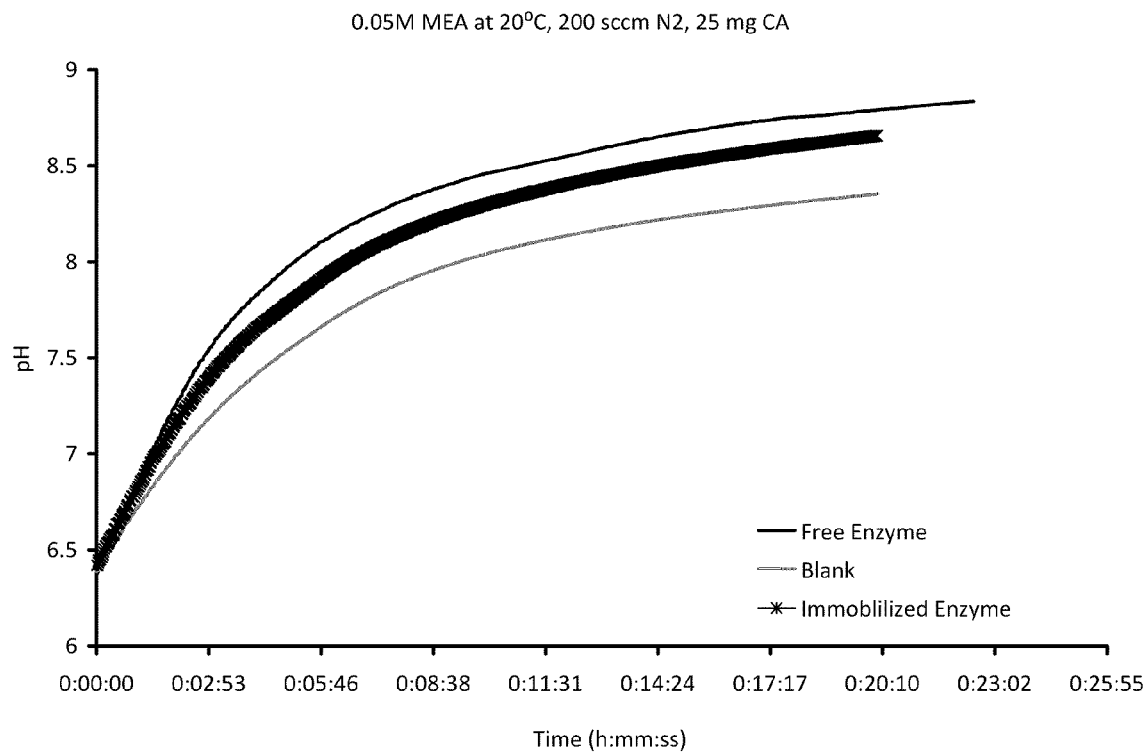
FIG. 18 is a graph of pH versus time for a reaction of carbonic acid to carbon dioxide catalyzed with carbonic anhydrase immobilized in PEGylated polysulfone, free carbonic anhydrase, and no enzyme wherein the experiment was performed in 0.5M MEA, 200 sccm $N_2$, at 20° C., and using 25 mg (0.5 mg/mL) carbonic anhydrase.
Figure 19:
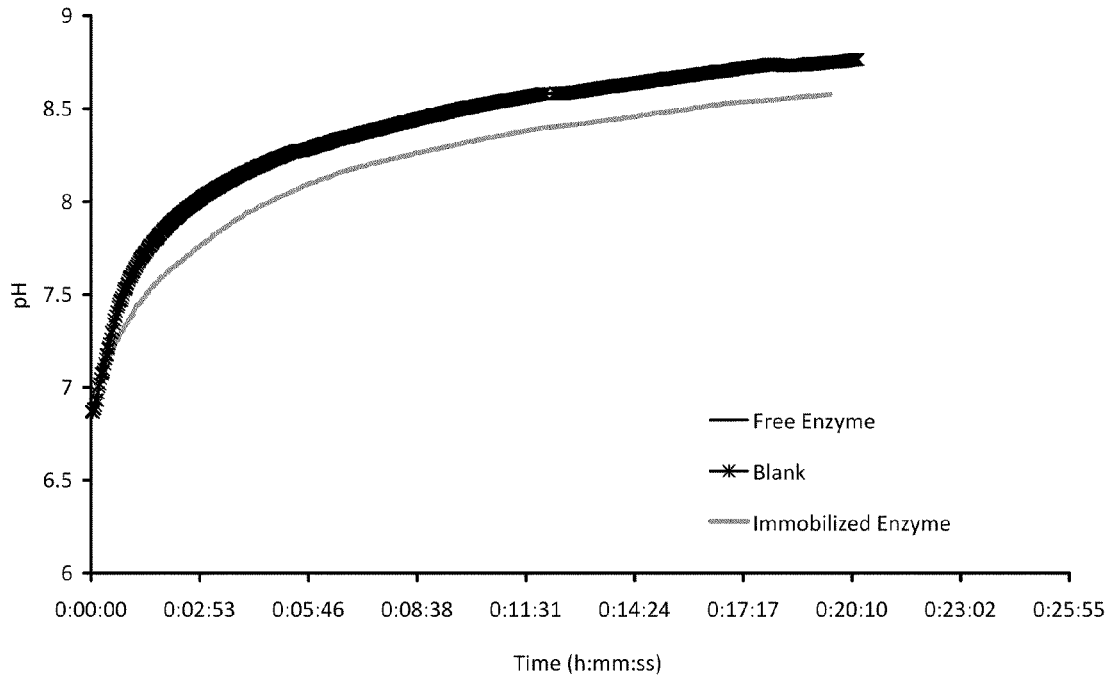
FIG. 19 is a graph of pH versus time for a reaction of carbonic acid to carbon dioxide catalyzed with carbonic anhydrase immobilized in PEGylated polysulfone, free carbonic anhydrase, and no enzyme wherein the experiment was performed in 0.5M MEA, 200 sccm $N_2$, at 50° C., and using 25 mg (0.5 mg/mL) carbonic anhydrase.

The reaction of carbon dioxide in an amine solution can produce carbamates, carbonate, bicarbonate, or mixtures depending on the reaction temperature, the nature of the amine (i.e., primary, secondary, or tertiary amine), the carbon dioxide partial pressure, and the reaction pH. It was determined that generating the substrate by introducing carbon dioxide gas into the system for a fixed amount of time to produce the substrate and then monitoring the change in solution pH to follow the release of carbon dioxide was an efficient way to conduct the experiment. The concentration of the amine, MEA and MDEA, was 0.05 M, the reaction was tested at room temperature and at 50° C., and the enzyme mass was 25 mg. The products for the reverse reaction were generated by introducing carbon dioxide through a glass frit sparger into the amine solution, with and without enzyme, at a rate of 200 sccm for 10 minutes. The pH of this reaction was monitored to verify that the conversion of the amine was complete and that the starting pH of the reverse reaction and the temperature was the same for each sample (e.g., blank amine solution, amine solution with non-immobilized enzyme, and amine solution with immobilized enzyme). After the carbon dioxide exposure, nitrogen gas was introduced into the solution via a glass frit sparger at a rate of 200 sccm for 20 minutes while the solution pH was monitored and recorded. The relative activity of the enzyme in each case was determined by the rate of the pH increase from the starting point to the final pH of the solution after 20 minutes. The faster the pH increased and the greater the final pH, the higher the relative activity of the enzyme. The results of the MEA solution at 20° C. and 50° C. are shown in FIGS. 18 and 19, respectively. At 20° C., both the free enzyme in solution and the immobilized enzyme had higher conversions of carbon dioxide release than the comparable solution with no enzyme. The immobilized enzyme had a lower activity than the free enzyme probably due to mass transfer effects from the immobilization material. At 50° C., there was no difference between the free enzyme and the blank solution and a reduced performance of the immobilized enzyme was observed.

Figure 20:
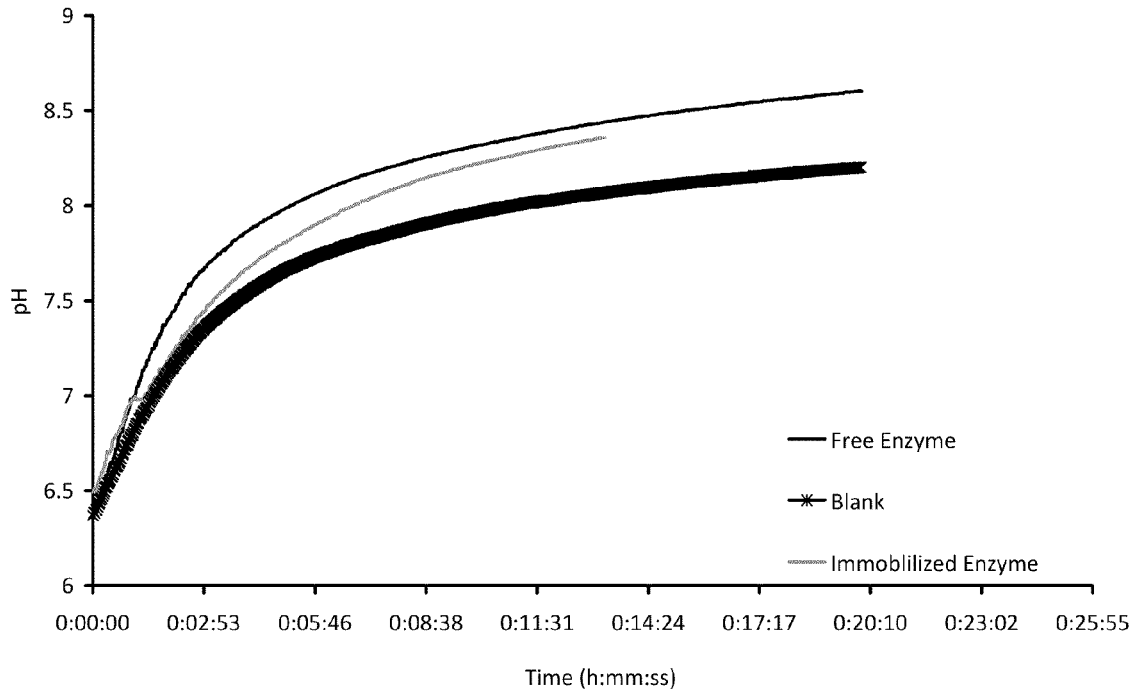
FIG. 20 is a graph of pH versus time for a reaction of carbonic acid to carbon dioxide catalyzed with carbonic anhydrase immobilized in PEGylated polysulfone, free carbonic anhydrase, and no enzyme wherein the experiment was performed in 0.5M MDEA, 200 sccm $N_2$, at 20° C., and using 25 mg (0.5 mg/mL) carbonic anhydrase.
Figure 21:
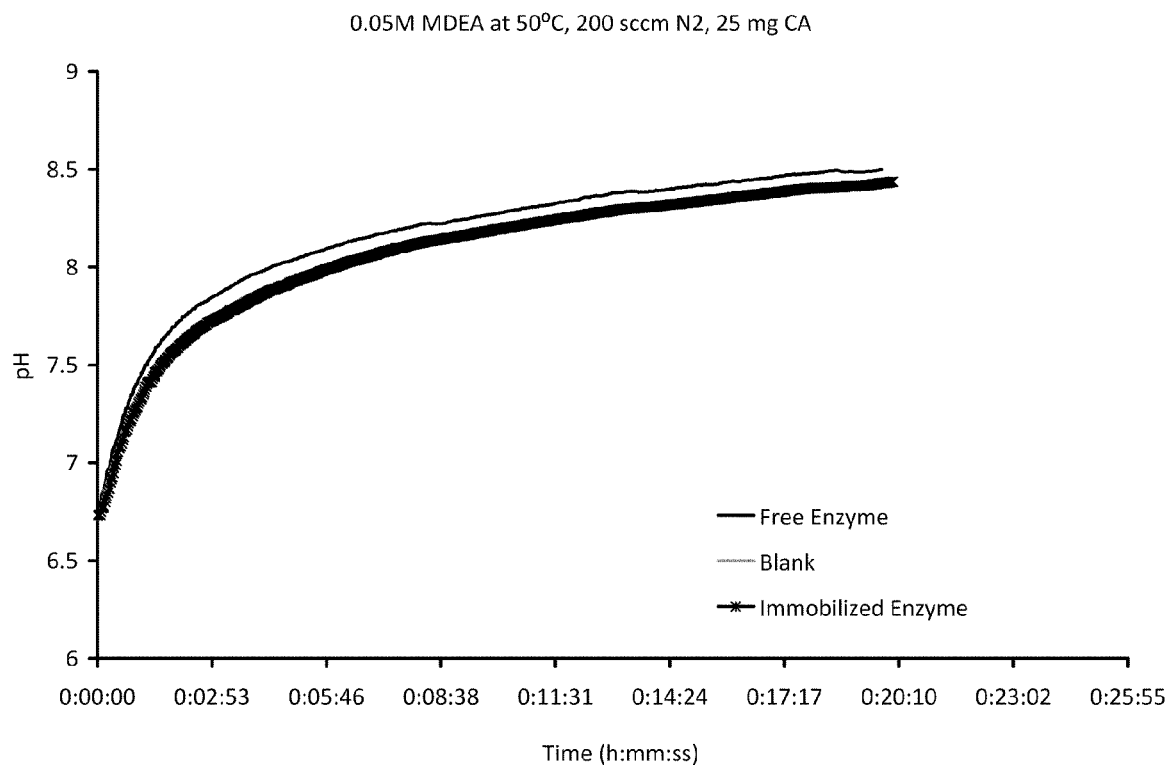
FIG. 21 is a graph of pH versus time for a reaction of carbonic acid to carbon dioxide catalyzed with carbonic anhydrase immobilized in PEGylated polysulfone, free carbonic anhydrase, and no enzyme wherein the experiment was performed in 0.5M MDEA, 50 sccm $N_2$, at 50° C., and using 25 mg (0.5 mg/mL) carbonic anhydrase.

The results of the MDEA solution at 20° C. and 50° C. are respectively shown in FIGS. 20 and 21. At 20° C., both the free enzyme in solution and the immobilized enzyme had higher conversions of carbon dioxide release than the comparable solution with no enzyme. The rate of change in solution pH was less for the immobilized enzyme compared to the free enzyme in solution at the beginning of the experiment but near the end of the experiment the pH of both systems was nearly the same in the MDEA solution. There was no difference between the free enzyme in the MDEA solution and the blank MDEA solution and a lower amount of carbon dioxide was released in the sample with the immobilized enzyme.

Under the reaction conditions, the reaction of a primary amine with carbon dioxide produces a carbamate; it is thought that carbonic anhydrase cannot use carbamate as a substrate. Thus, the improved performance of the enzymatic system at lower temperatures and not at higher temperatures for this system may be attributed to the initial enzymatic hydration and dehydration of the carbon dioxide in the alkaline solution for both the forward and reverse reactions. This reaction appears to dominate the amine reaction at lower temperatures and the amine reaction becomes dominant as the temperature is increased.

Example 19

Thermal Stability of Carbonic Anhydrase

Figure 22:
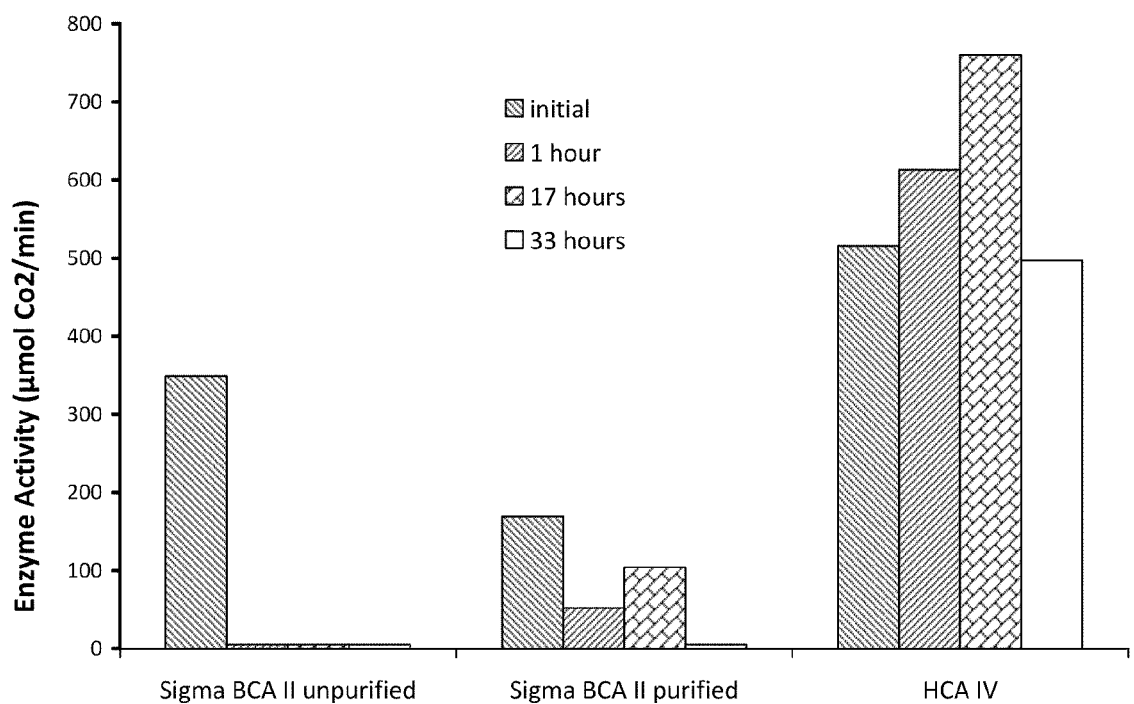
FIG. 22 is a graph of the enzyme activity of free carbonic anhydrase (CA) in solution (0.1 mg/mL) assayed at room temperature after exposure to 70° C. for the specified time.

The thermal stability of several carbonic anhydrases was studied by measuring the carbon dioxide activity. The thermal stabilities of bovine carbonic anhydrase II (BCA II, (purified and unpurified) and human carbonic anhydrase IV (HCA IV) were determined by incubating 0.2 mg/mL solutions in deionized (DI) water (25 mL total) for the allotted time in the oven at 70° C. and then diluting them with equal volume of 0.4M $NaHCO_3$ to perform the pH stat analysis of carbon dioxide activity. It was determined that it takes 1.5 hours for 25 mL of DI water to reach 70° C. in the oven, so the total time the samples were in the oven was adjusted to account for the long lag time in reaching the temperature set point. These results are summarized in FIG. 22. As seen in this figure, HCA IV exhibited a higher thermal stability by retaining nearly 100% of its initial activity after 32 hours of exposure at 70° C. In contrast, BCA II (unpurified) lost all of its activity after only 1 hour at 70° C. Purification of BCA II did improve its thermal stability, but purified BCA II still had lower thermal stability than HCA IV.

Additional measurements of the thermal stability of HCA IV were limited by the aggregation of the enzyme seen after 32 hours of exposure to 70° C. The HCA IV appeared to irreversibly aggregate into large chunks of enzyme that were still active by the carbon dioxide activity test via the pH stat.

Example 20

Synthesis of Polysulfone Grafted with Polyethylene Glycol (PSf-g-PEG) Immobilization Material Chloromethylation of Polysulfone. Polysulfone (PSf; 20 g) and 200 mL of 1,2-dichloroethane were placed in a 2-neck 500 mL round bottom flask and the solution was stirred with a Teflon stir bar to dissolve PSf. Once homogenized, 15 mL of chloromethyl methyl ether and 1.5 g of zinc(II) chloride ($ZnCl_2$) were added to the flask. The flask was equipped with a thermometer and a condenser. The reaction mixture was then heated to 40° C. while stirring and reacted for a set period of time. The reaction time determined the chloromethylation degree of PSf. For instance, a reaction time of 2.5 hours resulted in a degree of functionalization (DF) of 0.55, meaning an average of 0.55 chloromethyl groups per PSf repeat unit. Similarly, reaction times of 2.25 hours, 2 hours, and 1.25 hours resulted in DFs of 0.5, 0.4, and 0.23, respectively. After the allotted reaction time, the reaction mixture was cooled to room temperature, diluted with 200 mL of 1,2-dichloroethane, and precipitated into 4.5 L of methanol. The chloromethylated polysulfone (PSf-$CH_2$Cl) was collected via filtration and dried in the vacuum oven overnight at room temperature.

Poly(ethylene glycol) Grafting onto Chloromethylated Polysulfone. Once dry, chloromethylated polysulfone (PSf-$CH_2$Cl; 10 g) and 250 mL of dry 1,4-dioxane (dried over molecular sieves) were added to a 500 mL round bottom flask, and the solution was stirred with a Teflon stir bar to dissolve PSf-$CH_2$Cl. Once homogenized, this flask was capped with a rubber septum and flushed with nitrogen for 15 minutes. To a separate 50 mL round bottom flask, a 1.5 molar excess (with respect to the chloromethyl groups of PSf-$CH_2$Cl) of poly(ethylene glycol) monomethyl ether (PEG) with a molecular weight of 550 Da was added. Sufficient dry 1,4-dioxane was added to this flask to make a 25 vol. % PEG solution. For example, for PSf-$CH_2$Cl with a DF of 0.55, 10.3 mL of PEG and 31 mL of 1,4-dioxane were added. This flask was then capped with a rubber septum and flushed with nitrogen for 10 minutes. To a separate 100 mL round bottom flask, a 1.5 molar excess (with respect to the chloromethyl groups of PSf-$CH_2$Cl) of sodium hydride (NaH) was added. Sufficient dry 1,4-dioxane was added to this flask to make a 1 wt./vol. % NaH solution. For example, for PSf-$CH_2$Cl with a DF of 0.55, 0.44 g of NaH and 44 mL of 1,4-dioxane were added. This flask was then equipped with a Teflon stir bar, capped with a rubber septum, and flushed with nitrogen for 10 minutes. The PEG solution was then added dropwise via a cannula to the NaH solution while stirring. This reaction mixture was then stirred for 3 hours at room temperature while venting periodically with a needle to release generated hydrogen gas. After 3 hours, the PEG/NaH solution was added dropwise via a cannula with stirring to the PSf-$CH_2$Cl solution. This reaction mixture was then stirred for 2 days at room temperature. After the reaction was complete, the reaction mixture was neutralized to pH 7 using concentrated acetic acid and then precipitated into 4.5 L of deionized water. Polysulfone grafted with PEG (PSf-g-PEG) was then collected via filtration, rinsed with excess deionized water, and dried in the vacuum oven at 40° C. overnight. The DF of PSf-g-$CH_2$Cl determined the final weight percent of PEG in PSf-g-PEG. For instance, PSf-g-$CH_2$Cl with a DF of 0.55 resulted in PSf-g-PEG with 40 wt % PEG. Similarly, DFs of 0.5, 0.4, and 0.23 resulted in PEG loadings of 38 wt. %, 33 wt. %, and 22 wt. %, respectively.

Example 21

Immobilization of Carbonic Anhydrase Using Polysulfone-Graft-poly(ethylene glycol)

Solvent Evaporation Method. Dry polysulfone-graft-poly(ethylene glycol) (PSf-g-PEG; 0.25 g) and 3.5 mL of dichloromethane were added to a capped glass vial, and the solution was stirred with a Teflon stir bar to dissolve PSf-g-PEG. To a 50 mL beaker, about 6 g of porous support material and 25 mg of BCA II (Sigma Aldrich; unpurified) or 10 mg of HCA IV (St. Louis University) were added. Once homogenized, the PSf-g-PEG solution was added to the beaker and stirred to coat the porous support material. The contents of the beaker were stirred continuously until all of the solvent had evaporated. The coated porous support material was then transferred to the vacuum oven at room temperature for 15 minutes to evaporate any residual dichloromethane before transferring to 0.2M $NaHCO_3$ for storage.

Solvent Exchange Method. Dry polysulfone-graft-poly(ethylene glycol) (PSf-g-PEG; 0.33 g) and 1.5 mL of N-methylpyrrolidone (or a comparable water-miscible solvent that also dissolves this polymer such as 1,4-dioxane) were added to a capped glass vial, and the solution was stirred with a Teflon stir bar to dissolve PSf-g-PEG. Once homogenized, 25 mg of BCA II (Sigma Aldrich; unpurified) or 10 mg of HCA IV (St. Louis University) was added and mixed thoroughly. The solution was then added to 250 mL of deionized water dropwise via a transfer pipette to form polymer beads. After 1 hour, the beads were transferred to 0.2M $NaHCO_3$ for storage.

Example 22

Immobilized BCA II

Figure 23:
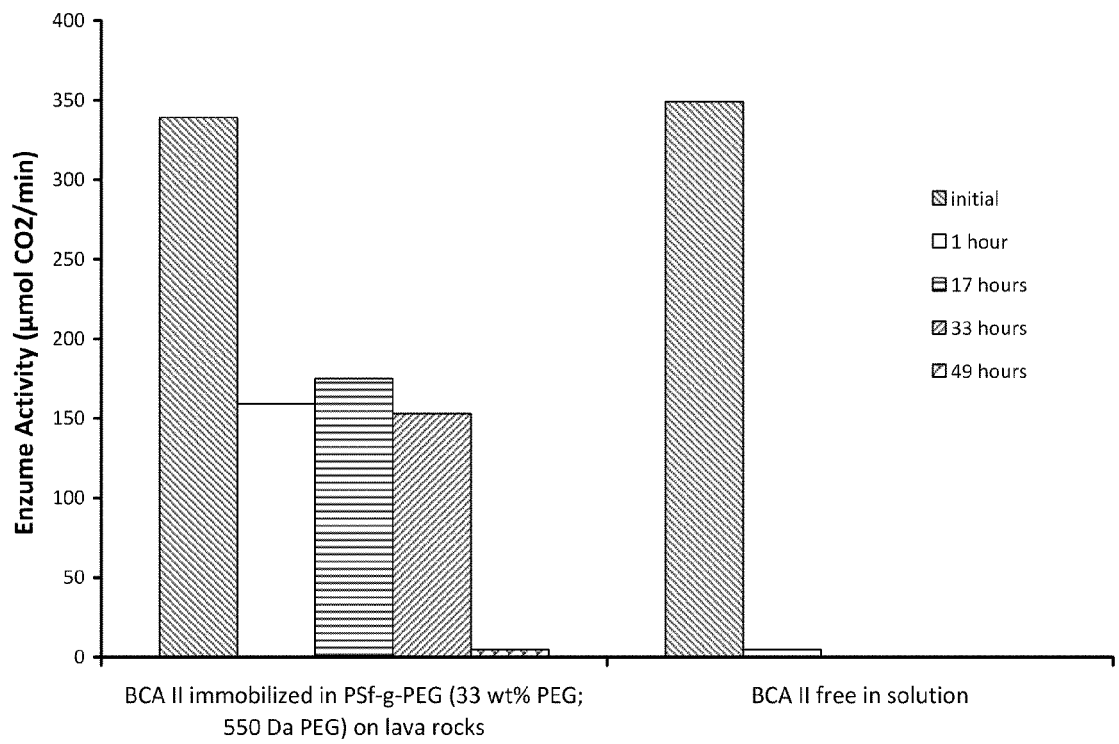
FIG. 23 is a graph of the enzyme activity at 70° C. for free and immobilized unpurified bovine carbonic anhydrase II (BCA II) for the specified time.

Unpurified BCA II immobilized in PSf-g-PEG (33 wt % PEG; 550 Da PEG) maintained about 50% of its initial activity after 33 hours (2 nights) at 70° C. A third night (16 additional hours) at 70° C. resulted in a loss of the remaining activity. In contrast, unpurified BCA II free in solution lost its activity after one hour at 70° C. The thermal stability of this immobilized sample compared to free enzyme is summarized in FIG. 23.

Figure 24:
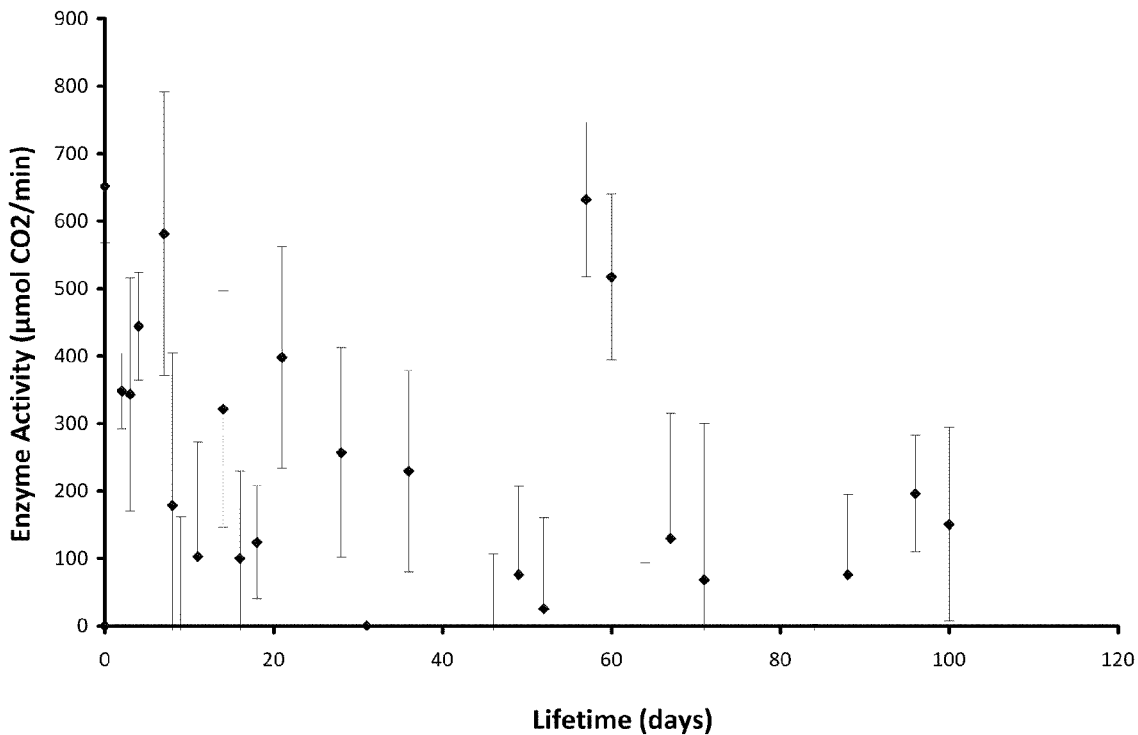
FIG. 24 is a graph of the enzyme activity versus time for unpurified BCA II immobilized in polysulfone grafted with polyethylene glycol (PSf-g-PEG, 22 wt % PEG; 550 Da PEG) on lava rocks tested via a pH stat.
Figure 25:
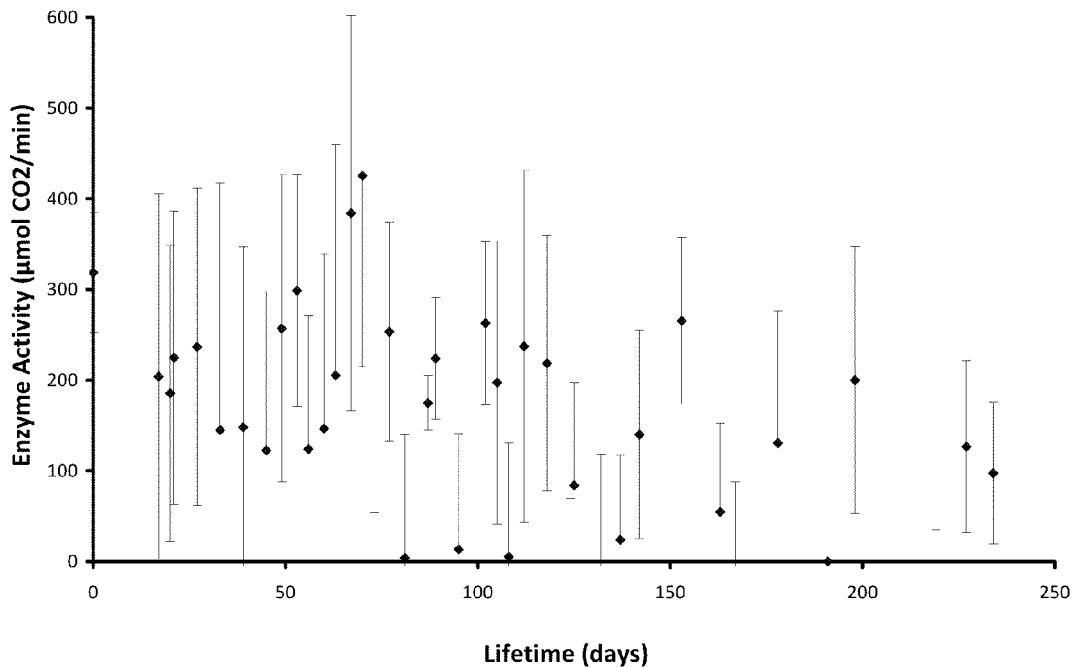
FIG. 25 is a graph of the enzyme activity versus time for unpurified BCA II immobilized in PSf-g-PEG (38 wt % PEG; 550 Da PEG) on lava rocks tested via a pH stat.

The longest lifetime study to date is with unpurified BCA II immobilized in PSf-g-PEG (22 wt % PEG; 550 Da PEG) on lava rocks, shown in FIG. 24, and unpurified BCA II immobilized in PSf-g-PEG (38 wt % PEG; 550 Da PEG) on lava rocks, shown in FIG. 25. These immobilized samples still demonstrate activity after 60 days and 56 days, respectively. The lifetime of unpurified BCA II free in solution has not been determined.

Example 23

Immobilized HCA IV

Figure 26:
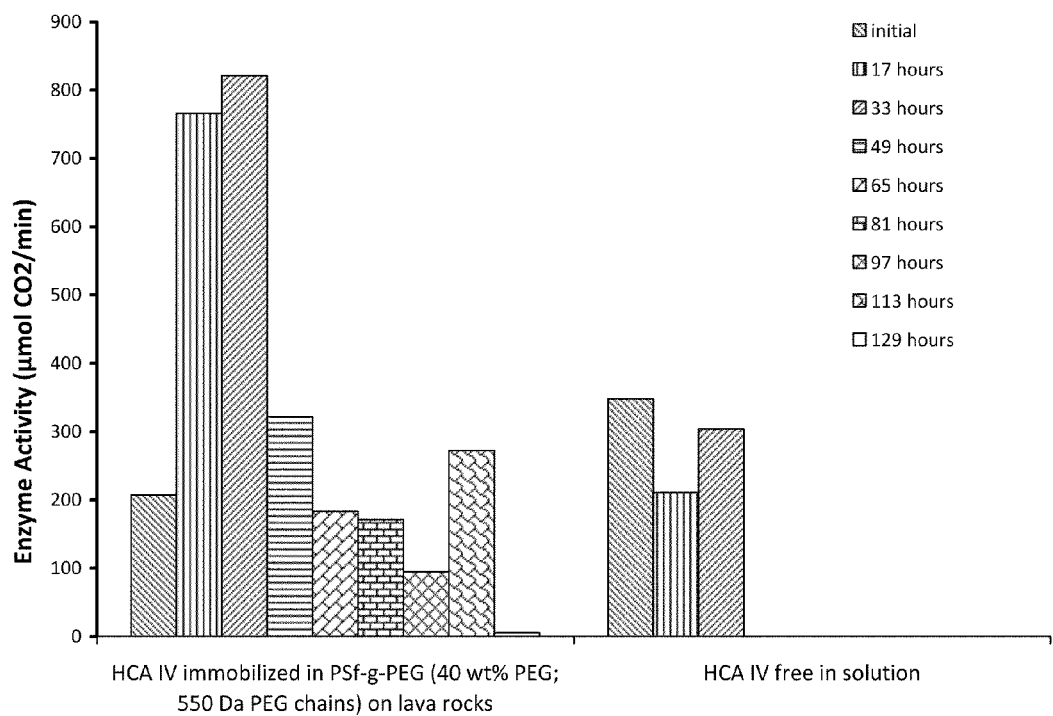
FIG. 26 is a graph of the enzyme activity at 70° C. of free and immobilized human carbonic anhydrase IV (HCA IV) for the specified time.
Figure 27:
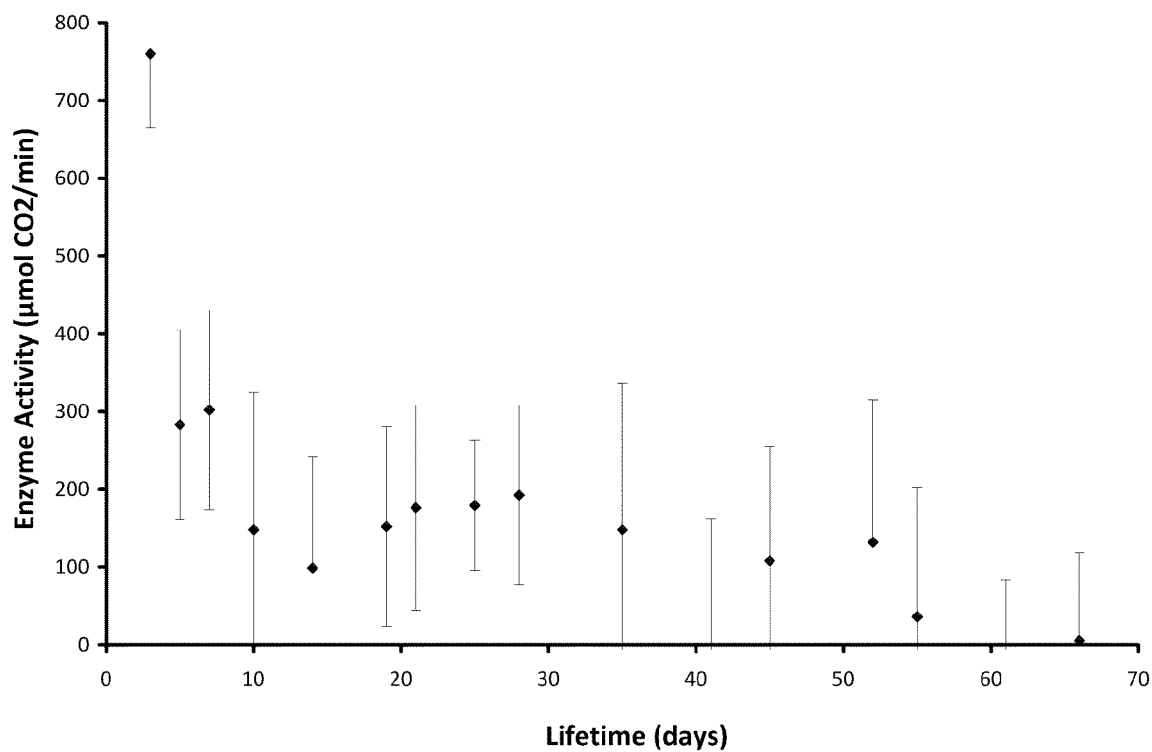
FIG. 27 is a graph of the enzyme activity versus time for HCA IV immobilized in PSf-g-PEG (40 wt % PEG; 550 Da PEG) on lava rocks.

PSf-g-PEG was also used to immobilize HCA IV. The greatest thermal stability was found for HCA IV immobilized in PSf-g-PEG (40 wt % PEG; 550 Da PEG) where about 100% of its initial activity was maintained after 113 hours (7 nights) at 70° C. An eighth night (16 additional hours) at 70° C., however, resulted in a loss of the remaining activity. The thermal stability of this immobilized sample was compared to free enzyme and is summarized in FIG. 26. As mentioned previously, the determination of the thermal stability of free HCA IV in solution was limited by the formation of large aggregates after extended heating times. Lifetime studies continue for HCA IV immobilized in PSf-g-PEG samples. For instance, HCA IV immobilized in PSf-g-PEG (40 wt % PEG; 550 Da PEG) demonstrated significant activity after 22 days, as seen in FIG. 27.

Example 24

Poly(ethylene glycol) Grafting onto Poly(methyl hydrosiloxane)

Poly(methyl hydrosiloxane) (PMHS, $MW_{avg}$=2250 g/mol; 30 mL) and allyloxy(polyethylene glycol) monomethyl ether (PEG, $MW_{avg}$=500 g/mol; 27 mL) were added to a 500 mL 2-neck round bottom flask equipped with teflon magnetic stir bar. Dry toluene (150 mL, dried over molecular sieves) was then added with stirring to homogenize the solution. The flask was equipped with a condenser and thermostat and placed in a heating jacket. The flask and condenser was purged with nitrogen while heating to 80° C. with stirring. Then 0.8 mL of 1 mM chloroplatinic acid ($H_2PtCl_6$) solution in 2-propanol was injected via a gas-tight syringe. After an additional 5 minutes of nitrogen purging, the purging and venting needles were removed. The reaction mixture was slowly heated to 108° C. while stirring and periodically venting the reaction mixture to relieve pressure buildup. The reaction proceeded at 108° C. under nitrogen with stirring for 3 days. The reaction was stopped by cooling to room temperature and then stirring over activated charcoal to remove platinum catalyst. After 30 minutes, the charcoal was removed via filtration. About 55 mL of PMHS grafted with PEG (PMHS-g-PEG) was collected by removing the toluene under reduced pressure. The average PEG grafting density of this polymer was determined to be 4.8 by $^1H$ NMR, meaning that it has an average of 4.8 PEG chains per PMHS chain. This grafting density corresponds to a PEG loading of about 52 wt. %. The PEG loading in the PMHS-g-PEG polymers was adjusted by varying the amounts of PEG relative to PMHS used during the reaction. Additional toluene may be required to homogenize the reaction mixture.

Example 25

Immobilization of CA Using poly(methyl hydrosiloxane)-graft-poly(ethylene glycol)

Poly(methyl hydrosiloxane)-graft-poly(ethylene glycol) (1 mL; PMHS-g-PEG; ~52 wt. % PEG), 1 mL of disilanol terminated poly(dimethylsiloxane) ($PDMS-(OH)_2$, $MW_{avg}$=4200 g/mol), and 0.15 mL of silanol-trimethylsilyl modified Q resin (50 wt. % solution in decamethylcyclopentasiloxane solvent) were mixed together in a glass vial. To this mixture, 50 mg of BCA II (Sigma Aldrich; unpurified) or 30 mg HCA IV (St. Louis University) was added and thoroughly mixed. Dibutyldilauryltin catalyst (70 µL) for crosslinking via a dehydrogenative coupling mechanism was then mixed in. The solution was transferred to an acrylic mold of cylinders (¼ inch deep and ⅛ inch in diameter) via a transfer pipette. The mold was placed in the refrigerator at 4° C. for several hours to allow the mixture to cross-link. Once solidified, the polymer pellets (overall ~25 wt. % PEG) were removed from the mold and stirred in deionized water to equilibrate. The PEG content of the enzyme-containing polysiloxane pieces can be varied by using a PMHS-g-PEG polymer with a different PEG wt. %. As the PEG content increased, some PMHS or hydride Q resin was added to improve the cross-link density (10-50 vol. % of the PMHSg-PEG used). The amount of silanol-trimethylsilyl modified Q resin can also be adjusted to change the cross-link density, ranging from 10-50 vol. % of the PMHS-g-PEG used.

A lifetime study was performed of unpurified BCA II immobilized in PMHS-g-PEG (50 wt. % PEG) that was crosslinked using a tin catalyst and disilanol-terminated PDMS ($MW_{avg}$=2750 g/mol). The amount of PDMS added was such that the overall PEG content in the immobilization matrix was 20 wt. %. A 5-day simple moving average of the % remaining activity in the sample showed the average remaining activity holding fairly steady around 60% through day 82 of its lifetime.

A study of the thermal stability of unpurified BCA II immobilized in PMHS-g-PEG (50 wt. % PEG) that was crosslinked using a tin catalyst and di-silanol PDMS ($MW_{avg}$=2750 g/mol) was performed. The amount of PDMS added was such that the overall PEG content in the immobilization matrix was 20 wt. %. The enzyme maintained about 80% of its activity after 32 hours at 70° C., whereas BCA II free in solution lost all activity after only 1 hour at 70° C.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions and uses without departing from the scope of the invention, it is intended that all matter contained in the above description and shown in the accompanying drawings shall be interpreted as illustrative and not in a limiting sense.

The invention claimed is:

1. A process for removing $CO_2$ from a $CO_2$-containing gas, the process comprising
contacting an aqueous liquid with a $CO_2$-containing gas to promote diffusion of the $CO_2$ into the aqueous liquid; and contacting the $CO_2$ in the aqueous liquid with immobilized carbonic anhydrase entrapped in a polymeric immobilization material to catalyze hydration of the $CO_2$ and form a treated liquid containing hydrogen ions and bicarbonate ions; wherein the polymeric immobilization material comprises a micellar or inverted micellar material.

2. The process of claim 1 wherein the aqueous liquid and $CO_2$-containing gas are contacted in a co-current configuration.

3. The process of claim 1 wherein the process is performed in a reaction vessel which comprises a bottom portion including a gas inlet and a liquid outlet, a top portion including a liquid inlet and a gas outlet, and a middle portion containing a plurality of particles comprising an immobilized carbonic anhydrase or coated with immobilized carbonic anhydrase entrapped in a polymeric immobilization material; the process comprising contacting an aqueous liquid which enters the liquid inlet and flows downward in the reaction vessel with a $CO_2$-containing gas which enters the gas inlet and flows upward in the reaction vessel to promote diffusion of the $CO_2$ into the aqueous liquid and catalyze hydration of the $CO_2$ in the aqueous liquid in the presence of the immobilized carbonic anhydrase to form a treated liquid containing hydrogen ions and bicarbonate ions and a treated gas; evacuating the treated liquid from the liquid outlet and evacuating the treated gas from the gas outlet.

4. The process of claim 3 wherein the $CO_2$-containing gas enters the gas inlet in the form of microbubbles.

5. The process of claim 1 further comprising contacting the treated liquid with particles coated with immobilized carbonic anhydrase entrapped in a polymeric immobilization material, wherein the carbonic anhydrase catalyzes conversion of the hydrogen ions and the bicarbonate ions into concentrated $CO_2$ and water.

6. The process of claim 1 wherein the stabilized carbonic anhydrase retains at least about 15% of its initial catalytic activity for at least about 5 days when continuously catalyzing a chemical transformation at a temperature from about 30° C. to about 100° C.

7. The process of claim 1 wherein the aqueous liquid comprises a base.

8. The process of claim 7 wherein the base is a metal hydroxide, a quaternary ammonium hydroxide, a metal carbonate, a conjugate base of a weak acid, a quaternary ammonium carbonate, a quaternary ammonium alkoxide, a metal amide, a metal alkyl, a metal alkoxide, metal silanoate, an amine, an alkanolamine, or a combination thereof.

9. The process of claim 1 using a system for removing $CO_2$ from a $CO_2$-containing gas comprising a reaction vessel having a bottom portion containing a gas inlet and a liquid outlet, a top portion containing a liquid inlet and a gas outlet, and a middle portion containing a plurality of particles comprising an immobilized carbonic anhydrase or coated with carbonic anhydrase entrapped in a polymeric immobilization material, the carbonic anhydrase being capable of catalyzing hydration of $CO_2$ into hydrogen ions and bicarbonate ions, wherein the polymeric immobilization material comprises a micellar or inverted micellar material.

10. The process for removing $CO_2$ from a $CO_2$-containing gas of claim 9 further comprising a second reaction vessel, the second reaction vessel containing particles coated with carbonic anhydrase entrapped in a polymeric immobilization material wherein the carbonic anhydrase is capable of catalyzing conversion of the hydrogen ions and the bicarbonate ions into concentrated $CO_2$ and water.

11. The process of claim 10 wherein the second reaction vessel contains an immobilization material comprising a micellar or inverted micellar material.

12. A process for removing $CO_2$ from a $CO_2$-containing gas, the process comprising
contacting an aqueous liquid with a $CO_2$-containing gas to promote diffusion of the $CO_2$ into the aqueous liquid; and contacting the $CO_2$ in the aqueous liquid with immobilized carbonic anhydrase entrapped in a polymeric immobilization material to catalyze hydration of the $CO_2$ and form a treated liquid containing hydrogen ions and bicarbonate ions; wherein the polymeric immobilization material stabilizes the carbonic anhydrase and wherein the carbonic anhydrase retains at least about 15% of its initial catalytic activity for at least about 5 days when continuously catalyzing a chemical transformation at a temperature from about 30° C. to about 100° C.

13. The process of claim 1 wherein the immobilization material entraps the carbonic anhydrase, the immobilization material being permeable to a compound smaller than the carbonic anhydrase and having the structure of either Formulae 5, 6, 7, or 8:

Formula 5

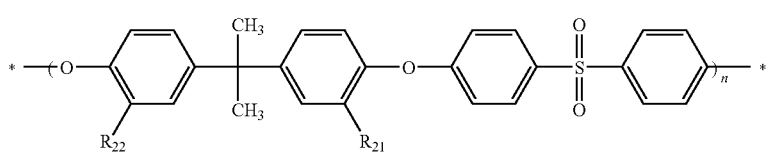

Formula 6

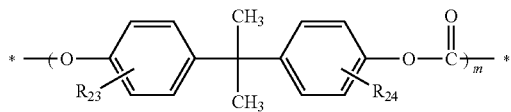

Formula 7

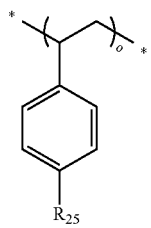

Formula 8

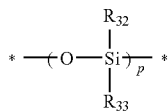

wherein $R_{21}$ and $R_{22}$ are independently hydrogen, alkyl, or substituted alkyl, provided that the average number of alkyl or substituted alkyl groups per repeat unit is at least 0.1;

$R_{23}$ and $R_{24}$ are independently hydrogen, alkyl, or substituted alkyl, provided that the average number of alkyl or substituted alkyl groups per repeat unit is at least 0.1;

$R_{25}$ is hydrogen, alkyl, or substituted alkyl, provided that the average number of alkyl or substituted alkyl groups per repeat unit is at least 0.1;

$R_{32}$ and $R_{33}$ are independently hydrogen, alkyl, aryl, or substituted alkyl, provided that the average number of alkyl or substituted alkyl groups per repeat unit is at least 0.1 and m, n, o, and p are integers of at least 10.

14. The process of claim 13 wherein the immobilization material has a structure of Formula 8.

15. The process of claim 14 wherein $R_{32}$ and $R_{33}$ are independently hydrogen, alkyl, aryl, -(substituted alkylene)-acid or a salt thereof, -(substituted alkylene)-base or a salt thereof, —$(CH_2)_qO$—$(CH_2$—$CH_2$—$O)_z$—$R_t$, —$CH_2$—$O$—$(CH_2$—$CH_3)$—$CH_2$—$O)_z$—$R_t$, or a combination thereof, wherein z is an integer corresponding to a weight average molecular weight of about 150 Da to about 8000 Da, $R_t$ is hydrogen, alkyl, substituted alkyl, aryl, or substituted aryl, and q is an integer of 2, 3, or 4.

16. The process of claim 15 wherein the acid group comprises a carboxylic, a phosphonic, a phosphoric, a sulfonic, a sulfuric, a sulfamate, a salt thereof, or a combination thereof.

17. The process of claim 15 wherein the base comprises a tertiary amine, a quaternary amine, a nitrogen heterocycle, a salt thereof, or a combination thereof.

18. The process of claim 14 wherein $R_{32}$ and $R_{33}$ are independently hydrogen, alkyl, aryl, —$(CH_2)_3$—$O$—$((CH_2)_2$—$O)_z$—$CH_3$, —$(CH_2)_2$—$C(O)$—$O$—$(CH_2)_2$-imidazolium, or —$(CH_2)_3$—$O$—$CH_2$—$CH(OH)$—$N(CH_3)$—$(CH_2)_2$—$SO_3Na$ and z is an integer corresponding to a weight average molecular weight of about 150 Da to about 8000 Da.

19. The process of claim 12 wherein the polymeric immobilization material comprises a micellar or inverted micellar material.

20. The process of claim 12 wherein the aqueous liquid comprises a base.

* * * * *